United States Patent
De Man et al.

(10) Patent No.: US 9,856,258 B2
(45) Date of Patent: Jan. 2, 2018

(54) (5,6-DIHYDRO)PYRIMIDO[4,5-E]INDOLIZINES

(71) Applicant: NETHERLANDS TRANSLATIONAL RESEARCH CENTER B.V., Oss (NL)

(72) Inventors: Adrianus Petrus Antonius De Man, Oss (NL); Rogier Christian Buijsman, Oss (NL); Jan Gerard Sterrenburg, Oss (NL); Joost Cornelis Marinus Uitdehaag, Oss (NL); Joeri Johannes Petrus De Wit, Oss (NL); Guido Jenny Rudolf Zaman, Oss (NL)

(73) Assignee: NETHERLANDS TRANSLATIONAL RESEARCH CENTER B.V., Oss (NL)

(*) Notice: Subject to any disclaimer, the term of this patent is extended or adjusted under 35 U.S.C. 154(b) by 0 days.

(21) Appl. No.: 15/128,874

(22) PCT Filed: Mar. 30, 2015

(86) PCT No.: PCT/EP2015/056839
§ 371 (c)(1),
(2) Date: Sep. 23, 2016

(87) PCT Pub. No.: WO2015/155042
PCT Pub. Date: Oct. 15, 2015

(65) Prior Publication Data
US 2017/0096432 A1  Apr. 6, 2017

(30) Foreign Application Priority Data

Apr. 7, 2014 (EP) .................................. 14163734
Jan. 30, 2015 (EP) .................................. 15153207

(51) Int. Cl.
*C07D 471/14* (2006.01)
(52) U.S. Cl.
CPC .................... *C07D 471/14* (2013.01)
(58) Field of Classification Search
None
See application file for complete search history.

(56) References Cited

FOREIGN PATENT DOCUMENTS

| WO | 2009/156315 A1 | 12/2009 |
|---|---|---|
| WO | 2010/111406 A2 | 9/2010 |
| WO | 2011/013729 A1 | 2/2011 |
| WO | 2011/063908 A1 | 6/2011 |
| WO | 2012/080229 A1 | 6/2012 |
| WO | 2012/101032 A1 | 8/2012 |

OTHER PUBLICATIONS

Lapenna, Silvia. Nature Reviews: Drug Discovery. (2009) 547-566.*
Jemaa, M. Cell Death and Differentiation (2013) 1532-1545.*
Colombo, Riccardo. Cancer Res; 70(24) (2010) 10255-10264.*
Myeloproliferative disorders: University of Maryland Medical Center. (2016).Web: <http://umm.edu/health/medical/altmed/condition/myeloproliferative-disorders>.*
MedicineNet.com (2004). Web<http://www.medterms.com>.*
May 8, 2015 International Search Report issued in International Patent Application No. PCT/EP2015/056839.
May 8, 2015 Written Opinion of the International Searching Authority issued in International Patent Application No. PCT/EP2015/056839.

* cited by examiner

*Primary Examiner* — Deepak R Rao
*Assistant Examiner* — Laura M Daniel
(74) *Attorney, Agent, or Firm* — Oliff PLC

(57) ABSTRACT

A compound of Formula I:

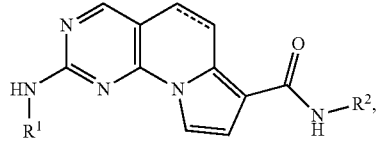

Formula I wherein, $R^1$ and $R^2$ independently are selected from the group consisting of optionally substituted (6-10C)aryl and (1-5C)heteroaryl groups. The compounds can be used in pharmaceutical compositions, in particular in the treatment of cancer.

13 Claims, No Drawings

(5,6-DIHYDRO)PYRIMIDO[4,5-E]INDOLIZINES

The present invention relates to (5,6-dihydro)pyrimido[4,5-e]indolizines, to pharmaceutical compositions comprising these compounds and their use in therapy. In particular, the present invention relates to the use of (5,6-dihydro)pyrimido[4,5-e]indolizines in the treatment of cancer.

The present invention relates to chemical compounds, which modulate the activity of protein kinases, in particular inhibit the activity of the protein kinase TTK (EC 2.7.12.1). TTK, commonly referred to as Mps1, is a component of the mitotic checkpoint, a machinery that ensures the fidelity of sister chromatid segregation over two daughter cells during cell division. Defects in or inhibition of the mitotic checkpoint leads to aneuploidy. During embryonic development the vast majority of single segregation errors is not tolerated (Cohen, J., Science 296: 2164, 2002). In contrast, aneuploidy is a common genetic alteration in solid human tumors (Lengauer, C. et al., Nature 396, 643; 1998) and a predictor of poor prognosis in breast, lung, brain (Carter, S. L., et al., Nat. Genet. 38: 1043; 2006; Tannous, B. A., et al., J. Nat. Canc. Inst. 105, 1322; 2013) and colorectal cancer (Walther, A. et al., Gut 57: 941; 2008; Sheffer, M. et al., Proc. Natl. Acad. Sci. USA 106: 7131, 2009), TTK expression is increased in breast cancer with chromosomal instability (Yuan, B. et al., Clin. Cancer Res. 12: 405; 2006) and in particular in triple negative breast cancer, the most aggressive type of breast cancer (Maire, V. et al, PLoS ONE 8(5) e63712; 2013). Reducing TTK expression by RNA interference resulted in gross chromosome mis-segregation and cell death, but did not affect cell viability of normal (untransformed) cells (Yuan, B. et al.; Maire, V. et al; Janssen, A. et al., Proc. Natl. Acad. Sci. USA 106: 19108; 2009). Partial inhibition of TTK expression by RNA interference in different tumor cell line lines caused mild chromosome mis-segregations, but no lethality (Janssen, A. et al.). These cells were, however, more sensitive to treatment with low doses of anti-mitotic agents, such as paclitaxel (Janssen, A. et al.) and vincristine (Tannous, B. A., et al.). Above data provide the biological basis for TTK inhibitors as an approach for selective anti-cancer therapy.

TTK kinase inhibitors are useful for the treatment of a variety of cancers and may be applied as single agents, or in combination with other chemotherapeutic agents.

WO 2012/101032 A1 (Nerviano Medical Sciences SRL) relates to tricyclic pyrrolo derivatives which modulate the activity of protein kinases and are therefore useful in treating diseases caused by dysregulated protein kinase activity.

In WO2011/063908A1, triazolopyridines, and in WO2012/080229A1 and WO2011/013729A1, imidazopyrazines are disclosed as inhibitors of TTK by Bayer Schering Pharma A. G. Characterization of three representative inhibitors showed inhibition of TTK kinase activity with $IC_{50}$ of 1 to 10 nM and inhibition proliferation of human cancer cell lines with $IC_{50}$s ranging from 160 nM to >10 µM (Jemaà, M. et al., Cell Death Different. 20: 1532; 2013). One of the compounds, Mps-BAY2b, was shown to inhibit HeLa-Matu cervical tumor cell growth in a mouse xenograft model and increased the efficacy of paclitaxel in this model (Jemaà, M. et al.), thus confirming the chemotherapy sensitizing effect of TTK inhibition previously shown with RNA interference techniques (Janssen, A. et al.).

In WO2009/156315A1 pyrazolo-quinazolines are disclosed as inhibitors of TTK by Nerviano Medical Sciences S.R.L. A compound described in this parent, NMS-P715, inhibited TTK kinase activity with a half-maximal inhibitory concentration ($IC_{50}$) of 8 to 182 nM, depending on whether a pre-incubation step was included in the assay or not (Colombo, R., et al., Cancer Res. 70: 10255; 2010). NMS-P715 also inhibited the proliferation of cancer cell lines from different tumor origin with $IC_{50}$s of 1 µM and higher, and inhibited tumor growth in A375 and A2780 mouse xenograft models (Columbo, R. et al.).

In WO2010/111406A2 compounds are disclosed as inhibitors of TTK by Myriad Pharmaceuticals, Inc. A representative compound, MPI 4079605, inhibited TTK with an $IC_{50}$ of 1.8 nM (Tardif, K. D., et al., Mol. Cancer Res. 10:2267; 2011). Treatment of cancer cell lines for 72 hours revealed many cell lines with little sensitivity (Tardif K. D., et al.). MPI 4079605 is structurally similar to reversine and MPS1-IN-1, two other published inhibitors of TTK (Kwiatkowski, N., et al., Nat. Chem. Biol. 6: 359; 2010; Santiguida, S., et al., J. Cell. Biol. 190: 73; 2010).

There is a clear need of TTK inhibitors with potent kinase inhibitory and anti-proliferative activity.

We have synthesized a series of (5,6-dihydro)pyrimido[4,5-e]indolizine and found these compounds to be very effective inhibitors of TTK kinase activity and proliferation of tumor cell growth.

The present invention provides (5,6-dihydro)pyrimido[4,5-e]indolizine derivatives.

More specifically, the present invention provides (5,6-dihydro)pyrimido[4,5-e]indolizine derivatives according to formula I or pharmaceutically acceptable salts thereof.

The present invention provides compounds which inhibit TTK activity, their use for treatment of hyper-proliferative disorders, in particular cancers that are caused by, or associated with chromosomal instability or aneuploidy, as a sole agent or in combination with other active ingredients, as well as pharmaceutical compositions comprising such compounds and pharmaceutical carriers.

The object of the present invention is to provide (5,6-dihydro)pyrimido[4,5-e]indolizines, to pharmaceutical compositions comprising these compounds and their use in therapy. In particular, the present invention relates to the use of (5,6-dihydro)pyrimido[4,5-e]indolizines in the treatment of cancer.

More specifically, the present invention provides (5,6-dihydro)pyrimido[4,5-e]indolizines according to Formula I or pharmaceutically acceptable salts thereof.

Formula I

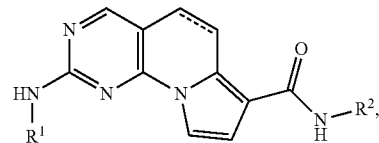

wherein,
  $R^1$ and $R^2$ are independently selected from the group consisting of:
    a) (6-10C)aryl,
    b) (1-5C)heteroaryl,
  wherein both groups optionally can be substituted.

In one embodiment $R^1$ is selected from the group consisting of:

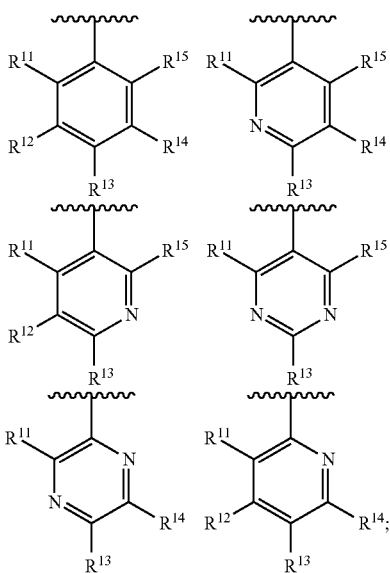

$R^{11}$ is H, halogen, (1-2C)alkyl, (2-3C)alkenyl, (2-3C)alkynyl, (1-2C)alkoxy or $OC^2H_3$, all alkyl and alkoxy groups optionally being substituted with one or more halogen;

$R^{12}$ is H, halogen, (1-2C)alkyl or (1-2C)alkoxy;

$R^{13}$ is $R^{131}CH_2$, $R^{132}O$, $R^{133}R^{134}N$, $R^{135}C(O)$, $R^{136}S$, $R^{136}S(O)$, $R^{136}S(O)(NH)$, $R^{137}SO_2$, (2-7C)heterocycloalkyl, or (1-5C)heteroaryl each heterocycloalkyl or heteroaryl optionally being substituted with (1-2C)alkyl, fluoro, hydroxyl, oxo, (1-2C)alkoxy, (1-6C)alkylcarbonyl, (1-6C)alkylsulfonyl, (1-5C)alkoxycarbonyl, (1-6C)alkylaminocarbonyl, (3-6C)cycloalkylcarbonyl, (2-7C)heterocycloalkylcarbonyl or di[(1-2C)alkyl]amino, each alkylcarbonyl, alkylsulfonyl, alkoxycarbonyl, alkylaminocarbonyl, cycloalkylcarbonyl or heterocycloalkylcarbonyl optionally being substituted with (1-2C)alkyl, fluoro, hydroxyl, cyano, oxo or (1-2C)alkoxy;

$R^{131}$ is (1-6C)alkylcarbonylamino, (3-6C)cycloalkylcarbonylamino or (2-7C)heterocycloalkylcarbonylamino each optionally substituted with one or more groups selected from (1-2C)alkyl, fluoro, hydroxyl or (1-2C)alkoxy;

$R^{132}$ is (1-6C)alkyl, (3-6C)cycloalkyl, (2-7C)heterocycloalkyl, (6-10C)aryl or (1-5C)heteroaryl each optionally substituted with one or more groups selected from (1-2C)alkyl, halogen, hydroxyl, (1-2C)alkoxy, di[(1-2C)alkyl]amino or (2-7C)heterocycloalkyl;

$R^{133}$ is (1-6C)alkyl, (3-6C)cycloalkyl, (2-7C)heterocycloalkyl (1-6C)alkylcarbonyl, (1-5C)alkoxycarbonyl, (3-6C)cycloalkylcarbonyl or (2-7C) heterocycloalkylcarbonyl, each optionally substituted with one or more groups selected from (1-2C)alkyl, halogen, hydroxyl or (1-2C)alkoxy, di[(1-2C)alkyl]amino or (2-7C)heterocycloalkyl;

$R^{134}$ is hydrogen or (1-2C)alkyl;

$R^{135}$ is (2-7C)heterocycloalkyl, (1-6C)alkylamino, di[(1-6C)alkyl]amino, (2-7C)heterocycloalkylamino or (3-6C)cycloalkylamino each optionally substituted with one or more groups selected from (1-2C)alkyl, fluoro, hydroxyl, (1-2C)alkoxy, di[(1-2C)alkyl]amino, (2-7C)heterocycloalkyl, oxo, cyano or amino;

$R^{136}$ is (1-6C)alkyl, (3-6C)cycloalkyl, (2-7C)heterocycloalkyl each optionally substituted with one or more groups selected from (1-2C)alkyl, fluoro, hydroxyl or (1-2C)alkoxy;

$R^{137}$ is (1-6C)alkyl, (3-6C)cycloalkyl, (2-7C)heterocycloalkyl, (1-6C)alkylamino, di[(1-6C)alkyl]amino, (2-7C)heterocycloalkylamino or (3-6C)cycloalkylamino, each optionally substituted with one or more groups selected from (1-2C)alkyl, fluoro, hydroxyl or (1-2C)alkoxy;

$R^{14}$ is H, halogen, (1-2C)alkyl or (1-2C)alkoxy; and $R^{15}$ is H, halogen.

In the above Formula I, $R^2$ is selected from the group consisting of:

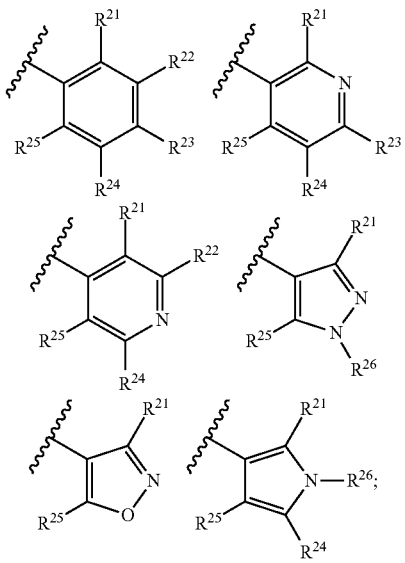

$R^{21}$ is H, halogen, (1-3C)alkyl, (1-2C)alkoxy, hydroxy(1-2C)alkyl, (3-4C)cycloalkyl, (2-3C)alkenyl or cyano;

$R^{22}$ is H, halogen, (1-2C)alkyl or (1-2C)alkoxy;

$R^{23}$ is H, halogen, (1-2C)alkyl, (1-2C)alkoxy, cyano or hydroxy;

$R^{24}$ is H, halogen, (1-2C)alkyl or (1-2C)alkoxy;

$R^{25}$ is H, halogen, (1-3C)alkyl, (1-2C)alkoxy, hydroxy(1-2C)alkyl, (3-4C)cycloalkyl, (2-3C)alkynyl or cyano;

$R^{26}$ is H, (1-6C)alkyl, (3-6C)cycloalkyl, (2-5C)heterocycloalkyl, (1-2C)alkoxy[(2-4C)alkoxy]$_n$((1-6C)alkyl, wherein n represents an integer of 1, 2, 3 or 4, all alkyl, heterocycloalkyl and (1-2C)alkoxy[(2-4C)alkoxy]$_n$(1-6C)alkyl groups optionally substituted with one or more groups selected from (1-2C)alkyl, (1-2C)alkoxy, hydroxyl, oxo, amino, (3-6C)cycloalkyl, di[(1-2C)alkyl]amino or (2-5C)heterocycloalkyl.

In an interesting embodiment $R^2$ is selected from a group consisting of:

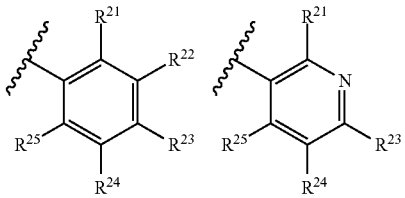

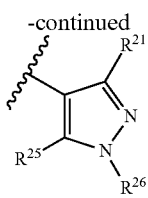

Moreover, very potent TTK inhibitors with excellent selectivity over Polo-like kinase 1 (PLK1) have been demonstrated where $R^2$ is:

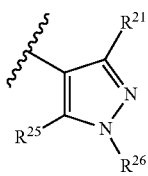

As a corollary to this selectivity over PLK1, compounds meeting this definition of $R^2$ often demonstrate a high selectivity for Aurora A (AurA) and/or Aurora C (AurC) kinases.

In the above Formula I only one of $R^{21}$ and $R^{25}$ is $R^2$ can be H.

The terms as used herein refer to the following:

Halogen means fluorine, chlorine, bromine or iodine, fluorine, chlorine or bromine being preferred halogens, fluorine or chlorine being more preferred.

(1-2C)Alkyl means an alkyl group having 1 to 2 carbon atoms, being methyl or ethyl. A methyl group may be indicated as Me or $CH_3$.

(1-3C)Alkyl means a branched or unbranched alkyl group having 1-3 carbon atoms, being methyl, ethyl, propyl or isopropyl.

(1-4C)Alkyl means a branched or unbranched alkyl group having 1-4 carbon atoms, being methyl, ethyl, propyl, isopropyl, butyl, isobutyl, sec-butyl or tert-butyl, (1-3C) alkyl groups being preferred.

(1-5C)Alkyl means a branched or unbranched alkyl group having 1-5 carbon atoms, for example methyl, ethyl, propyl, isopropyl, butyl, isobutyl, sec-butyl, tert-butyl, pentyl and isopentyl, (1-4C)alkyl groups being preferred.

(1-6C)Alkyl means a branched or unbranched alkyl group having 1-6 carbon atoms, for example methyl, ethyl, propyl, isopropyl, butyl, tert-butyl, n-pentyl and n-hexyl. (1-5C)alkyl groups being preferred, (1-4C)alkyl being more preferred.

(1-2C)Alkoxy means an alkoxy group having 1-2 carbon atoms, the alkyl moiety having the same meaning as previously defined.

(2-4C)Alkoxy means an alkoxy group having 2-4 carbon atoms, for example ethoxy, propyloxy, butyloxy, isopropyloxy, isobutyloxy, and tertbutyloxy. Ethyloxy and propyloxy being preferred. Ethyloxy groups being more preferred.

(1-3C)Alkoxy means an alkoxy group having 1-3 carbon atoms, the alkyl moiety having the same meaning as previously defined. (1-2C)Alkoxy groups are preferred.

(1-4C)Alkoxy means an alkoxy group having 1-4 carbon atoms, the alkyl moiety having the same meaning as previously defined. (1-3C)alkoxy groups are preferred, (1-2C)alkoxy groups being most preferred.

(1-5C)Alkoxy means an alkoxy group having 1-5 carbon atoms, the alkyl moiety having the same meaning as previously defined. (1-4C)Alkoxy groups are preferred, (1-3C)alkoxy groups being more preferred.

(2-3C)Alkenyl means a branched or unbranched alkenyl group having 2-3 carbon atoms, such as ethenyl or 2-propenyl.

(2-3C)Alkynyl means ethynyl or 2-propynyl.

(3-4C)Cycloalkyl means a cycloalkyl group having 3-4 carbon atoms, being cyclopropyl or cyclobutyl (3-6C)Cycloalkyl means a cycloalkyl group having 3-6 carbon atoms, being cyclopropyl, cyclobutyl, cyclopentyl or cyclohexyl. Cyclopropyl and cyclobutyl are preferred.

(2-5C)Heterocycloalkyl means a heterocycloalkyl group having 2-5 carbon atoms, preferably 3-5 carbon atoms; and one or two heteroatoms selected from N, O and/or S, which may be attached via a heteroatom if feasible, or a carbon atom. Preferred heteroatoms are N or O. Preferred are oxetanyl, azetidinyl, piperidinyl, morpholinyl, pyrrolidinyl and piperazinyl. Most preferred (2-5C)heterocycloalkyl are oxetanyl and azetidinyl.

(2-7C)Heterocycloalkyl means a heterocycloalkyl group having 2-7 carbon atoms, preferably 2-5 carbon atoms, and one or two heteroatoms selected from N, O and/or S. Preferred heteroatoms are N or O. Preferred (2-7C)heterocycloalkyl are azetidinyl, pyrrolidinyl, piperidinyl, piperazinyl, homopiperidinyl, morpholinyl or thiomorpholinyl. The heterocycloalkyl group may be attached via a heteroatom if feasible.

(6-10C)Aryl means an aromatic hydrocarbon group having 6-10 carbon atoms, such as phenyl, naphthyl, tetrahydronaphthyl or idenyl. The preferred (6-10C)aryl group is phenyl.

(1-5C)Heteroaryl means a substituted or unsubstituted aromatic group having 1-5 carbon atoms and 1-4 heteroatoms selected from N, O and/or S. The (1-5C)heteroaryl may optionally be substituted. Preferred (1-5C)heteroaryl groups are isoxazolyl, pyrazolyl, pyridyl, pyrimidyl, pyrazinyl, more preferred (1-5C)heteroaryls are pyrazolyl, isoxazolyl, pyridinyl and pyrimidyl.

(3-6C)Cycloalkylamino means an amino group, monosubstituted with an cycloalkyl group containing 3-6 carbon atoms having the same meaning as previously defined.

(1-6C) Alkylamino means an amino group, monosubstituted with an alkyl group containing 1-6 carbon atoms having the same meaning as previously defined. Preferred (1-6C) alkylamino group is methylamino.

Di[(1-2C)alkyl]amino means an amino group, disubstituted with alkyl group(s), each independently containing 1-2 carbon atoms and having the same meaning as previously defined. Preferred di[(1-2C)alkyl]amino group is dimethylamino.

Di[(1-6C)alkyl]amino means an amino group, disubstituted with alkyl group(s), each independently containing 1-6 carbon atoms and having the same meaning as previously defined. Preferred di[(1-6C)alkyl]amino group is N-methylpropan-1-amino.

(2-7C)heterocycloalkylamino means in an amino group, monosubstituted with a (2-7)heterocycloalkyl group containing 2-7 carbon atoms having the same meaning as previously defined.

(1-6C)Alkylaminocarbonyl means a carbonyl group substituted with an amino group. Said amino group being monosubstituted with an alkyl group having 1-6 carbon atoms and having the same meaning as previously defined.

(2-7C)Heterocycloalkylcarbonyl means a carbonyl group substituted with an (2-7C)heterocycloalkyl group having 2-7 carbon atoms and having the same meaning as previously defined.

(1-5C)Alkoxycarbonyl means a carbonyl group substituted with an alkoxy group the alkyl moiety of which having 1-6 carbon atoms as previously defined.

(1-6C)Alkylsulfonyl means a sulfonyl group substituted with an (1-6C)alkyl group having 1-6 carbon atoms and having the same meaning as previously defined.

(1-6C)Alkylcarbonyl means a carbonyl group substituted with an (1-6C)alkyl group having 1-6 carbon atoms and having the same meaning as previously defined.

(3-6C)Cycloalkylcarbonyl means a carbonyl group substituted with an (3-6C)cycloalkyl group having 3-6 carbon atoms and having the same meaning as previously defined.

(1-6C)Alkylaminocarbonyl means a carbonyl group substituted with an amino group. Said amino group being monosubstituted with an alkyl group having 1-6 carbon atoms and having the same meaning as previously defined.

(1-6C)Alkylcarbonylamino means an amino group substituted with a carbonyl group. Said carbonyl group being monosubstituted with an aklyl group having 1-6 carbon atoms and having the same meaning as previously defined.

(3-6C)Cycloalkylcarbonylamino means an amino group substituted with a carbonyl group. Said carbonyl group being monosubstituted with a cycloalkyl group having 3-6 carbon atoms and having the same meaning as previously defined.

(2-7C)Heterocycloalkylcarbonylamino means an amino group substituted with a carbonyl group. Said carbonyl group being monosubstituted with a (2-7C)heterocycloalkyl group having 2-7 carbon atoms and having the same meaning as previously defined.

Hydroxy(1-2C)alkyl means a (1-2C)alkyl group having 1-2 carbon atoms with the same meaning as previously defined, substituted with a hydroxyl group.

(1-2C)Alkoxy[(2-4C)alkoxy]$_n$(1-6C)alkyl means a (1-6C) alkyl group having 1-6 carbon atoms with the same meaning as previously defined, substituted with one or more (2-4C)alkyloxy groups, wherein n represents an integer of 1, 2, 3 or 4, the alkoxy groups being linearly connected one to another. The last (2-4C)alkyloxy group being substituted with an (1-2C)alkyloxy group. In the (1-2C)alkoxy[(2-4C)alkoxy]$_n$(1-6C)alkyl group, the preferred (1-2C)alkoxy group is methoxy, the preferred (2-4C)alkoxy is ethoxy, and the preferred (1-6C)alkyl is ethyl, preferably n is 1, 2, 3, 4, n is 1 or 2 being most preferred.

In the above definitions with multifunctional groups, the attachment point is at the last group.

When in the definition of a substituent, is indicated that "all of the alkyl groups" of said substituent are optionally substituted, this also includes the alkyl moiety of an alkoxy group.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds.

"Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

In one embodiment the invention relates to a compound according Formula I wherein $R^{13}$ is $R^{132}O$, $R^{135}C(O)$, (2-7C)heterocycloalkyl or (1-5C)heteroaryl each heterocycloalkyl or heteroaryl optionally being substituted with (1-2C)alkyl, (1-6C)alkylcarbonyl, (1-6C)alkylsulfonyl, (1-5C)alkoxycarbonyl, (1-6C)alkylaminocarbonyl, (3-6C) cycloalkylcarbonyl or (2-7C)heterocycloalkylcarbonyl, each alkylcarbonyl, alkylsulfonyl, alkoxycarbonyl, alkylaminocarbonyl, cycloalkylcarbonyl or heterocycloalkylcarbonyl optionally being substituted with (1-2C)alkyl, fluoro, (1-2C)alkoxy; $R^{132}$ is selected from a group consisting of (1-6C)alkyl, (3-6C)cycloalkyl, (2-7C)heterocycloalkyl, (6-10C)aryl or (1-5C)heteroaryl, each optionally substituted with one or more groups selected from (1-2C)alkyl, halogen, hydroxyl, (1-2C)alkoxy, di[(1-2C)alkyl]amino or (2-7C)heterocycloalkyl and $R^{135}$ is selected from a group consisting of (2-7C)heterocycloalkyl, (1-6C)alkylamino, di[(1-6C)alkyl] amino, (2-7C)heterocycloalkylamino or (3-6C)cycloalkylamino, each optionally substituted with one or more groups selected from (1-2C)alkyl, fluoro, hydroxyl, (1-2C)alkoxy, di[(1-2C)alkyl]amino, (2-7C)heterocycloalkyl, oxo, cyano or amino.

In yet another embodiment the invention relates to a compound according to Formula I wherein $R^{13}$ is $R^{132}O$, $R^{135}C(O)$; or $R^{13}$ is piperidinyl, piperazinyl, morpholinyl, pyrazolyl or isoxazolyl (each optionally being substituted with (1-2C)alkyl, (1-6C)alkylcarbonyl, (1-6C)alkylsulfonyl, (1-5C)alkoxycarbonyl, (1-6C)alkylaminocarbonyl, (3-6C) cycloalkylcarbonyl or (2-7C)heterocycloalkylcarbonyl each alkylcarbonyl, alkylsulfonyl, alkoxycarbonyl, alkylaminocarbonyl, cycloalkylcarbonyl or heterocycloalkylcarbonyl optionally being substituted with (1-2C)alkyl, fluoro or (1-2C)alkoxy. $R^{132}$ is selected from a group consisting of (1-6C)alkyl, piperidinyl, pyrrolidinyl or azetidinyl, each optionally being substituted with one or more groups selected from (1-2C)alkyl, (1-2C)alkoxy or di[(1-2C)alkyl] amino and $R^{135}$ is selected from a group consisting of piperidinyl, thiomorpholinyl, morpholinyl, homo-piperazinyl, (1-6C)alkylamino, (3-6C)cycloalkylamino or piperidinylamino, azetidinylamino, tetrahydropyranylamino or 3-oxabicyclo[3.1.0]hexan-6-amino, each optionally being substituted with one or more groups selected from (1-2C) alkyl, fluoro, hydroxyl or (1-2C)alkoxy, di[(1-2C)alkyl] amino, (2-7C)heterocycloalkyl, oxo, cyano or amino.

In another embodiment the present invention relates to a compound according to Formula I wherein $R^1$ is selected from a group consisting of:

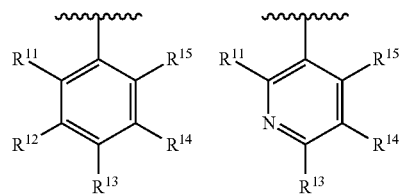

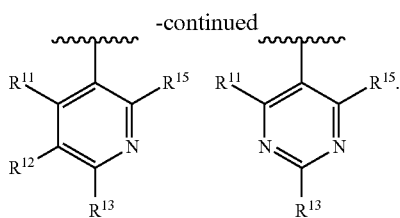

In again another embodiment the present invention relates to a compound according Formula I wherein $R^{12}$ and $R^{15}$ each are H and $R^{14}$ is H, fluoro, chloro or (1-2C)alkyl.

The invention also relates to compounds according to Formula I wherein $R^{11}$ is H, (1-2C)alkyl or (1-2C)alkoxy, all alkyl and alkoxy groups optionally being substituted with one or more fluoro.

In yet another embodiment the invention relates to a compound according to Formula I wherein $R^2$ is selected from group consisting of:

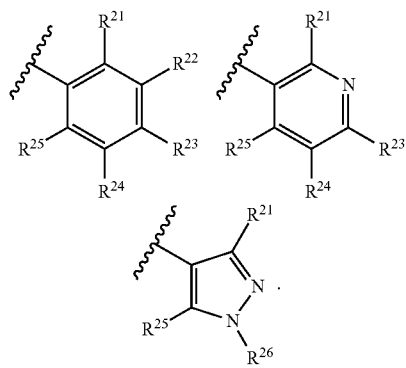

In a particular embodiment, the invention relates to a compound according to Formula I in which $R^2$ is:

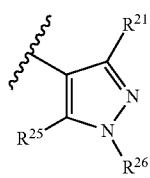

In again another embodiment the invention relates to a compound according to Formula I wherein $R^{23}$ is H or (1-6C)alkyl and $R^{22}$ and $R^{24}$ each are H.

In another embodiment the invention relates to a compound according to Formula wherein $R^{21}$ is selected from group consisting of H, halogen, (1-6C)alkyl or cyano.

In again another embodiment the invention relates to a compound according to Formula I wherein $R^{23}$ is H or (1-2C)alkyl and $R^{22}$ and $R^{24}$ each are H and $R^{21}$ and $R^{25}$ are independently selected from a group consisting of halogen, (1-3C)alkyl, methoxy, hydroxymethyl or cyano.

In another embodiment the invention relates to a compound according to Formula I wherein $R^{26}$ is H, (1-6C)alkyl, oxetanyl, azetidinyl or (1-2C)alkoxy[(2-4C)alkoxy]$_n$(1-6C)alkyl, wherein n represents an integer of 1 or 2, all alkyl, oxetanyl and azetidinyl groups optionally being substituted with one or more groups selected from (1-2C)alkyl, (1-2C)alkoxy, hydroxyl, di[(1-2C)alkyl]amino or oxetanyl.

The invention also relates to those compounds wherein all specific definitions $R^1$, $R^2$, $R^{11-15}$, $R^{21-26}$ and $R^{131-137}$ and all substituent groups in the various aspects of the inventions defined here above occur in any combination within the definition of the compound of the Formula I.

In another aspect of the invention the compounds of the invention have an inhibitory potency on TTK with an $IC_{50}$ of 10 µM or lower. In another aspect the invention relates to compounds of Formula I which have an inhibitory potency on TTK with an $IC_{50}$ of less than 100 nM. In yet another aspect the invention relates to compounds of Formula I which have an inhibitory potency on TTK with an $IC_{50}$ of less than 10 nM.

The term $IC_{50}$ means the concentration of the test compound that is required for 50% inhibition of its maximum effect in vitro.

Inhibition of TTK kinase activity can be measured using the Immobilized Metal Assay for Phosphochemicals (IMAP) assay. IMAP is a homogeneous fluorescence polarization (FP) assay based on affinity capture of phosphorylated peptide substrates. IMAP uses fluorescein-labeled peptide substrates that, upon phosphorylation by a protein kinase, bind to so-called IMAP nanoparticles, which are derivatized with trivalent metal complexes. Binding causes a change in the rate of the molecular tumbling of the peptide, and results in an increase in the FP value observed for the fluorescein label attached to the substrate peptide (Gaudet, E. A. et al. J. Biomol. Screen 8: 164; 2003).

The biological activity of TTK inhibitors can be measured, in proliferation assays with tumor cell lines. The activity of the compounds on tumor cells can also be determined in colony formation assays, and in the context of an animal model, in mice grafted with human or mouse cell lines or tumor tissue.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I may contain both a basic moiety, such as, but not limited to a pyridine or imidazole, and an acidic moiety, zwitterions ("inner salts") may be formed and are included within the term "salt(s)" as used herein. Pharmaceutically acceptable (i.e., non-toxic, physiologically acceptable) salts are preferred. Salts of the compounds of the Formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochylorides, hydrobromides, hydroiodides, lactates, maleates, methanesulfonates, naphthanelesulfonates, nitrates, oxalates, phosphates, propionates, salicylates, succinates, sulfates, tartrates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, J. of Pharm. Sci. (1977) 66(1) 1-19; P. Gould, Int. J. Pharm. (1986) 33 201-217; Anderson et al, The practice of Medicinal Chemistry (1996), Academic Press, New York; and in The Orange Book (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, tert-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral a HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomeres, and diastereomeric forms, are contemplated within the scope of this invention. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the compounds according to the invention.

The compounds having Formula (I) or the pharmaceutically accepted salts may form hydrates or solvates. It is known to those of skill in the art that charged compounds from hydrated species when lyophilized with water, or form solvated species when concentrated in a solution with an appropriate organic solvent. The compounds of this invention include the hydrates or solvates of the compounds listed.

In the compounds of Formula I, the atoms may exhibit their natural isotopic abundances, or one or more of the atoms may be artificially enriched in a particular isotope having the same atomic number, but an atomic mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature.

Substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labeled reagent for a non-isotopically labeled reagent.

The compounds of the present invention can be used for therapy.

In one aspect the compounds of the present invention can be used for the treatment of TTK-mediated diseases or conditions. In particular, the compounds of Formula I or their salts, and pharmaceutical compositions thereof can be used to treat diseases and conditions caused by or associated with overexpression or over-activity of the TTK protein, and/or abnormal expression, activity, or regulation of any regulators of TTK activity, or other regulators of the mitotic checkpoint, such as MAD1, MAD2, BUB1, BUBR1, BUB3 and others (Kops, G. J. P. L., et al.; Nature Rev. Cancer 5: 773; 2005).

Thus, in one aspect of the invention the compounds according to Formula I or pharmaceutically acceptable salts thereof can be used to treat diseases and conditions caused by or associated with overexpression or over-activity of the TTK protein.

In another aspect compounds according to Formula I or a pharmaceutically acceptable salt thereof can be used to treat hyperproliferative disorders.

The invention thus relates to a method of regulating, modulating, or inhibiting TTK for the prevention and/or treatment of hyperproliferative disorders.

In another aspect the compounds of the present invention can be used for the treatment of diseases or conditions caused by abnormal cell proliferation, and/or diseases associated with chromosomal instability, chromosomal rearrangements, and/or aneuploidy.

In yet another aspect the compounds of the present invention can be used for the treatment of cancer, in particular for the treatment or prophylaxis of diseases caused by, or associated with uncontrolled cell growth, cell proliferation and/or cell survival.

In another aspect the compounds of the present invention can be used for the treatment of solid tumors, haematological tumors, and/or metastases thereof, e.g., mammary and gynaecological tumours, head and neck tumors, brain tumors and brain metastases, tumors of the thorax including non-small cell and small cell lung tumors, gastrointestinal tumors, endocrine tumors, urological tumors including renal, bladder and prostate tumors, skin tumor, and sarcomas, leukaemias and myelodysplastic syndrome, malignant lymphomas, and/or metastases thereof.

A further aspect of the invention resides in the use of a compound of Formula I or a pharmaceutically salt thereof for the manufacture of a medicament to be used to treat diseases and conditions caused by or associated with overexpression or over-activity of the TTK protein and for the treatment of disorders in which hyperproliferative cells play a prominent role.

Included herein are methods of treatment and/or pharmaceutical compositions in which at least one compound of Formula I or a pharmaceutically salt thereof is administered in combination with at least one other active agent. The other active agent can be a chemotherapeutic agent, an antibody, or an active polypeptide.

The another aspect the invention concerns a compound of Formula I in combination with one or more other drug(s).

The invention further provides a pharmaceutical composition, which comprises a compound of Formula I and salts thereof, and one or more pharmaceutically acceptable carriers, diluents, or excipients. The carrier(s), diluent(s) or excipient(s) must be acceptable in the sense of being compatible with the other ingredients of the formulation and not deleterious to the recipient thereof.

Mixed with such pharmaceutically acceptable auxiliaries, e.g. as described in the standard reference, Gennaro, A. R. et al., Remington: The Science and Practice of Pharmacy (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

Pharmaceutical compositions of the present invention may be presented in unit dose forms containing a predetermined amount of active ingredient per unit dose. Such a unit may contain, for example 5 µg to 1 g, preferably 1 mg to 700 mg, more preferably 5 mg to 100 mg of a compound of the Formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as here in above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

The compound of the present invention can also be administered as a protein-drug conjugate. The compound can be covalently bound, optionally with a linker molecule to a peptide or protein, such as a binding protein for example an antibody. Using this approach, the conjugate can be delivered to the target tissue. Methods to prepare such conjugates are well known to those skilled in the art.

It will be appreciated that when the compound of the present invention is administered in combination with other therapeutic agents normally administered by the inhaled, intravenous, oral or intranasal route, that the resultant pharmaceutical composition may be administered by the same routes.

A therapeutically effective amount of a compound of the present invention will depend upon a number of factors including, for example, the age and weight of the animal, the precise condition requiring treatment and its severity, the particular compound having Formula I, the nature of the formulation, and the route of administration, and will ultimately be at the discretion of the attendant physician or veterinarian. However, an effective amount of a compound of Formula I for the treatment of diseases or conditions associated with inappropriate TTK activity, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula I per se.

In general parenteral administration requires lower dosages than other methods of administration which are more dependent upon absorption. However, a dosage for humans preferably contains 0.001-25 mg of a compound of Formula I or pharmaceutically salts thereof per kg body weight. The desired dose may be presented as one dose or as multiple sub-doses administered at appropriate intervals throughout the day, or, in case of female recipients, as doses to be administered at appropriate daily intervals throughout the menstrual cycle. The dosage, as well as the regiment of administration, may differ between a female and a male recipient.

The present invention also relates to a pharmaceutical composition comprising a compound of Formula I or pharmaceutically salt thereof in a mixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition comprising at least one compound of Formula I or pharmaceutically salts thereof in combination with at least one other therapeutically active agent.

For the treatment of cancer a compound of Formula I may be combined with one or more anticancer agents. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved.

The (5,6-dihydro)pyrimido[4,5-e]indolizine derivatives of the present invention can be prepared by methods well known in the art of organic chemistry. See, for example, J. March, 'Advanced Organic Chemistry' 4th Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 3rd Edition, John Wiley and Sons, 1999. The protective groups are optionally removed at a convenient subsequent stage using methods well known in the art.

The products of the reactions are optionally isolated and purified, if desired, using conventional techniques, including but not limited to, filtration, distillation, crystallization, chromatography and the like. Such materials are optionally characterized using conventional means, including physical constants and spectral data.

5,6-Dihydropyrimido[4,5-e]indolizines compounds of Formula I, wherein $R^1$-$R^x$ have the previously defined meanings, can be prepared by the general synthetic route shown in scheme I.

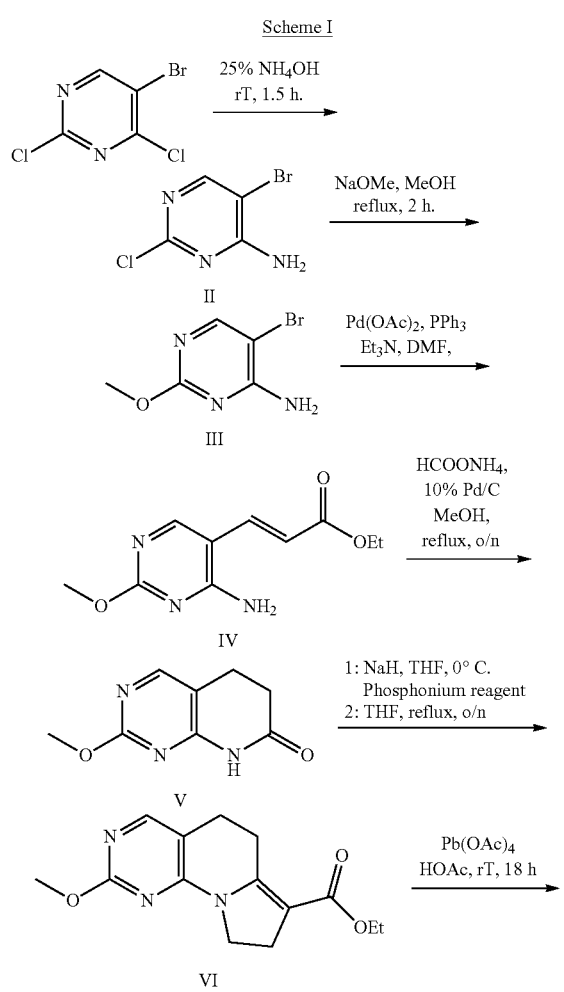

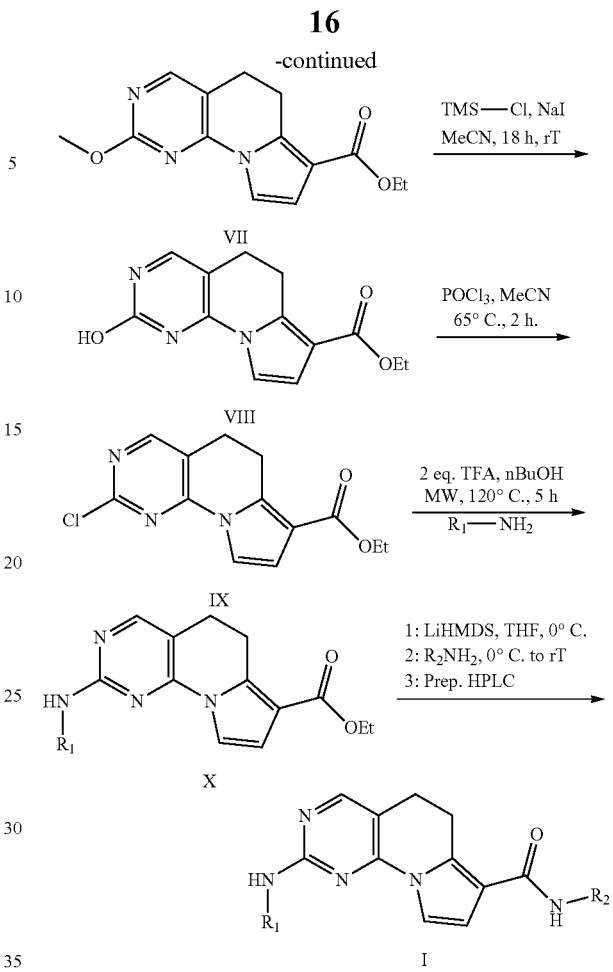

5-Bromo-2-chloro-pyrimidin-4-amine (II) can be prepared from commercial available 5-bromo-2,4-dichloro-pyrimidine using 25% aqueous ammonia at ambient temperature. The resulting product can then be reacted with sodium methanolate in methanol at elevate temperatures to obtain 5-bromo-2-methoxy-pyrimidin-4-amine (III). Compound IV can, subsequently, be prepared from compound III using ethylacrylate in the presence of a suitable palladium catalyst system, for example palladium(II) acetate, an organic base like triethylamine or inorganic base like potassium carbonate, cesium carbonate or potassium phosphate in a suitable solvent system like combinations of dioxane and water or dimethylformamide. Reduction of the double bond and subsequent cyclisation can be accomplished by hydrogenation in the presence of a suitable catalyst system and solvent, for example palladium on charcoal in methanol to provide lactam V. Ethylester VI can be prepared from lactam V using [1-ethoxycarbonyl)cyclopropyl]tris(phenyl)phosphonium tetrafluoroborate in THF and a suitable base such as sodium hydride. Oxidation of VI can be accomplished using oxidizing reagents such as manganese-oxide or lead(IV) acetate to provide derivative VII. Compound VII can be converted to derivative IX, after appropriate deprotection with trimethylsilyliodide and subsequent conversion using phosphorus(V) oxychloride under heating conditions. Substitution of ethyl 2-chloro-5,6-dihydropyrimido[4,5-e]indolizine-7-carboxylate with $R^1NH_2$ can be carried out under acidic conditions using trifluoroacetic acid or concentrated hydrogen chloride solution and an appropriate solvent like n-butanol or isopropanol under microwave radiation. Alternatively, $R^1NH_2$ can be introduced in the presence of a suitable palladium catalyst system, for example palladium(II)acetate or tetrakis(triphenylphosphine)palladium(0) in the presence of an inorganic base such as potassium carbonate, cesium carbonate or potassium phosphate in a suitable solvent system like dioxane and water to generate derivative X. Finally conversion of derivative X to compounds with Formula I can be accomplished either first by saponification of the ester functionality in compound X and subsequent condensation to the amide, using methods well known in the art or through aminolysis of the ester functionality using a strong base such as lithium bis(trimethylsilyl)amide.

Pyrimido[4,5-e]indolizine compounds of Formula I, wherein $R^1$-$R^x$ have the previously defined meanings, can be prepared by the general synthetic route shown in scheme II.

Scheme II

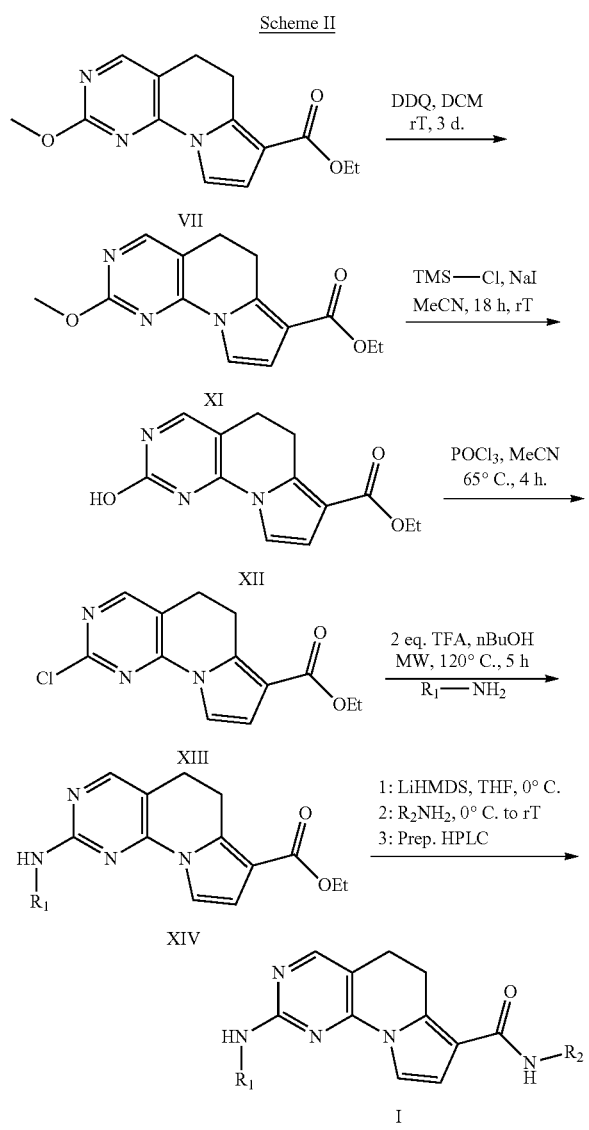

Oxidation of VII can be performed using oxidizing reagents like manganese-oxide, oxygen or DDQ to provide derivative XI. Compound XI can be converted to chloride XIII, after appropriate deprotection with trimethylsilyliodide and subsequent conversion using phosphorus(V) oxychloride under heating conditions. Substitution of ethyl 2-chloro-pyrimido[4,5-e]indolizine-7-carboxylate with $R^1NH_2$ can be carried out under acidic conditions using trifluoroacetic acid or concentrated hydrogen chloride solution and an appropriate solvent like n-butanol or isopropanol under microwave radiation. Alternatively, $R^1NH_2$ can be introduced in the presence of a suitable palladium catalyst system, for example palladium(II) acetate or tetrakis(triphenylphosphine)palladium(0) in the presence of an inorganic base such as potassium carbonate, cesium carbonate or potassium phosphate in a suitable solvent system like dioxane and water to generate derivative XIV. Finally, conversion of derivative XIV to compounds with Formula I can be accomplished either first by saponification of the ester functionality of compound XIV and subsequent condensation to the amide, using methods well known in the art, or through aminolysis of the ester functionality using a strong base such as lithium bis(trimethylsilyl)amide.

The invention is illustrated by the following examples.

EXAMPLES

The following examples are illustrative embodiments of the invention, not limiting the scope of the invention in any way. Reagents are either commercially available or are prepared according to procedures in the literature.

| | Method LCMS (A) | |
|---|---|---|
| Method name | NTRC_C18_Short.M | |
| Column | Waters XTerra C18-MS, 50 × 4.6 mm ID, 2.5 μm | |
| Flow | 0.5 ml/min. | |
| Temperature | 40° C. | |
| Detector DAD | 210, 254, 280 nm | |
| Detector MSD | API-ES | |
| MSD signal | 1 | 2 |
| Mode | Scan | Scan |
| Polarity | Positive | Negative |
| Mass Range | 100-1000 m/z | 100-1000 m/z |
| Fragmentor | 70 | 70 |
| Cycle Time | 50% | 50% |
| Sample preparation | N/A | |
| Concentration | 1 mg/ml in MeOH or ACN | |
| Injection volume | 1.0 μl | |
| Eluent | A | B |
| Time [min] | % 0.1% Formic Acid | % 0.05% Formic Acid in Acetonitrile |
| 0 | 90 | 10 |
| 0.3 | 90 | 10 |
| 7.0 | 10 | 90 |
| 7.1 | 90 | 10 |
| 10.0 | 90 | 10 |
| Post time | 0.2 min | Stop time  10 min |

| | Method LCMS (B) | |
|---|---|---|
| Method LCMS (B) Method name | NTRC_C18.M | |
| Column | Waters XTerra C18-MS, 50 × 4.6 mm ID, 2.5 μm | |
| Flow | 0.5 ml/min. | |

Method LCMS (B)

| | | |
|---|---|---|
| Temperature | 40° C. | |
| Detector DAD | 210, 254, 280 nm | |
| Detector MSD | API-ES | |

| MSD signal | 1 | 2 |
|---|---|---|
| Mode | Scan | Scan |
| Polarity | Positive | Negative |
| Mass Range | 100-1000 m/z | 100-1000 m/z |
| Fragmentor | 70 | 70 |
| Cycle Time | 50% | 50% |
| Sample preparation | N/A | |
| Concentration | 1 mg/ml in MeOH or ACN | |
| Injection volume | 1.0 μl | |

| Eluent Time [min] | A % 0.1% Formic Acid | B % 0.05% Formic Acid in Acetonitrile |
|---|---|---|
| 0 | 90 | 10 |
| 1 | 90 | 10 |
| 22.0 | 10 | 90 |
| 22.1 | 90 | 10 |
| 30.0 | 90 | 10 |

| Post time | 0.2 min | Stop time | 30 min |
|---|---|---|---|

Method LCMS (C)

| | |
|---|---|
| LC System | HP1200SL |
| Column | Agilent Eclipse plus C18 150 mm × 2.1 mm ID 3.5 μm |
| Column temperature | 40° C. |
| Sample(s) | ca 1 mg/mL |
| Autosampler temperature | 20° C. |
| Injection volume | 5 μL |
| Flow | 0.5 ml/min |
| Type of Pump | Binary |
| Eluent | A = MilliQ + 0.1% Formic Acid<br>B = Acetonitrile |

| Gradient | time (min) | % A | % B |
|---|---|---|---|
| | 0 | 90 | 10 |
| | 1 | 90 | 10 |
| | 22 | 10 | 90 |
| | 22.1 | 90 | 10 |
| | 30 | 90 | 10 |

| | |
|---|---|
| Next Injection delay | 0 min |
| UV detection | UV 210, 240, 280 nm |
| Flowcell DAD | 10 mm |
| MS system | Agilent 6130 single Quad MS |
| Source | ESI |
| Mode | Positive (+) |
| Mass range | 100-1000 Da |
| Flow | The total flow was split to a suitable flow infused directly in the APCI/ESI multimode source of the Agilent 6130 |

Method Preparative HPLC

| | |
|---|---|
| LC System | Waters Prep System |
| Column | Phenomenex Luna, C18(2) 100 A, 150 mm × 21.2 mm, 5 μm |
| Column Temp | 20° C. |
| Sample(s) | 10-50 mg |
| Autosamp. Temp | 20° C. |
| Injection volume | 500-950 μL |
| Flow | 15 ml/min |
| Eluent | A = MilliQ + MeCN (9/1)<br>B = Acetonitrile |

| Gradient | time (min) | % A | % B | % C |
|---|---|---|---|---|
| | 0 | 97 | 0 | 3 |
| | 20 | 37 | 60 | 3 |
| | 25 | 37 | 60 | 3 |
| | 25.1 | 97 | 0 | 3 |
| | 30 | 97 | 0 | 3 |

| UV detection | Photo Diode Array |
|---|---|

The following abbreviations are used throughout the application with respect to chemical terminology:
TFA Trifluoracetic acid
HATU O-(7-Azabenzotriazol-1-yl)-1,1,3,3-tetramethyluroniumhexafluorophosphate
DMF N,N-Dimethylformamide
THF Tetrahydrofuran
MeOH Methanol
EtOAc Ethyl acetate
DCM Dichloromethane
$Na_2SO_4$ Sodium sulfate
TMS-Cl Chlorotrimethylsilane
DiPEA N,N-Diisopropylethylamine
EtOH Ethanol
10% PD/C 10% Palladium on charcoal
HPLC High Performance Liquid Chromatography
LCMS Liquid Chromatography with Mass Spectrometry detection
NaOH Sodium hydroxide
HCl Hydrogen chloride
KOH Potassium hydroxide
$NaHCO_3$ Sodium bicarbonate
4-DMAP 4-Dimethylamino pyridine
Boc Butyloxycarbonyl
Cbz Benzyloxycarbonyl
$HNO_3$ Nitric acid
LiHMDS Lithium bis(trimethylsilyl)amide
DDQ 2,3-Dichloro-5,6-dicyano-p-benzoquinone
DBU 1,8-Diazabicyclo[5.4.0]under-7-ene
DEAD Diethyl azodicarboxylate The names of the final products in the examples are generated using Accelrys Draw (version 4.1).

Intermediate 1

Ethyl 2-chloro-5,6-dihydropyrimido[4,5-e]indolizine-7-carboxylate (a) 5-Bromo-2-chloro-pyrimidin-4-amine To a solution of 5-bromo-2,4-dichloro-pyrimidine (150 g; 658 mmol) in THF (445 mL) was added ammoniumhydroxide (25% in water, 250 mL) and the resulting reaction mixture was stirred at room temperature for 90 min. The mixture was subsequently evaporated to a small volume and partitioned between ethyl acetate and water. The organic phase was separated and washed with water and brine, dried over sodium sulfate, filtered and concentrated to give 137.3 g (quant. yield) of 5-bromo-2-chloro-pyrimidin-4-amine.

(b) 5-Bromo-2-methoxy-pyrimidin-4-amine

To a suspension of 5-bromo-2-chloro-pyrimidin-4-amine (137.3 g, 658 mmol) in methanol (1 L) was added portionwise sodium methoxide (83.5 g; 1.54 mol). The reaction mixture was stirred for 2 h. at reflux. The reaction mixture was concentrated to a small volume (~400 mL) and poured into a saturated solution of ammonium chloride in water (1.2 L). This mixture was allowed to stir for 15 min, after which the water layer was extracted with ethyl acetate. The combined ethyl acetate layers were washed with brine, dried over sodium sulfate, filtered and concentrated to yield 5-bromo-2-methoxypyrimidin-4-amine (133.7 g, 99.4%).

(c) Ethyl (E)-3-(4-amino-2-methoxy-pyrimidin-5-yl)prop-2-enoate

Palladium (II) acetate (1.21 g, 5.5 mmol) and triphenylphosphine (3.40 g, 13.0 mmol) were dissolved in anhydrous and oxygen-free DMF (53 mL) and stirred for 5 min at 30° C. to give an orange suspension. To this suspension was added a solution of 5-bromo-2-methoxypyrimidin-4-amine (44.1 g, 216 mmol) in DMF (270 mL), triethylamine (60.2 mL, 432 mmol) and a solution of ethyl acrylate (23.5 mL, 216 mmol) in DMF (50 mL). The reaction mixture was stirred at 100° C. o/n under a nitrogen atmosphere. The reaction mixture was evaporated to a small volume. Water (300 mL) and brine (300 mL) was added to the mixture, followed by an extraction with ethyl acetate (300 mL, twice). The combined organic layers were washed with water, brine, dried over sodium sulfate and concentrated in vacuo. The crude product was purified by silica column chromatography (ethyl acetate:heptane=2:1 v/v %) to yield the title compound (38.2 g, 77%).

(d) 2-Methoxy-6,8-dihydro-5H-pyrido[2,3-d]pyrimidin-7-one

To a stirred solution of ethyl (E)-3-(4-amino-2-methoxypyrimidin-5-yl)prop-2-enoate (12.52 g, 56.1 mmol) in methanol (250 mL) was added a suspension of 10% Pd on charcoal (1.19 g) in methanol/ethanol=3/1 v/v % (30 mL). The reaction mixture was stirred at room temperature for 15 min under nitrogen atmosphere. Then, ammonium formate (35.3 g, 561 mmol) was added and the resulting reaction mixture was refluxed o/n. After cooling of the reaction mixture, a fresh portion of ammonium formate (20 g, 317 mmol) was added and stirring was continued an additional night at reflux. The reaction mixture was filtered over Decalite® and the Pd-C/Decalite® residue was washed with dichloromethane/methanol=8/2 v/v % and the filtrate was concentrated in vacuo. The residue was dissolved in dichloromethane and washed with water, dried over sodium sulfate, filtered and concentrated in vacuo to obtain 9.4 g (94%) of 2-methoxy-6,8-dihydro-5H-pyrido[2,3-d]pyrimidin-7-one.

(e) Ethyl 2-methoxy-5,6,8,9-tetrahydropyrimido[4,5-e]indolizine-7-carboxylate 2-Methoxy-6,8-dihydro-5H-pyrido[2,3-d]pyrimidin-7-one (4.79 g, 26.8 mmol) was suspended in THF (200 mL) in a three-necked flask (500 mL), equipped with a mechanical stirred, a thermometer and a reflux condensor. The mixture was cooled to 0° C. and sodium hydride (60% dispersion in oil, 1.18 g, 29.4 mmol) was added in two batches. The mixture was stirred at 0° C. for 30 min. (1-ethoxycarbonylcyclopropyl)triphenylphosphonium tetrafluoroborate (13.6 g, 29.4 mmol) was added and the resulting suspension was heated to reflux and kept at reflux temperature for 3 days. The reaction mixture was cooled to room temperature and poured in a 1/1/1 mixture of brine/water/EtOAc (450 mL). The water layer was extracted with ethyl acetate (2×). The combined organic layers were washed with water and brine, dried over sodium sulfate, filtered and concentrated in vacuo to give 18.05 g of an orange oil. The crude product was used directly in the next step without purification.

(f) Ethyl 2-methoxy-5,6-dihydropyrimido[4,5-e]indolizine-7-carboxylate

To a stirred solution of ethyl 2-methoxy-5,6,8,9-tetrahydropyrimido[4,5-e]indolizine-7-carboxylate (18.05 g, 26.2 mmol) in dichloromethane (100 mL) was added acetic acid (3.15 g, 3 mL) and lead(IV) acetate (13.9 g, 31.4 mmol). The reaction mixture was stirred for 2 h at room temperature then filtered over a PE filter to remove Pb-salts and the Pb-residue was washed with 2×30 mL DCM. The filtrate was concentrated in vacuo and the resulting residue was dissolved in ethyl acetate (300 mL). A solution of sodium bicarbonate (5%) was added until pH~8.5. Both the organic and the water layers were filtered over Decalite® to remove any remaining salts. The water layer was subsequently extracted with EtOAc (2×50 mL). The combined organic layers were washed with 5% sodium bicarbonate-solution (100 mL), water (100 mL), bring (50 mL), dried ($Na_2SO_4$), filtered and concentrated in vacuo. The crude product was purified by column chromatography on silica (heptane:ethyl acetate=1/0 to 1/1 v/v 5) to yield the title compound (4.74 g, 66% over two steps).

(g) Ethyl 2-hydroxy-5,6-dihydropyrimido[4,5-e]indolizine-7-carboxylate

Sodium iodide (7.83 g, 52.2 mmol) was added to a stirred solution of ethyl 2-methoxy-5,6-dihydropyrimido[4,5-e]indolizine-7-carboxylate (4.74 g, 17.3 mmol) in acetonitril (150 mL). Trimethylsilyl chloride (5.64 g, 6.59 mL) dissolved in acetonitrile (30 mL) was added dropwise to the reaction mixture and the mixture was stirred at room temperature o/n. NaI (1 eq) was added and additional TMS-Cl (0.94 g, 1.1 mmol) in acetonitrile (6 mL) was added dropwise the reaction was suspended in 200 mL DCM/MeOH (4/1) and extracted with a mixture of saturated solution of sodium thiosulfate (200 mL) and water (200 mL). The water layer was extracted with 3×150 mL DCM/MeOH (4/1). The combined organic layers were dried over sodium sulfate, filtered and the solvent was removed under reduced pressure to give a yellow solid. The residue was dried at 40° C. under vacuum for 18 h to give 3.89 g ethyl 2-hydroxy-5,6-dihydropyrimido[4,5-e]indolizine-7-carboxylate (86%).

(h) Ethyl 2-chloro-5,6-dihydropyrimido[4,5-e]indolizine-7-carboxylate (Intermediate 1)

N,N-dimethylaniline (182 mg, 191 uL, 1.50 mmol) was added to a solution of ethyl 2-hydroxy-5,6-dihydropyrimido[4,5-e]indolizine-7-carboxylate (3.89 g, 15.0 mmol) in acetonitrile (100 mL). A solution of phosphorus(V) oxychloride (11.5 g, 7.00 mL, 75.0 mmol) in acetonitrile (15 mL) was added dropwise to the reaction mixture. The yellow suspension was heated for 4 hours to 65° C. during which the suspension turned into a clear solution. After cooling, the mixture was slowly poured in a stirred mixture of 25% aq. ammonia (200 mL, 86.7 eq.) and ice-water (250 mL) keeping the temperature below 10° C. in 15-20 minutes. After stirring for another 15 minutes the solids were filtered. The solids were dissolved in 200 mL EtOAc and washed with brine (20 mL). The organic layer was dried over sodium sulfate, and concentrated in vacuo to give an off-white solid. The crude product was purified by column chromatography on silica (heptane/ethyl acetate=1/0 to 1/1 v/v %) to yield the title compound (3.05 g, 73%).

Intermediate A

4-Amino-N-(2-hydroxy-2-methyl-propyl)-3-methoxy-benzamide (a) N-(2-hydroxy-2-methyl-propyl)-3-methoxy-4-nitro-benzamide A mixture of 3-methoxy-4-nitrobenzoic acid (1 g, 5.07 mmol), HATU (2.31 g, 6.1 mmol), and 1-amino-2-methyl-propan-2-ol (1.13 g, 12.7 mmol) in dichloromethane (20 mL) was stirred on an ice-cold water bath, and DiPEA (2.2 mL, 12.7 mmol) was added. After 10 min the mixture was allowed to warm to room temperature and stirred for 1 h. The mixture was diluted with ethyl acetate (100 mL) and subsequently washed with 5% sodium bicarbonate solution (3×75 mL), water and brine, dried over sodium sulfate and concentrated in vacuo to yield 1.47 g of crude N-(2-hydroxy-2-methyl-propyl)-3-methoxy-4-nitro-benzamide (quant.).

(b) 4-Amino-N-(2-hydroxy-2-methyl-propyl)-3-methoxy-benzamide (Intermediate A)

A solution of N-(2-hydroxy-2-methyl-propyl)-3-methoxy-4-nitro-benzamide (1.46 g 5.44 mmol) in EtOH (70 mL) was hydrogenated using an H-Cube continuous-flow reactor, 10% Pd/C, at 30° C., 1 bar, full $H_2$ modus, 1 mL/min. The resulting solution was concentrated in vacuo and the crude product was purified by column chromatography on silica (DCM/MeOH/25% $NH_3$=10/0/0 to 9/1/0 to 9/0.9/0.1 v/v %) to yield the title compound (775 mg, 60%).

Intermediate B

2-Methyl-4-(4-methylpiperazin-1-yl)aniline (a) 1-Methyl-4-(3-methyl-4-nitro-phenyl)piperazine N-methylpiperazine (752 µL, 6.79 mmol) was added to 4-fluoro-2-methyl-1-nitro-benzene (527 mg, 3.39 mmol) and the resulting mixture was stirred at room temperature for 18 h. Water was added to the reaction mixture and extraction performed with ethyl acetate. The combined organic layers were washed with brine, dried over sodium sulfate and concentrated in vacuo. The crude product was purified by silica column chromatography (DCM/MeOH=1.0 to 9/1 v/v %) to yield the title compound (786 mg, 98%).

(b) 2-Methyl-4-(4-methylpiperazin-1-yl)aniline (Intermediate B)

To a stirred solution of 1-methyl-4-(3-methyl-4-nitro-phenyl)piperazine (393 mg, 1.67 mmol) in ethanol (10 mL) was added a suspension of 10% Pd on charcoal (35 mg) in ethanol (6 mL). The reaction mixture was stirred at room temperature for 15 min under a nitrogen atmosphere. Then, ammonium formate (1.05 g; 16.7 mmol) was added and the reaction mixture was heated to reflux temperature for 15 min. The reaction mixture was cooled, filtered over Decalite® and concentrated in vacuo. The residue was dissolved in dichloromethane and washed with a saturated solution of sodium bicarbonate. The organic layer was dried over sodium sulfate, filtered and concentrated in vacuo to obtain 268 mg (78%) of 2-methyl-4-(4-methylpiperazin-1-yl)aniline.

Intermediate 2

2-[2-Methyl-4-(4-methylpiperazin-1-yl)anilino]-5,6-dihydropyrimido[4,5-e]indolizine-7-carbonyl chloride (a) Ethyl 2-[2-methyl-4-(4-methylpiperazin-1-yl)anilino]-5,6-dihydropyrimido[4,5-e]indolizine-7-carboxylate To a suspension of ethyl 2-chloro-5,6-dihydropyrimido[4,5-e]indolizine-7-carboxylate (Intermediate 1, 381 mg, 1.37 mmol) in n-butanol (11 mL) was added 2-methyl-4-(4-methylpiperazin-1-yl)aniline (Intermediate B, 268 mg, 1.3 mmol) and trifluoroacetic acid (200 µL; 2.6 mmol). The reaction mixture was heated to for 12 hours at 120° C. under microwave radiation. The reaction mixture was concentrated in vacuo and the residue was dissolved in ethyl acetate. The organic layer was washed with a saturated solution of sodium bicarbonate, dried over sodium sulfate, filtered and concentrated in vacuo. The residue was purified by preparative HPLC. Fractions containing product were collected and evaporated to afford ethyl 2-[2-methyl-4-(4-methylpiperazin-1-yl)anilino]-5,6-dihydropyrimido[4,5-e]indolizine-7-carboxylate (211 mg, 34% yield).

(b) 2-[2-Methyl-4-(4-methylpiperazin-1-yl)anilino]-b,6-dihydropyrimido[4,5-e]indolizine-7-carbonyl chloride (Intermediate 2)

To a solution of ethyl 2-[2-methyl-4-(4-methylpiperazin-1-yl)anilino]-5,6-dihydropyrimido[4,5-e]indolizine-7-carboxylate (211 mg, 0.47 mmol) in 8 mL absolute ethanol was added a 2M NaOH-solution (591 µL (2.5 eq). 1.18 mmol). The reaction mixture was heated at 65° C. o/n. Reaction mixture was evaporated to dryness and dried under high vacuum. The resulting residue was dissolved in water, stirred o/n at room temperature and lyophilised to yield the crude title compound.

Thionyl chloride (682 µL, 9.4 mmol) was added to a cold (0° C.) suspension of the crude sodium 2-[2-methyl-4-(4-methylpiperazin-1-yl)anilino]-b,6-dihydropyrimido[4,5-e]indolizine-7-carboxylate (242 mg, 0.47 mmol theor.) in dichloromethane (10 mL). The resulting slurry was stirred at room temperature o/n. The reaction mixture was concentrated in vacuo and the residue was co-evaporated with toluene (2×10 mL) to give of 2-[2-methyl-4-(4-methylpiperazin-1-yl)anilino]-5,6-dihydropyrimido[4,5-e]indolizine-7-carbonyl chloride as a yellow/brown powder (354 mg, quant. crude yield).

Intermediate C

2-Methoxy-4-morpholino-aniline

This compound was prepared in an analogous manner as described in Intermediate B-a starting from morpholine and 4-fluoro-2-methoxy-1-nitro-benzene (1.3 g, 95%). The thus obtained 4-(3-methoxy-4-nitro-phenyl)morpholine (1.3 g, 5.46 mmol) was dissolved in THF (45 mL) and acetic acid (5 mL) was added. The mixture was cooled to 0° C. and zinc (7.09 g, 109 mmol) was added in small portions to keep the temperature below 20° C. The reaction mixture was stirred at room temperature o/n. After TLC analysis indicated a complete conversion the starting material, the mixture was filtered over Decalite®0 and the Zn-Decalite® residue was washed with EtOAc (20 mL). The combined filtrates were washed with a 1N NaOH-solution (25 mL), followed by water (25 mL) and brine (25 mL). The organic layer was dried ($Na_2SO_4$), filtered and concentrated in vacuo to give 2-methoxy-4-morpholino-aniline (1.05 g, 92%).

Intermediate D

2-Methyl-6-morpholino-pyridin-3-amine

This compound was prepared in an analogous manner as described for Intermediate B, starting from morpholine and 6-chloro-3-nitro-2-picoline to afford the title compound (156.9 mg, 82%).

Intermediate E

2-Chloro-4-(4-methylpiperazin-1-yl)aniline (a) tert-Butyl N-(4-bromo-2-chloro-phenyl)-N-tert-butoxycarbonyl-carbamate To a solution of 4-bromo-2-chloroaniline (3.0 g, 14.52 mmol) and potassium carbonate (6 g, 43.6 mmol) in DMF (100 mL) was added di-tert-butyl dicarbonate (1.8 g, 28.3 mmol). The reaction mixture was stirred at room temperature for 48 h, after which the mixture was poured into water/brine and extracted with ethyl acetate (3×50 mL). The combined organic layers were washed with brine (3×50 mL), dried over sodium sulfate, filtered and concentrated under reduced pressure. The residue was purified by column chromatography (EtOAc/heptane=1/9 v/v %) to afford tert-butyl-(4-bromo-2-chloro-phenyl)-N-tert-butoxycarbonyl-carbamate (2.5 g, 42.3%) as a yellow/orange oil.

(b) tert-Butyl N-tert-butoxycarbonyl-N-[2-chloro-4-(4-methylpiperazin-1-yl)phenyl]carbamate A mixture of tert-butyl N-(4-bromo-2-chloro-phenyl)-N-tert-butoxycarbonyl-carbamate (500 mg, 1.23 mmol), 1-methylpiperrazone (166 µL, 1.48 mmol), palladium(II) acetate (27.6 mg, 0.12 mmol), (+/−)-2,2'-bis(diphenylphosphino)-1,1'-binaphthyl (119 mg, 0.20 mmol) and cesium carbonate (1.2 g, 3.69 mmol) in toluene (20 mL) was heated at 100° C. for 16 hours under a nitrogen atmosphere. After cooling to ambient temperature, the mixture was concentrated and the residue was diluted with dichloromethane, washed with water and brine, dried over sodium sulfate, filtered and concentrated in vacuo. The residue was purified by column chromatography (dichloromethane/methanol=100/0 to 95/5 v/v %) to afford tert-butyl N-tert-butoxycarbonyl-N-[2-chloro-4-methylpiperazin-1-yl)phenyl]carbamate (480 mg, 91.6%).

(c) 2-Chloro-4-(4-methylpiperazin-1-yl)aniline (Intermediate E)

tert-Butyl N-tert-butoxycarbonyl-N-[2-chloro-4-methyl-piperazin-1-yl)phenyl]carbamate (260 mg; 0.61 mmol) was dissolved in DCM (4 mL). TFA (4 mL) was added and the reaction mixture was stirred for 1 hour at room temperature. The mixture was concentrated and the residue was dissolved in DCM (10 mL) and poured into a 5% sodium bicarbonate solution (10 mL). The water layer was extracted with DCM (2×10 mL). The combined organic layers were filtered over a PE-filter and concentrated in vacuo to give a brown oil (105 mg, 76%) that was used without further purification.

Intermediate F

2-Methoxy-4-(4-methylpiperazin-1-yl)aniline

This compound was prepared in an analogous manner as described for Intermediate B, starting from N-methylpiperazine and 2-methoxy-4-fluoronitroenzene to afford the title compound (1.38 g, 94%).

Intermediate G

2-Ethoxy-4-(4-methylpiperazin-1-yl)aniline (a) 2-Ethoxy-4-fluoro-1-nitro-benzene To a cold (0° C.) mixture of ethanol (0.735 mL, 12.6 mmol) in THF (15 mL) was added sodium hydride (60% dispersion in mineral oil, 553 mg, 13.83 mmol). The reaction mixture was stirred at 0° C. for 15 min, after which a solution of 2,4-difluoro-1-nitrobenzene (1.38 mL, 12.6 mmol) in THF (25 mL) was added dropwise. After stirring for an additional 90 min at room temperature, the reaction was quenched with water and brine, dried over sodium sulfate and concentrated in vacuo. The residue was purified by column chromatography (heptane/ethyl acetate=100/0 to 85/15 v/v %) to afford 2-ethoxy-4-fluoro-1-nitro-benzene (2.15 g, 92%)

(b) 1-(3-Ethoxy-4-nitro-phenyl)-4-methyl-piperazine

N-Methylpiperazine (603 µL, 5.44 mmol) was added to 2-ethoxy-4-fluoro-1-nitro-benzene (500 mg, 2.7 mmol) and the resulting mixture was stirred at room temperature for 18 hours. Water was added to the reaction mixture and subsequently extracted with ethyl acetate. The combined organic layers were washed with brine, dried over sodium sulfate and concentrated in vacuo. The crude product was purified by column chromatography on silica (DCM/MeOH=10/0 to 9/1 v/v %) to yield the title compound (646 mg, 90%).

(c) 2-Ethoxy-4-(4-methylpiperazin-1-yl)aniline (Intermediate G)

To a stirred solution of 1-(3-ethoxy-4-nitro-phenyl)-4-methyl-piperazine (265 mg, 1.0 mmol) in ethanol (5 mL) was added a suspension of 10% Pd on charcoal (22 mg) in ethanol (6 mL). The reaction mixture was stirred at room temperature for 15 min under a nitrogen atmosphere. Ammonium formate (630 mg; 10.0 mmol) was added and the resulting reaction mixture was heated at reflux temperature for 15 min. The reaction mixture was cooled and filtered over Decalite®. The filtrate was concentrated in vacuo and the residue was subsequently dissolved in dichloromethane, washed with saturated solution of sodium bicarbonate, dried over sodium sulfate, filtered and concentrated in vacuo to obtain 231 mg (98%) of 2-ethoxy-4-(4-methylpiperazin-1-yl)aniline.

Intermediate H

Tert-Butyl 4-(4-amino-3-methoxy-phenyl)piperazine-1-carboxylate

This compound was prepared in an analogous manner as described in Intermediate B, starting from tert-butyl piperazine-1-carboxylate and 2-methoxy-4-fluoronitrobenzene to afford the title compound (245 mg, 91%).

Intermediate I

Benzyl 4-(4-amino-3-methyl-phenyl)piperazine-1-carboxylate

This compound was prepared in an analogous manner as described in Intermediate C, starting from benzyl piperazine-1-carboxylate and 4-fluoro-2-methyl-1-nitro-benzene to afford the title compound (327 mg, quantitative).

Intermediate J 2-(Difluoromethoxy)-4-(4-methylpiperazin-1-yl)aniline

To a solution of 5-fluoro-2-nitro-phenol (500 mg, 3.18 mmol) in DMF (6 ml) was added sodium 2-chloro-2,2-difluoro-acetate (970 mg, 6.36 mmol) and disodium carbonate (405 mg, 3.82 mmol). The reaction mixture was stirred at 100° C. for 3.5 hours and subsequently at room temperature for 3 days. A 4M HCl-solution was added until a clear solution was obtained with water and extracted with EtOAc. The combined organic layers were washed with 1M NaOH-solution, brine, dried over sodium sulphate, filtered and concentrated in vacuo. The residue was purified by column chromatography (heptane/ethyl acetate=10/0 to 8/2 v/v %) to afford 2-(difluoromethoxy)-4-fluoro-1-nitro-benzene (493 mg, 75%).

The title compound was prepared in an analogous manner as described for Intermediate B, starting from N-methylpiperazine and 2-(difluoromethoxy)-4-fluoro-1-nitro-benzene to afford 180 mg (80%).

Intermediate K

4-Methyl-6-morpholino-pyridin-3-amine

This compound was prepared in an analogous manner as described in Intermediate B, starting from morpholine and 2-chloro-5-nitro-4-picoline to afford the title compound (122.9 mg, 81.5%)

Intermediate L

4-Amino-3-methoxy-N-(1-methyl-4-piperidyl)benzamide

This compound was prepared in an analogous manner as described for Intermediate A, starting from 4-amino-1-methylpiperidine and 3-methoxy-4-nitrobenzoic acid to afford the title compound (980 mg, 82%)

Intermediate M

4-Amino-3-methyl-N-(1-methyl-4-piperidyl)benzamide

This compound was prepared in an analogous manner as described for Intermediate A-a, starting from 4-amino-1-methylpiperidine and 4-amino-3-methylbenzoic acid to afford the title compound (700 mg, 70%).

Intermediate N

4-Amino-3-chloro-N-(1-methyl-4-piperidyl)benzamide

This compound was prepared in an analogous manner as described for Intermediate A-a, starting from 4-amino-1-methylpiperidine and 4-amino-3-chlorobenzoic acid to afford the title compound (1.64 g, quant.).

Intermediate O

4-Amino-3-fluoro-N-(1-methyl-4-piperidyl)benzamide

This compound was prepared in an analogous manner as described for Intermediate A-a, starting from 4-amino-1-methylpiperidine and 4-amino-3-fluorobenzoic acid to afford the title compound (170 mg, 16%).

Intermediate P

4-Amino-3-ethoxy-N-(1-methyl-4-piperidyl)benzamide (a) 3-Ethoxy-4-nitro-benzoic acid 3-Fluoro-4-nitrobenzoic acid (1.50 g, 8.11 mmol) and potassium hydroxide (1.05 g, 18.6 mmol) were stirred in ethanol (25 mL) at room temperature. The resulting suspension was slowly heated to reflux (10 minutes) during which the reaction mixture turned into a deep red solution. After 10 minutes of heating at reflux, and under vigorous stirring a thick solid precipitated. The reaction mixture was cooled to room temperature and water (10 mL) was added. Next, 2M HCl-solution (9.3 mL) was added until pH<2. The resulting precipitate was vigorously stirred, filtered and the residue was washed with water (2×10 mL). The residue was dried at 40° C. under vacuum to give 1.53 g 3-ethoxy-4-nitro-benzoic acid (89%).

(b) 4-Amino-3-ethoxy-N-(1-methyl-4-piperidyl)benzamide (Intermediate P)

The title compound was prepared in an analogous manner as described for Intermediate A, starting from 4-amino-1-methylpiperidine and 3-ethoxy-4-nitrobenzoic acid to give 190 mg 4-amino-3-ethoxy-N-(1-methyl-4-piperidyl)benzamide (70%).

Intermediate Q

4-Amino-3-(difluoromethoxy)-N-(1-methyl-4-piperidyl)benzamide

This compound was prepared in an analogous manner as described for Intermediate A-a, starting from 4-amino-1-methylpiperidine and 4-amino-3-(difluoromethoxy)benzoate to afford the title compound (130 mg, 29.5%).

Intermediate R

2-Methoxy-4-(1,3,5-trimethylpyrazol-4-yl)aniline (a) tert-Butyl-N-[2-methoxy-4-(1,3,5-trimethylpyrazol-4-yl)phenyl]carbamate A mixture of tert-butyl N-(4-bromo-2-methoxy-phenyl)carbamade (150 mg, 0.5 mmol), 1,3,5-trimethyl-4-(4,4,5,5- tetramethyl-1,3,2-dioxaborolan-2-yl)pyrazole (118 mg, 0.5 mmol), tetrakis(tri-phenylphosphine)palladium (0) (58 mg, 0.05 mmol) and potassium carbonate (207 mg, 1.5 mmol) in dioxane (4 mL) was heated at 100° C. under microwave irradiation for 20 minutes in a sealed tube. After cooling to ambient temperature, the mixture was concentrated and the residue was diluted with ethyl acetate, washed with water and brine, dried over sodium sulfate, filtered and concentrated in vacuo. The residue was purified by column chromatography (heptane/ethyl acetate=100/0 to 25/75 v/v %) to afford tert-butyl N-[2-methoxy-4-(1,3,5-trimethylpyrazol-4-yl)phenyl]carbamate (126.8 mg, 77%).

(b) 2-Methoxy-4-(1,3,5-trimethylpyrazol-4-yl)aniline (Intermediate R)

tert-Butyl N-[2-methoxy-4-(1,3,5-trimethylpyrazol-4-yl)phenyl]carbamade (127 mg, 0.38 mmol) was dissolved in DCM (2 mL). TFA (3 mL) was added and the reaction mixture was stirred for 1 hour at room temperature. The mixture was concentrated in vacuo to give a brown oil (313 mg) that was used without further purification.

Intermediate S

2-Methoxy-4-[(1-methyl-4-piperidyl)oxy]aniline (a) 4-(3-Methoxy-4-nitro-phenoxy)-1-methyl-piperidine To a solution of 4-fluoro-2-methoxy-1-nitro-benzene (750 mg, 4.38 mmol) in toluene (10 mL) were added 10 mL of a 25% KOH-solution, 4-hydroxy-N-methylpiperidine (1009 mg, 8.76 mmol) and tetra-n-butyl ammonium bromide (282 mg, 0.876 mmol). The mixture was heated at 60° C. o/n. The reaction mixture was then diluted with ethyl acetate and the water layer was extracted with ethyl acetate. The combined organic layers were washed with brine, dried over sodium sulfate and evaporated. The residue was purified by flash chromatography on silica gel (dichloromethane/methanol=99/1 to 9/1 v/v %) to obtain the title compound. (650 mg, 55.7%)

(b) 2-Methoxy-4-[(1-methyl-4-piperidyl)oxy]aniline (Intermediate S)

10% Pd/C (20 mg) was added as a suspension in ethanol to a solution of 4-(3-methoxy-4-nitro-phenoxy)-1-methyl-piperidine (200 mg, 0.75 mmol) in ethanol (5 mL). The resulting mixture was stirred for 15 min at room temperature. Ammonium formate (473 mg, 7.5 mmol) was added and the reaction mixture was stirred for 1 hour at reflux under nitrogen atmosphere. The reaction mixture was cooled to room temperature and filtered over Decalite®. The filtrate was concentrated in vacuo, after which dichloromethane was added and the organic phase was washed with 5% solution of NaHCO$_3$. The organic phase was dried over sodium sulfate, filtered and concentrated in vacuo to yield 2-methoxy-4-[(1-methyl-4-piperidyl)oxy]aniline (169.5 mg, 95.6%).

Intermediate T

2-Methyl-4-[(1-methyl-4-piperidyl)oxy]aniline

This compound was prepared in an analogous manner as described for Intermediate S, starting from 1-methylpiperidin-4-ol and 4-fluoro-2-methyl-1-nitro-benzene to afford the title compound (151.7 mg, 81%).

Intermediate U 4-(2-Dimethylaminoethyloxy)-2-methoxy-aniline (a) 2-(3-methoxy-4-nitro-phenoxy)-N,N-dimethyl-ethanamine To a cold (0° C.) solution of N,N-dimethylethanolamine (651 µL, 6.43 mmol) in THF (5 was added NaH (60% dispersion in mineral oil, 385 mg) portionwise. The suspension was stirred for an additional 30 min, then 4-fluoro-2-methoxy1-nitro-benzene (1 g, 5.84 mmol) in 5 mL of dry THF was added dropwise. The solution was refluxed o/n. The solvent was removed under vacuum and the residue was partitioned between ethyl acetate and water (50 mL each). The organic layer was collected and the aqueous layer was subsequently extracted with ethyl acetate. The combined organic layers were washed with 1M HCl-solution, water, 5%-sodium bicarbonate solution and brine. The organic layer was dried over sodium sulphate and evaporated. The residue was purified by flash chromatography on silica gel in (heptane/ethyl acetate=9/1 to 1/1 v/v %) as eluent to obtain the title compound. (720 mg, 51.3%)

(b) 4-(2-Dimethylaminoethyloxy)-2-methoxy-aniline (Intermediate U)

This compound was prepared in an analogous manner as described for Intermediate Sb to afford the title compound (144.8 mg, 68.9%)

Intermediate V

4-Amino-N-(1-methyl-4-piperidyl)benzamide

This compound was prepared in an analogous manner as described for Intermediate A-a starting from 4-amino-1-methylpiperidine and 4-amino-benzoic acid to afford the title compound (170 mg, 16%).

Intermediate W

2-Methyl-4-morpholino-aniline

This compound was prepared in an analogous manner as described for Intermediate C, starting from morpholine and 5-fluoro-2-nitrololuene to afford the title compound (8.77 g, 92%).

Intermediate X

2-Isopropoxy-4-(4-methylpiperazin-1-yl)aniline

The title compound was prepared in an analogous manner as described for Intermediate G, starting from 1-methylpiperazine and 4-fluoro-2-isopropoxy-1-nitro-benzene to give 2-isopropoxy-4-(4-methylpiperazin-1-yl)aniline (337 mg, 50%).

Intermediate Y

2-Methoxy-4-(1-methylpyrrolidin-3-yl)oxy-aniline

This compound was prepared in an analogous manner as described for Intermediate U, starting from 1-methylpyrrolidin-3-ol and 4-fluoro-2-methoxy-1-nitro-benzene to afford the title compound (199 mg, 84%).

Intermediate Z

Benzyl 3-(4-amino-3-methyl-phenoxy)azetidine-1-carboxylate (a) tert-Butyl 3-(3-methyl-4-nitro-phenoxy)azetidine-1-carboxylate To a cold (0° C.) solution of N-Boc-3-hydroxy-azetidine (1.84 g, 10.6 mmol) in THF (10 mL) was added NaH (60% dispersion in mineral oil, 382 mg) portion wise. The suspension was stirred for an additional 30 min, then 2-nitro-5-fluorotoluene (1.5 g, 9.79 mmol) in 10 mL of dry THF was added drop wise. The solution was stirred at room temperature o/n. Solvent was removed under vacuum and the residue was partitioned between ethyl acetate and water (50 mL each). The organic layer was collected and the aqueous layer was subsequently extracted with ethyl acetate. The combined organic layers were washed with 1M HCl-solution, water, 5%-sodium bicarbonate solution and brine. The organic layer was dried over sodium sulphate and concentrated in vacuo. The residue was purified by column chromatography (heptane/ethyl acetate=9/1 to 1/1 v/v %) to obtain 2.24 g (75.1%) of the title compound.

(b) Benzyl 3-(3-methyl-4-nitro-phenoxy)azetidine-1-carboxylate

To a solution of tert-Butyl 3-(3-methyl-4-nitro-phenoxy)azetidine-1-carboxylate 92.24 g, 7.3 mmol) in DCM (20 mL) was added a 4N solution of HCl in dioxane (9.1 mL) and the reaction mixture was stirred for 3 h at room temperature. The mixture was concentrated in vacuo and the residue was twice co-evaporated with ethanol to give the deprotected compound (1.7 g, 95%) that was used without further purification. To a stirred suspension of crude 3-(3-methyl-4-nitro-phenoxy)azetidine hydrochloride (1.7 g, 7.97 mmol) in DCM (25 mL) was added triethylamine (2.8 mL, 20 mmol). N-(benzyloxycarbonyloxy)-succinimide 92.19 g; 8.77 mmol) was added to the reaction mixture and the mixture was stirred for 30 min at room temperature. 5% sodium bicarbonate solution was extracted with dichloromethane. The combined organic layers were dried (Na$_2$SO$_4$), filtered and solvent was evaporated. The residue was purified by column chromatography (heptane/ethyl acetate=100/0 to 50/50 v/v %) to obtain 2.17 g (80%) of benzyl 3-(3-methyl-4-nitro-phenoxy)azetidine-1-carboxylate.

(c) Benzyl 3-(4-amino-3-methyl-phenoxy)azetidine-1-carboxylate (Intermediate Z)

This compound was prepared in an analogous manner as described for Intermediate C, starting form benzyl 3-(3-methyl-4-nitro-phenoxy)azetidine-1-carboxylate to afford the title compound (145.3 mg, 39%).

Intermediate ZA 4-(3,5-Dimethylisoxazol-4-yl)-2-methoxy-aniline

This compound was prepared in an analogous manner as described for Intermediate R, starting from tert-butyl N-(4-bromo-2-methoxy-phenyl)carbamate and 3,5-dimethyl-4-(4,5,5-tetramethyl-1,3,2-dioxaborolan-2-yl)isoxazole to afford the title compound (96 mg).

Intermediate ZB

Benzyl 3-(4-amino-3-methoxy-phenoxy)azetidine-1-carboxylate

This compound was prepared in an analogous manner as described for Intermediate Z, starting from 4-fluoro-2-methoxy-1-nitro-benzene and N-Boc-3-hydroxy-azetidine to afford the title compound (215.1 mg, 55%).

Intermediate ZC 4-(4-Methylpiperazin-1-yl)-2-(trideuteriomethoxy)aniline (a) 4-Fluoro-1-nitro-2-(trideuteriomethoxy)benzene To a solution of 5-fluoro-2-nitrophenol 91.5 g, 9.55 mmol) in acetone (20 mL) was added K$_2$CO$_3$ (2.31 g, 16.7 mmol) at room temperature. To the resulting suspension was added deuterated iodomethane (0.71 mL, 11.46 mmol) and the reaction mixture was stirred at reflux o/n. After concentration of the reaction mixture, the residue was partitioned between water and ethyl acetate. The ethyl acetate layer was washed with water, brine, dried over sodium sulfate and evaporated in vacuo to afford of 4-fluoro-1-nitro-2-(trideuteriomethoxy)benzene (1.67 g, 100%).

(b) 1-Methyl-4-[4-nitro-3-(trideuteriomethoxy)phenyl]piperazine

4-Fluoro-1-nitro-2-(trideuteriomethoxy)benzene (1.67 g, 9.55 mmol) and N-methylpiperazine (2.12 mL, 19.1 mmol) were combined in THF (1 mL) and stirred for 18 h. at room temperature. The yellow precipitate formed after addition of water was filtered, washed with water and dried in vacuo to afford of 1-methyl-4-[4-nitro-3-(trideuteriomethoxy)phenyl]piperazine (1.67 g, 80.7%).

(c) 4-(4-Methylpiperazin-1-yl)-2-(trideuteriomethoxy)aniline (Intermediate ZC)

This compound was prepared in an analogous manner as described for Intermediate B step b, starting from 1-methyl-4-[4-nitro-3-(trideuteriomethoxy)phenyl]piperazine to afford the title compound (177.8 mg).

Intermediate ZD

2-Methyl-6-(4-methylpiperazin-1-yl)pyridin-3-amine

This compound was prepared in an analogous manner as described for Intermediate B, starting from N-methylpiperazine and 6-chloro-3-nitro-2-picoline to afford the title compound (188.9 mg, 92%).

Intermediate ZE

Benzyl 4-(4-amino-3-methoxy-phenyl)piperazine-1-carboxylate

This compound was prepared in an analogous manner as described for Intermediate B-a, starting from enzyl piperazine-1-carboxylate and 2-methoxy-4-fluoronitroenzene.

After reduction using the procedure described for Intermediate C, the title compound was obtained (1.2 g, 95%).

Intermediate ZF

4-Methoxy-2-(4-methylpiperazin-1-yl)pyrimidin-5-amine (a) 2-Chloro-4-methoxy-5-nitro-pyrimidine To a solution of 2,4-dichloro-5-nitro-pyrimidine (1.00 g; 5.2 mmol) in methanol (30 mL) was added dropwise a solution of sodium methoxide (278 mg, 5.2 mmol) in methanol (5 mL) at −10° C. The reaction mixture was stirred for 10 minutes at −10° C. Acetic acid (5 mL) was added and the mixture was allowed to warm to room temperature. After evaporation of the mixture, the residue was partitioned between 5% NaHCO$_3$-solution and ethyl acetate. The ethyl acetate layer was washed with water, brine, dried over sodium sulfate and evaporated in vacuo. The residue was purified by column chromatography (heptane/ethyl acetate=4/1 v/v %) to obtain 281.9 mg (29%) of 2-chloro-4-methoxy-5-nitro-pyrimidine.

(b) 4-Methoxy-2-(4-methylpiperazin-1-yl)pyrimidin-5-amine (Intermediate ZF)

This compound was prepared in an analogous manner as described for Intermediate B step b, starting from 2-chloro-4-methoxy-5-nitro-pyrimidine and N-methylpiperazine to afford the title compound (212.8 mg, 89%).

Intermediate ZG

2-Methoxy-5-methyl-4-(4-methylpiperazin-1-yl)aniline

This compound was prepared in an analogous manner as described for Intermediate B, starting from N-methylpiperazine and 5-fluoro-4-methyl-2-nitroanisole to afford the title compound (94.4 mg, quant).

Intermediate ZH

Benzyl 4-(4-amino-3-methoxy-phenyl)-2-methyl-piperazine-1-carboxylate

This compound was prepared in an analogous manner as described for Intermediate B-a, starting from benzyl 2-methylpiperazine-1-carboxylate and 2-methoxy-4-fluoronitroenzene. After reduction using the procedure described for Intermediate C, the title compound was obtained (295.4 mg, 97%).

Intermediate ZI

N4-[3-(dimethylamino)propyl]-2-methoxy-N4-methyl-benzene-1,4-diamine

This compound was prepared in an analogous manner as described for Intermediate B, starting from N,N',N'-trimethylpropane-1,3-diamine and 4-fluoro-2-methoxy-1-nitro-benzene to afford the title compound (148.8 mg, 94%).

Intermediate ZJ 2-methoxy-4-(2-methoxyethoxy)aniline

This compound was prepared in an analogous manner as described for Intermediate S, starting from 2-methoxyethanol and 4-fluoro-2-methoxy-1-nitro-benzene to afford the title compound (113.4 mg, quant.).

Intermediate Aa 1-(2-Methoxyethyl)-3,5-dimethylpyrazol-4-amine (a) 1-(2-Methoxyethyl)-3,5-dimethyl-4-nitro-pyrazole To a solution of 3,5-dimethyl-4-nitro-1H-pyrazole 92.5 g, 17.7 mmol) and cesium carbonate (6.06 g, 18.6 mmol) in DMF (50 mL) was added 2-bromoethyl methyl ether (2.59 g, 1.75 mL, 18.6 mmol). The mixture was heated at 100° C. for 3.5 h. After cooling to room temperature, the mixture was poured into water and extracted with ethyl acetate (3×50 mL). The combined organic layers were washed with brine (50 mL), dried over sodium sulfate, filtered and concentrated under reduced pressure. The residue was purified by column chromatography (EtOAc/heptanes=1/4 v/v %) to afford 1-(2-methoxyethyl)3,5-dimethyl-4-nitro-pyrazole (2.66 g, 75.4%) as a white crystalline solid.

(b) 1-(2-Methoxyethyl)-3,5-dimethyl-pyrazol-4-amine 1-(2-Methoxyethyl)-3,5-dimethyl-4-nitro-pyrazole (245 mg, 1.22 mmol) was dissolved in methanol (25 mL). The resulting solution was hydrogenated using a H-Cube continuous-flow hydrogenation reactor, 10% Pd/C, at 30° C., 8-10 bar, 1 mL/min, full H$_2$ modus. The resulting solution was concentrated in vacuo to yield 208 mg (quant. yield) of the title compound as a light-brown oil.

Intermediate Ab 3,5-Dimethyl-1H-pyrazol-4-amine

This compound was prepared in an analogous manner as described for Intermediate Aa-b, starting from 3,5-dimethyl-4-nitro-1H-pyrazol to give 110 mg 3,5-dimethyl-1H-pyrazol-4-amine (quant.).

Intermediate Ac 3,5-Diethyl-1H-pyrazol-4-amine (a) 3,5-Diethyl-1H-pyrazole

To a solution of 3,5-heptanedione (2 g, 15.6 mmol) and hydrazine hydrate (0.77 g, 15.8 mmol) in water (10 mL) was added acetic acid (1 drop) and the reaction mixture was heated to reflux for 1 h. The reaction mixture was then cooled, and concentrated under reduced pressure to provide 1.8 g of the title compound. This compound was used directly in the next step without purification.

(b) 3,5-Diethyl-4-nitro-1H-pyrazol

To a cold (0° C.) mixture of 3,5-diethyl-1H-pyrazole (1.8 g, 14.5 mmol) and concentrated sulphuric acid (1.5 ml) was added slowly, under vigorous stirring, fuming HNO$_3$ (4.35 ml). The reaction mixture was stirred overnight at 60° C. The mixture was subsequently cooled to room temperature, then carefully added to an ice-cold saturated solution of sodium bicarbonate and stirred for 15 min. The mixture was then extracted three times with EtOAc and combined organic layers were washed with brine, dried over sodium sulphate, filtered and evaporated in vacuo to give: 2.52 g 3,5-diethyl-4-nitro-1H-pyrazole.

(c) 3,5-Diethyl-1H-pyrazol-4-amine (Intermediate Ac)

The title compound was prepared in an analogous manner as described for Intermediate Aa-b, starting from 3,5-diethyl-4-nitro-1H-pyrazole to give 3,5-diethyl-1H-pyrazol-4-amine (174 mg, 71%).

Intermediate Ad

5-Chloro-1,3-dimethyl-pyrazol-4-amine (a) 5-Chloro-1,3-dimethyl-4-nitro-pyrazole To a cold (0° C.) mixture of 5-chloro-1,3-dimethyl-pyrazole (1 g, 7.66 mmol) and concentrated sulphuric acid (750 µl) was added slowly, under vigorous stirring, fuming $HNO_3$ (2.1 mL). The reaction mixture was stirred overnight at 60° C. The mixture was subsequently cooled to room temperature, then carefully added to an ice-cold saturated solution of sodium bicarbonate and stirred for 15 min. The mixture was then extracted three times with EtOAc and combined organic layers were washed with brine, dried over sodium sulphate, filtered and evaporated in vacuo to give: 5-chloro-1,3-dimethyl-4-nitro-pyrazole (1.1 g, 82%).

(b) 5-Chloro-1,3-dimethyl-pyrazol-4-amine (Intermediate Ad)

To a stirred solution of 5-chloro-1,3-dimethyl-4-nitro-pyrazole (146 mg, 1 mmol) in THF (5 mL) was added acetic acid (1.1 mL, 16 mmol). The mixture was cooled to 0° C. and zinc (1.31 g, 20 mmol) was added in small portions keeping the temperature below 20° C. The reaction mixture was stirred at room temperature o/n. After TLC analysis indicated a complete conversion the starting material the mixture was filtered over Decalite® and the Zn-Decalite® residue was washed with DCM/MeOH 9:1. The combined filtrates were washed with a 5% $NaHCO_3$-solution followed by water and bring. The organic layer was dried ($Na_2SO_4$), filtered and concentrated in vacuo to yield title compound (78 mg, 53%).

Intermediate Ae 3,5-diethyl-1-(2-methoxyethyl)pyrazol-4-amine

The title compound was prepared in an analogous manner as described for Intermediate Aa, starting from 2-bromoethyl methyl ether and 3,5-diethyl-4-nitro-1H-pyrazole to give 3,5-diethyl-1H-pyrazol-4-amine (143 mg, 36%).

Intermediate Af 1-(4-Amino-3,5-dimethyl-pyrazol-1-yl)-2-methyl-propan-2-ol (a) 1-(3,5-Dimethyl-4-nitro-pyrazol-1-yl)-2-methyl-propan-2-ol To a solution of 3,5-dimethyl-4-nitro-1H-pyrazole (706 mg, 5 mmol) and DBU (1.49 mL, 10 mmol) in acetonitril (10 mL) was added isobutylene-oxide (669 µL, 7.5 mmol). The mixture was heated at 65° C. for 72 h. After cooling to room temperature, the mixture was poured into water and extracted with ethyl acetate (3×50 mL). The combined organic layers were washed with 1M HCl-solution, water and bring (50 mL), dried over sodium sulfate, filtered and concentrated under reduced pressure. The residue was purified by column chromatography (heptane/EtOAc=100/0 to 60/40 v/v %) to afford 1-(3,5-Dimethyl-4-nitro-pyrazol-1-yl)-2-methyl-propan-2-ol (799 mg, 75%).

(b) 1-(4-Amino-3,5-dimethyl-pyrazol-1-yl)-2-methyl-propan-2-ol (Intermediate Af)

This compound was prepared in an analogous manner as described for Intermediate B step b, starting from 1-(3,5-dimethyl-4-nitro-pyrazol-1-yl)-2-methyl-propan-2-ol to afford the title compound (229 mg, 39%).

Intermediate Ag

3-Ethyl-5-methyl-isoxazol-4-amine (a) tert-Butyl N-(3-ethyl-5-methyl-isoxazol-4-yl) carbamate Diphenylphosphoryl azide (2.51 mL, 11.6 mmol) was added to a solution of 3-ethyl-5-methyl-isoxazole-4-carboxylic acid (1.5 g, 9.67 mmol), triethylamine (2.7 mL, 19.3 mmol), and tert-butylalcohol (0.92 mL, 9.67 mmol) in toluene (50 mL) and stirred for 4 h at 100° C. The solvent was removed by evaporation and the residue taken up in EtOAc (50 mL). The organic layer washed with water and brine, dried over sodium sulfate, filtered and concentrated in vacuo. The residue was purified by flash chromatography on silica gel in heptane/ethyl acetate=10/0 to 7/3 v/v % as eluent. The fractions containing the title compound were pooled and evaporated to obtain the title compound. (1.67 g, 76.3%)

(b) 3-Ethyl-5-methyl-isoxazol-4-amine (Intermediate Ag)

tert-Butyl N-(3-ethyl-5-methyl-isoxazol-4-yl)carbamate (500 mg, 2.2 mmol) was dissolved in TFA/Dichloromethane=1/1 v/v % (5 mL) and stirred at room temperature for 1 h. The resulting mixture was evaporated and the residue was dissolved in methanol and then filtered over an SCX-2 column. After rinsing the column with methanol, the desired product was eluted with an 0.7N ammonia/methanol solution. The resulting eluate was concentrated in vacuo to give the title compound (302.7 mg, 92%).

Intermediate Ah

1-[2-[2-(2-Methoxyethoxy)ethoxy]ethyl]-3,5-dimethyl-pyrazol-4-amine (a) 1-[2-[2-(2-Methoxyethoxy)ethoxy]ethyl]-3,5-dimethyl-4-nitro-pyrazole To a cold (0° C.) solution of 3,5-dimethyl-4-nitro-1H-pyrazole (250 g, 177 mmol), triethylene glycol monomethylether (482 µL, 301 mmol) and triphenylphosphine (789 mg, 3.01 mmol) in THF (10 mL) was added dropwise a solution of 40% DEAD in toluene (1.31 mL, 3.01 mmol) The reaction mixture was allowed to warm to room temperature and was stirred for 3 h. Ethyl acetate was added and washed with a 10% NaCl-solution. The organic layer was dried (Na$_2$SO$_4$), filtered and concentrated. The residue was purified by column chromatography (DCM/MeOH=99/1 to 95/5 v/v %) to afford 1-[2-[2-(2-methoxyethoxy)ethoxy]ethyl]-3,5-dimethyl-4-nitro-pyrazole (1.7 g, crude) which was used directly in the next step.

(b) 1-[2-[2-(2-methoxyethoxy)ethoxy]ethyl]-3,5-dimethyl-pyrazol-4-amine (Intermediate Ah)

1-[2-[2-(2-Methoxyethoxy)ethoxy]ethyl]-3,5-dimethyl-4-nitro-pyrazole (1.5 g, 1.77 mmol theor.) was dissolved in THF (15 mL) and acetic acid (1.6 mL) was added. The mixture was cooled to 0° C. and zinc (2.3 g, 35.4 mmol) was added in small portions keeping the temperature below 20° C. The reaction mixture was stirred at room temperature o/n. After TLC analysis indicated a complete conversion of the starting material, the mixture was filtered over Decalite® and the Zn-Decalite® residue was washed with ethyl acetate. The combined filtrates were washed with a 1N NaOH-solution, followed by water and brine. The organic layer was dried (Na$_2$SO$_4$), filtered and concentrated in vacuo. The residue was dissolved in methanol and then filtered over a SCX-2 column. After rinsing the column with methanol, the desired product was eluted with an 0.7 N ammonia/methanol solution to give the title compound (340.1 mg, 74.7%).

Intermediate Ai

Tert-Butyl 3-(4-amino-3,5-dimethyl-pyrazol-1-yl)azetidine-1-carboxylate

The title compound was prepared in an analogous manner as described for Intermediate Ah, starting from 3,5-dimethyl-4-nitro-1H-pyrazole and 1-Boc-3-hydroxyazetidine to give 261.1 mg of tert-Butyl-3-(4-amino-3,5-dimethyl-pyrazol-1-yl)azetidine-1-carboxylate (quant.).

Intermediate Aj 3,5-Dimethyl-1-(oxetan-2-ylmethyl)pyrazol-4-amine

The title compound was prepared in an analogous manner as described for Intermediate Ah, starting from 3,5-dimethyl-4-nitro-1H-pyrazole and 2-hydroxymethyloxetane to give 116 mg of 3,5-dimethyl-1-(oxetran-2-ylmethyl)pyrazol-4-amine (36.2%)

Intermediate Ak 3,5-Diethyl-1-[2-(2-methoxyethoxy)ethyl]pyrazol-4-amine

The title compound was prepared in an analogous manner as described for Intermediate Aa, starting from 3,5-diethyl-4-nitro-1H-pyrazole (Intermediate Ac-b) and 1-bromo-2-(2-methoxyethoxy)-ethane to give 290 mg of 3,5-diethyl-1-[2-(2-methoxyethoxy)ethyl]pyrazol-4-amine (72.2%).

Intermediate Al 3,5-Diethyl-1-(oxetan-3-yl)pyrazol-4-amine

The title compound was prepared in an analogous manner as described for Intermediate Aa, starting from 3,5-diethyl-4-nitro-1H-pyrazole (Intermediate Ac-b) and toluene-4-sulfonic acid oxetan-3-yl ester to give 165 mg of 3,5-diethyl-1-(oxetan-3-yl)pyrazol-4-amine (47.7%.).

Intermediate Am 1-(2-Dimethylaminoethyl)-3,5-dimethyl-pyrazol-4-amine

The title compound was prepared in an analogous manner as described for Intermediate Ah, starting from 3,5-dimethyl-4-nitro-1H-pyrazole and N,N-dimethylethanolamine to give 380.4 mg of 1-(2-dimethylaminoethyl)-3,5-dimethyl-pyrazol-4-amine (quant.).

Example 1

N-(2,6-dimethylphenyl)-2-[4-[(2-hydroxy-2-methyl-propyl)carbamoyl]-2-methoxy-anilino]-5,6-dihydropyrimido[4,5-e]indolizine-7-carboxamide (a) Ethyl 2-[4-[(2-hydroxy-2-methyl-propyl)carbamoyl]-2-methoxy-anilino]-5,6-dihydropyrimido[4,5-e]indolizine-7-carboxamide Ethyl 2-chloro-5,6-dihydropyrimido[4,5-e]indolizine-7-carboxylate (Intermediate 1, 200 mg, 0.72 mmol), 4-amino-N-(2-hydroxy-2-methyl-propyl)-3-methoxy-benzamide (Intermediate A, 172 mg, 0.72 mmol) and cesium carbonate (937 mg; 2.89 mmol) were suspended in dioxane (20 mL). Nitrogen was bubbled through the mixture at 30° C. for 5 minutes followed by the addition of 9,9-bis-dimethyl-4,5-bis(diphenylphosphino)xanthene (41.7 mg, 72 μmol) and tris(dibenzylideneacetone)dipalladium(0) (33.0 mg 36 μmol). The reaction mixture was stirred at 80° C. for 20 hours under a flow of nitrogen gas. Ethyl acetate/water/brine=1/1/1 v/v % (50 mL) were added to the reaction mixture and stirring was continued for 15 min. After filtration over Decalite® the water layer was separated and extracted with ethyl acetate (2×20 mL). The combined organic layers were subsequently washed with water (40 mL), bring (20 mL), dried over sodium sulphate, filtered and concentrated in vacuo. The crude product was purified by column chromatography on silica (DCM/MeOH=10/0 to 9/1 v/v %) to give the title compound (190 mg, 55.3%).

(b) N-(2,6-dimethylphenyl)-2-[4-[(2-hydroxy-2-methyl-propyl)carbamoyl]-2-methoxy-anilino]-b,6-dihydropyrimido[4,5-e]indolizine-7-carboxamide LiHDMS (1M in THF/ethylbenzene, 0.61 mL, 0.61 mmol) was added to a cold (0° C.) solution of 2,6-dimethylaniline (38.5 μL, 0.31 mmol) in THF (1 mL). After 15 minutes of stirring at 0° C., ethyl 2-[4-[(2-hydroxy-2-methyl-propyl)carbamoyl]-2-methoxy-anilino]-5,6-dihydropyrimido[4,5-e]indolizine-7-carboxylate (50 mg, 0.10 mmol) in THF (3 mL) was added dropwise to the reaction mixture and stirring was continued at 0° C. for 90 min at 0° C. Additional LiHMDS (100 μL) was added dropwise at room temperature and stirring was continued for 2 hours at room temperature. The reaction mixture was quenched with 20 mL saturated solution of ammonium chloride and extracted with ethyl acetate. The combined organic layers were washed with water, bring, dried over sodium sulfate, filtered and concentrated under reduced pressure. The residue was purified by preparative HPLC. Fractions containing product were collected and lyophilized to afford N-(2,6-dimethylphenyl)-2-[4-[(2-hydroxy-2-methyl-propyl)carbamoyl]-2-methoxy-anilino]-5,6-dihydropyrimido[4,5-e]indolizine-7-carboxamide (10 mg, 18%). Data: LCMS (B) $R_t$: 14.432 min; m/z 555.3 (M+H)$^+$.

Example 2

N-(2-chloro-6-methyl-phenyl)-2-[2-methyl-4-(4-methylpiperazin-1-yl)anilino]-5,6-dihydropyrimido [4,5-e]indolizine-7-carboxamide To a suspension of 2-[2-methyl-4-(4-methylpiperazin-1-yl)anilino]-5,6-dihydropyrimido[4,5-e]indolizine-7-carbonyl chloride (Intermediate 2, 52 mg, 0.07 mmol theor.) in acetonitrile (2 mL) was added 2-chloro-6-methylaniline (15 µL, 0.12 mmol) and a catalytic amount of 4-DMAP. The reaction mixture was stirred at 50° C. o/n. After evaporation of the solvent, the crude product was purified by preparative HPLC. Fractions containing product were collected and concentrated in vacuo. The residue was partitioned between dichloromethane and 5% NaHCO$_3$-solution. The organic phase was separated over a PE-filter and evaporated to afford 28 mg of the title compound (74% yield). Data: LCMS (B) $R_t$: 9.852 min; m/z 542.2/544.2 (M+H)$^+$ (chloride-pattern).

Example 3

N-(2-bromo-6-methyl-phenyl)-2-(2-methoxy-4-morpholino-anilino)-5,6-dihydropyrimido[4,5-e]indolizine-7-carboxamide This compound was prepared from its corresponding acid chloride, using the same sequence of reactions, as described for Intermediate 2, using Intermediate C as starting material. The acid chloride was subsequently reacted with 2-bromo-6-methylaniline according to procedures described in Example 2. Purification was performed using preparative HPLC to afford the title compound (6.8 mg, 17%). Data: LCMS (A) $R_t$: 8.031 min; m/z 587.1/589.1 (M+H)$^+$ (bromide-pattern).

Example 4

N-(2-ethyl-6-methyl-phenyl)-2-[4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using commercially available 4-(4-methylpiperazino)aniline as starting material. The acid chloride was subsequently reacted with 6-ethyl-o-toluidine according to procedures described in Example 2. Purification was performed using preparative HPLC to afford the title compound (18 mg, 58%). Data: LCMS (B) $R_t$: 10.456 min; m/z 522.3 (M+H)$^+$.

Example 5

N-(2-chloro-6-methyl-phenyl)-2-[(2-methyl-6-morpholino-3-pyridyl)amino]-5,6-dihydropyrimido[4,5-e]indolizine-7-carboxamide This compound was prepared from its corresponding acid chloride, using the same sequence of reactions, as described for Intermediate 2, using Intermediate D as starting material. The acid chloride was subsequently reacted with 2-chloro-6-methylaniline according to procedures described in Example 2. Purification was performed using preparative HPLC to afford the title compound (18 mg, 59%). Data: LCMS (B) $R_t$: 10.991 min; m/z 530.2/532.2 (M+H)$^+$ (chloride-pattern).

Example 6

N-(2-chloro-6-methyl-phenyl)-2-[(2-chloro-4-(4-methylpiperazin-1-yl)anilino]-5,6-dihydropyrimido [4,5-e]indolizine-7-carboxamide This compound was prepared from its corresponding acid chloride, using the same sequence of reactions, as described for Intermediate 2, using Intermediate E as starting material. The acid chloride was subsequently reacted with 2-chloro-6-methylaniline according to procedures described in Example 2. Purification was performed using preparative HPLC to afford the title compound (4 mg, 11%). Data: LCMS (B) $R_t$: 10.886 min; m/z 562.2 (M+H)$^{30}$.

Example 7

N-(2,6-dimethylphenyl)-2-[2-fluoro-4-[(1-methyl-4-piperidyl)carbamoyl]anilino]-5,6-dihydropyrimido [4,5-e]indolizine-7-carboxamide This compound was prepared from its corresponding acid chloride, using the same sequence of reactions, as described for Example 1-a and Intermediate 2, using Intermediate O as starting material. The acid chloride was subsequently reacted with 2,6-dimethylaniline according to procedures described in Example 2. Purification was performed using preparative HPLC to afford the title compound (4 mg, 20%). Data: LCMS (B) $R_t$: 10.469 min; m/z 568.3 (M+H)$^+$.

Example 8

2-[2-Chloro-4-[(1-methyl-4-piperidyl)carbamoyl] anilino]-N-(2,6-diethylphenyl)-5,6-dihydropyrimido [4,5-e]indolizine-7-carboxamide This compound was prepared from its corresponding acid chloride, using the same sequence of reactions, as described for Intermediate 2, using Intermediate N as starting material. The acid chloride was subsequently reacted with 2,6-diethylaniline according to procedures described in Example 2. Purification was performed using preparative HPLC to afford the title compound (4.7 mg, 10%). Data: LCMS (B) $R_t$: 10.222 min; m/z 612.2/614.3(M+H)$^+$.

Example 9

N-(3,5-diethyl-1H-pyrazol-4-yl)-2-[2-methyl-4-(4-methylpiperazin-1-yl)anilino]-5,6-dihydropyrimido [4,5-e]indolizine-7-carboxamide 2-[2-Methyl-4-(4-methylpiperazin-1-yl)anilino]-5,6-dihydropyrimido[4,5-e]indolizine-7-carboxylic acid was prepared, in an analogous manner as described for Intermediate 2, using Intermediate B.

2-[2-Methyl-4-(4-methylpiperazin-1-yl)anilino]-5,6-dihydropyrimido[4,5-e]indolizine-7-carboxylic acid (26 mg, 0.06 mmol) was dissolved in N,N-dimethylformamide (1.5 ml). HATU (25 mg, 0.066 mmol) and triethylamine (25 µL, 0.178 mmol) were added subsequently and the mixture stirred for 10 min at room temperature. 3,5-Diethyl-1H-pyrazol-4-amine (7 mg, 0.07 mmol) was added and the mixture was stirred at room temperature o/n. The mixture was poured into a mixture ethyl acetate/water/bring 1/1/1 and stirred for 15 min. The organic layer was separated, washed with brine, dried over sodium sulphate filtered and concentrated in vacuo. Purification was performed using preparative HPLC to afford the title compound (14.0 mg, 43%). Data: LCMS (B) $R_t$: 7.530 min; m/z 540.3 $(M+H)^+$.

Example 10

N-(2-methoxy-6-methyl-phenyl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate F as starting material. The acid chloride was subsequently reacted with 2-methoxy-6-methyl-aniline according to procedures described in Example 2. Purification was performed using preparative HPLC to afford the title compound (16.1 mg, 29.1%). Data: LCMS (B) $R_t$: 9.925 min; m/z 554.3 $(M+H)^+$.

Example 11

N-(2,6-diisopropylphenyl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate F as starting material. The acid chloride was subsequently reacted with 2,6-diisopropylaniline according to procedures described in Example 2. Purification was performed using preparative HPLC to afford the title compound (15.9 mg, 35.7%). Data: LCMS (B) $R_t$: 12.686 min; m/z 594.4 $(M+H)^+$.

Example 12

N-(3,5-dimethylsoxazol-4-yl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate F as starting material. The acid chloride was subsequently reacted with 3,5-dimethylsoxazol-4-amine according to procedures described in Example 2. Purification was performed using preparative HPLC to afford the title compound (24.4 mg, 46.1%). Data: LCMS (B) $R_t$: 8.408 min; m/z 529.3 $(M+H)^+$.

Example 13

N-[3,5-diethyl-1-(2-methoxyethyl)pyrazol-4-yl]-2-[2-methyl-4-[(1-methyl-4-piperidyl)oxy]anilino]-5,6-dihydropyrimido[4,5-e]indolizine-7-carboxamide This compound was prepared from its corresponding acid chloride, using the same sequence of reactions, as described for Intermediate 2, using Intermediate T as starting material. The acid chloride was subsequently reacted with Intermediate Ae according to procedures described in Example 2. Purification was performed using preparative HPLC to afford the title compound (14 mg, 27%). Data: LCMS (B) $R_t$: 9.531 min; m/z 613.3 $(M+H)^+$.

Example 14

2-[2-Ethoxy-4-[(1-methyl-4-piperidyl)carbamoyl]anilino]-N-(2-ethyl-6-methyl-phenyl)-5,6-dihydropyrimido[4,5-e]indolizine-7-carboxamide This compound was prepared from its corresponding acid chloride, using the same sequence of reactions, as described for Example 1-a and Intermediate 2, using Intermediate P as starting material. The acid chloride was subsequently reacted with 6-ethyl-o-toluidine according to procedures described in Example 2. Purification was performed using preparative HPLC to afford the title compound (5.3 mg, 14%). Data: LCMS (B) $R_t$: 12.313 min; m/z 608.3 $(M+H)^+$.

Example 15

N-(3,5-dimethyl-1H-pyrazol-4-yl)-2-[2-methoxy-4-[(1-methyl-4-piperidyl)oxy]anilino]-5,6-dihydropyrimido[4,5-e]indolizine-7-carboxamide This compound was prepared from its corresponding acid chloride, using the same sequence of reactions, as described for Intermediate 2, using Intermediate S as starting material. The acid chloride was subsequently reacted with Intermediate Ab according to procedures described in Example 2. Purification was performed using preparative HPLC to accord the title compound (14.1 mg, 37%). Data: LCMS (B) $R_t$: 7.902 min; m/z 543.2 $(M+H)^+$.

Example 16

N-[1-(2-methoxyethyl)-3,5-dimethyl-pyrazol-4-yl]-2-(2-methoxy-4-piperazin-1-yl-anilino)-5,6-dihydropyrimido[4,5-e]indolizine-7-carboxamide This compound was prepared from its corresponding acid chloride, using the same sequence of reactions as described for Example 9 using Intermediate H as starting material. The carboxylic acid was subsequently reacted with Intermediate Aa in an analogous manner as described in Example 9. After deprotection of the Boc-group, purification was performed using preparative HPLC to afford the title compound (5.2 mg, 28%). Data: LCMS (B) $R_t$: 8.140 min; m/z 572.3 $(M+H)^+$.

Example 17

N-(2,6-dimethylphenyl)-2-(2-methoxy-4-piperazin-1-yl-anilino)-5,6-dihydropyrimido[4,5-e]indolizine-7-carboxamide This compound was prepared from its corresponding acid chloride, using the same sequence of reactions as described for Example 9, using Intermediate H as starting material. The carboxylic acid was subsequently reacted with 2,6-dimethylaniline in an analogous manner as described in Example 1. After deprotection of the Boc-group, purification was performed using preparative HPLC to afford the title compound (16 mg, 52%). Data: LCMS (B) $R_t$: 10.268 min; m/z 524.3 $(M+H)^+$.

Example 18

N-(3,5-diethyl-1H-pyrazol-4-yl)-2-(2-methoxy-4-piperazin-1-ylanilino)-5,6-dihydropyrimido[4,5-e]indolizine-7-carboxamide This compound was prepared from its corresponding acid chloride, using the same sequence of reactions as described for Example 9, using Intermediate H as starting material. The carboxylic acid was subsequently reacted with Intermediate Ac in an analogous manner as described in Example 9. After deprotection of the Boc-group, purification was performed using preparative HPLC to afford the title compound (7 mg, 32%). Data: LCMS (B) $R_t$: 8.065 min; m/z 542.3 (M+H)$^+$.

Example 19

N-[3,5-diethyl-1-(2-methoxyethyl)pyrazol-4-yl]-2-(2-methoxy-4-piperazin-1-yl-anilino)-5,6-dihydropyrimido[4,5-e]indolizine-7-carboxamide This compound was prepared from its corresponding acid chloride, using the same sequence of reactions as described for Example 9 and using Intermediate H as starting material. The carboxylic acid was subsequently reacted with Intermediate Ae in an analogous manner as described in Example 9. After deprotection of the Boc-group, purification was performed using preparative HPLC to afford the title compound (4 mg, 32%). Data: LCMS (B) $R_t$: 9.146 min; m/z 600.3 (M+H)$^+$.

Example 20

N-(2,6-diethylphenyl)-2-[2-methoxy-4-(4-methyl-piperazin-1-yl)anilino]-5,6-dihydropyrimido[4,5-e]indolizine-7-carboxamide This compound was prepared from its corresponding ester, using the same sequence of reactions as described for Example 1, using Intermediate F as starting material. The ester was subsequently reacted with 2,6-diethylaniline according to procedures described in Example 1. Purification was performed using preparative HPLC to afford the title compound (13.5 mg, 23.2%). Data: LCMS (C) $R_t$: 12.686 min; m/z 566.4 (M+H)$^+$.

Example 21

N-(3,5-diethyl-1H-pyrazol-4-yl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions for Intermediate 2, using Intermediate F as starting material. The acid chloride was subsequently reacted with Intermediate Ac according to procedures described in Example 2. Purification was performed using preparative HPLC to afford the title compound (22 mg, 36%). Data: LCMS (B) $R_t$: 8.319 min; m/z 557.3 (M+H)$^+$.

Example 22

2-[2-Methoxy-4-(4-methylpiperazin-1-yl)anilino]-N-(2,4,6-trimethylphenyl)-5,6-dihydropyrimido[4,5-e]indolizine-7-carboxamide This compound was prepared from its corresponding acid chloride, using the same sequence of reactions for Intermediate 2, using Intermediate F as starting material. The acid chloride was subsequently reacted with 2,4,6-trimethylaniline according to procedures described in Example 2. Purification was performed using preparative HPLC to afford the title compound (16 mg, 26%). Data: LCMS (B) $R_t$: 11.240 min; m/z 552.3 (M+H)$^+$.

Example 23

N-[2-(hydroxymethyl)-6-methyl-phenyl]-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions for Intermediate 2, using Intermediate F as starting material. The acid chloride was subsequently reacted with (2-amino-3-methyl-phenyl)methanol according to procedures described in Example 2. Purification was performed using preparative HPLC to afford the title compound (6 mg, 10%). Data: LCMS (B) $R_t$: 8.876 min; m/z 554.3 (M+H)$^+$.

Example 24

N-(2-fluoro-6-methyl-phenyl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions for Intermediate 2, using Intermediate F as starting material. The acid chloride was subsequently reacted with 2-fluoro-6-methylaniline according to procedures described in Example 2. Purification was performed using preparative HPLC to afford the title compound (21.4 mg, 39.6%). Data: LCMS (B) $R_t$: 9.878 min; m/z 542.3 (M+H)$^+$.

Example 25

N-(2-chloro-4-methyl-3-pyridyl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions for Intermediate 2, using Intermediate F as starting material. The acid chloride was subsequently reacted with 3-amino-2-chloro-4-methylpyridine according to procedures described in Example 2. Purification was performed using preparative HPLC to afford the title compound (11.9 mg, 28.4%). Data: LCMS (B) $R_t$: 8.790 min; m/z 559.2/561.2 (M+H)$^+$ (chloride-pattern).

Example 26

N-[1-(2-methoxyethyl)-3,5-dimethyl-pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions for Intermediate 2, using Intermediate F as starting material. The acid chloride was subsequently reacted with Intermediate Aa according to procedures described in Example 2. Purification was performed using preparative HPLC to afford the title compound (25.0 mg, 424.7%). Data: LCMS (B) $R_t$: 8.128 min; m/z 586.3 (M+H)$^+$.

Example 27

N-(3,5-dimethyl-1H-pyrazol-4-yl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions for Intermediate 2, using Intermediate F as starting material. The acid chloride was subsequently reacted with Intermediate Ab according to procedures described in Example 2. Purification was performed using preparative HPLC to afford the title compound (14.0 mg, 26.5%). Data: LCMS (B) $R_t$: 7.146 min; m/z 528.3 (M+H)$^+$.

Example 28

N-(5-chloro-1,3-dimethyl-pyrazol-4-yl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions for Intermediate 2, using Intermediate F as starting material. The acid chloride was subsequently reacted with Intermediate Ad according to procedures described in Example 2. Purification was performed using preparative HPLC to afford the title compound (18 mg, 29%). Data: LCMS (B) $R_t$: 8.563 min; m/z 562.2/564.2 (M+H)$^+$ (chloride-pattern).

Example 29

N-(2-ethylphenyl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions as described for Intermediate 2, using Intermediate F as starting material. The acid chloride was subsequently reacted with 2-ethylaniline according to procedures described in Example 2. Purification was performed using preparative HPLC to afford the title compound (14 mg, 26%). Data: LCMS (B) $R_t$: 10.708 min; m/z 538.3 (M+H)$^+$.

Example 30

N-(2,6-difluorophenyl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions as described for Intermediate 2, using Intermediate F as starting material. The acid chloride was subsequently reacted with 2,6-difluoroaniline according to procedures described in Example 2. Purification was performed using preparative HPLC to afford the title compound (20.5 mg, 37.5%). Data: LCMS (B) $R_t$: 9.607 min; m/z 546.2 (M+H)$^+$.

Example 31

N-(3,5-diethyl-1H-pyrazol-4-yl)-2-[2-ethoxy-4-(4-methylpiperazin-1-yl)anilino]-5,6-dihydropyrimido[4,5-e]indolizine-7-carboxamide This compound was prepared from its corresponding acid chloride, using the same sequence of reactions as described for Intermediate 2, using Intermediate G as starting material. The acid chloride was subsequently reacted with Intermediate Ac according to procedures described in Example 2. Purification was performed using preparative HPLC to afford the title compound (10 mg, 37%). Data: LCMS (B) $R_t$: 8.939 min; m/z 570.3 (M+H)$^+$.

Example 32

2-[2-Ethoxy-4-(4-methylpiperazin-1-yl)anilino]-N-(2-ethyl-6-methyl-phenyl)-5,6-dihydropyrimido[4,5-e]indolizine-7-carboxamide This compound was prepared from its corresponding acid chloride, using the same sequence of reactions as described for Intermediate 2, using Intermediate G as starting material. The acid chloride was subsequently reacted with 6-ethyl-o-toluidine according to procedures described in Example 2. Purification was performed using preparative HPLC to afford the title compound (5 mg, 9%). Data: LCMS (B) $R_t$: 11.636 min; m/z 566.3 (M+H)$^+$.

Example 33

N-(3,5-diethyl-1H-pyrazol-4-yl)-2-[2-(difluoromethoxy)-4-(4-methylpiperazin-1-yl)anilino]-5,6-dihydropyrimido[4,5-e]indolizine-7-carboxamide This compound was prepared from its corresponding carboxylic acid, using the same sequence of reactions as described for Intermediate 2, using Intermediate J as starting material. The carboxylic acid was subsequently reacted with Intermediate Ac in an analogous manner as described in Example 2. Purification was performed using preparative HPLC to afford the title compound (9.6 mg, 23%). Data: LCMS (B) $R_t$: 8.864 min; m/z 592.3 (M+H)$^+$.

Example 34

N-(2,6-dimethylphenyl)-2-[(4-methyl-6-morpholino-3-pyridyl)amino]-5,6-dihydropyrimido[4,5-e]indolizine-7-carboxamide This compound was prepared from its corresponding acid chloride, using the same sequence of reactions as described for Intermediate 2, using Intermediate K as starting material. The acid chloride was subsequently reacted with 2,6-dimethylaniline according to procedures described in Example 2. Purification was performed using preparative HPLC to afford the title compound (6.2 mg, 17.4%). Data: LCMS (B) $R_t$: 10.575 min; m/z 510.3 (M+H)$^+$.

Example 35

N-(2-chloro-6-methyl-phenyl)-2-[2-methoxy-4-[(1-methyl-4-piperidyl)carbamoyl]anilino]-5,6-dihydropyrimido[4,5-e]indolizine-7-carboxamide This compound was prepared from its corresponding acid chloride, using the same sequence of reactions as described for Example 1-a and Intermediate 2, using Intermediate L as starting material. The acid chloride was subsequently reacted with 2-chloro-6-methylaniline according to procedures described in Example 2. Purification was performed using preparative HPLC to afford the title compound (9.8 mg, 21%). Data: LCMS (B) $R_t$: 11.000 min; m/z 600.2/602.2 (M+H)$^+$ (chloride-pattern).

Example 36

N-(2,6-diethylphenyl)-2-[2-methyl-4-[(1-methyl-4-piperidyl)carbamoyl]anilino]-5,6-dihydropyrimido [4,5-e]indolizine-7-carboxamide This compound was prepared from its corresponding acid chloride, using the same sequence of reactions as described for Example 1-a and Intermediate 2, using Intermediate M as starting material. The acid chloride was subsequently reacted with 2,6-diethylaniline according to procedures described in Example 2. Purification was performed using preparative HPLC to afford the title compound (2.5 mg, 11%). Data: LCMS (B) $R_t$: 11.332 min; m/z 592.3 (M+H)$^+$.

Example 37

2-[2-(Difluoromethoxy)-4-[(1-methyl-4-piperidyl) carbamoyl]anilino]-N-(2,6-dimethylphenyl)-5,6-dihydropyrimido[4,5-e]indolizine-7-carboxamide This compound was prepared from its corresponding acid chloride, using the same sequence of reactions as described for Example 1-a and Intermediate 2, using Intermediate Q as starting material. The acid chloride was subsequently reacted with 2,6-dimethylaniline according to procedures described in Example 2. Purification was performed using preparative HPLC to afford the title compound (4 mg, 12%). Data: LCMS (B) $R_t$: 11.282 min; m/z 616.3 (M+H)$^+$.

Example 38

N-(2,6-diethylphenyl)-2-[2-methoxy-4-(1-methyl-pyrazol-4-yl)anilino]-5,6-dihydropyrimido[4,5-e] indolizine-7-carboxamide 2-(4-Bromo-2-methoxy-anilino)-N-(2,6-diethylphenyl)-5,6-dihydropyrimido[4,5-e]indolizine-7-carboxamide
This compound was prepared from its corresponding acid chloride, using the same sequence of reactions as described for Intermediate 2, using commercially available 4-bromo-2-methoxyaniline as starting material. The acid chloride was subsequently reacted with 2,6-dimethylaniline according to procedures described in Example 2. Purification was performed using preparative HPLC to afford the title compound.
(b) N-(2,6-diethylphenyl)-2-[2-methoxy-4-(1-methylpyrazol-4-yl)anilino]-5,6-dihydropyrimido[4,5-e]indolizine-7-carboxamide
A mixture of 2-(4-bromo-2-methoxy-anilino)-N-(2,6-diethylphenyl)-5,6-dihydropyrimido[4,5-e]indolizine-7-carboxamide (22.6 mg, 0.041 mmol), 1-methyl-4-(4,4,5,5-tetramethyl-1,3,2-dioxaborolan-2-yl)-1H-pyrazole (17.2 mg, 0.083 mmol), 1,1'-bis(diphenylphosphino)ferrocene palladium(II)chloride, complex with dichloromethane (3.4 mg) and potassium carbonate (28.3 mg, 0.205 mmol) in dioxane/water (1.5 mL/0.3 mL) was heated in a microwave at 140° C. for 60 minutes in a sealed tube. After cooling to ambient temperature, the mixture was concentrated in vacuo. The resulting residue was diluted with ethyl acetate, washed with water and brine, dried over sodium sulfate, filtered and concentrated in vacuo. Purification was performed using preparative HPLC to afford the title compound (15.2 mg, 38%). Data: LCMS (B) $R_t$: 17.769 min; m/z 548.3 (M+H)$^+$.

Example 39

N-(2,6-dimethylphenyl)-2-[2-methoxy-4-[(1-methyl-4-piperidyl)oxy]anilino]-5,6-dihydropyrimido[4,5-e] indolizine-7-carboxamide This compound was prepared from its corresponding acid chloride, using the same sequence of reactions as described for Intermediate 2, using Intermediate S as starting material. The acid chloride was subsequently reacted with 2,6-dimethylaniline according to procedures described in Example 2. Purification was performed using preparative HPLC to afford the title compound (13.8 mg, 37.7%). Data: LCMS (B) $R_t$: 11.129 min; m/z 553.3 (M+H)$^+$.

Example 40

N-(2-ethyl-6-methyl-phenyl)-2-[2-methoxy-4-[(1-methyl-4-piperidyl)oxy]anilino]-5,6-dihydropyrimido[4,5-e]indolizine-7-carboxamide This compound was prepared from its corresponding acid chloride, using the same sequence of reactions as described for Intermediate 2, using Intermediate S as starting material. The acid chloride was subsequently reacted with 6-ethyl-o-toluidine according to procedures described in Example 2. Purification was performed using preparative HPLC to afford the title compound (8.7 mg, 21.9%). Data: LCMS (B) $R_t$: 11.778 min: m/z 567.3 (M+H)$^+$.

Example 41

N-(2-chloro-6-methyl-phenyl)-2-[2-methoxy-4-[(1-methyl-4-piperidyl)oxy]anilino]-5,6-dihydropyrimido[4,5-e]indolizine-7-carboxamide This compound was prepared from its corresponding acid chloride, using the same sequence of reactions as described for Intermediate 2, using Intermediate S as starting material. The acid chloride was subsequently reacted with 2-chloro-6-ethylaniline according to procedures described in Example 2. Purification was performed using preparative HPLC to afford the title compound (11.4 mg, 28.4%). Data: LCMS (B) $R_t$: 11.395 min; m/z 573.2/575.2 (M+H)$^+$ (chloride pattern).

Example 42

N-(2-bromo-6-methyl-phenyl)-2-[2-methoxy-4-[(1-methyl-4-piperidyl)oxy]anilino]-5,6-dihydropyrimido[4,5-e]indolizine-7-carboxamide This compound was prepared from its corresponding acid chloride, using the same sequence of reactions as described for Intermediate 2, using Intermediate S as starting material. The acid chloride was subsequently reacted with 2-bromo-6-methylaniline according to procedures described in Example 2. Purification was performed using preparative HPLC to afford the title compound (11.8 mg, 27.3%). Data: LCMS (B) $R_t$: 11.527 min; m/z 617.2/619.2 (M+H)$^+$ (bromide pattern).

Example 43

N-(2,6-diethylphenyl)-2-[2-methoxy-4-[(1-methyl-4-piperidyl)oxy]anilino]-5,6-dihydropyrimido[4,5-e]indolizine-7-carboxamide This compound was prepared from its corresponding acid chloride, using the same sequence of reactions as described for Intermediate 2, using Intermediate S as starting material. The acid chloride was subsequently reacted with 2,6-diethylaniline according to procedures described in Example 2. Purification was performed using preparative HPLC to afford the title compound (13.6 mg, 33.6%). Data: LCMS (B) $R_t$: 12.578 min; m/z 581.3 (M+H)$^+$.

Example 44

N-[1-(2-methoxyethyl)-3,5-dimethyl-pyrazol-4-yl]-2-[2-methoxy-4-[(1-methyl-4-piperidyl)oxy]anilino]-5,6-dihydropyrimido[4,5-e]indolizine-7-carboxamide This compound was prepared from its corresponding acid chloride, using the same sequence of reactions as described for Intermediate 2, using Intermediate S as starting material. The acid chloride was subsequently reacted with Intermediate Aa according to procedures described in Example 2. Purification was performed using preparative HPLC to afford the title compound (16.9 mg, 40.1%). Data: LCMS (B) $R_t$: 8.940 min; m/z 601.3 (M+H)$^+$.

Example 45

N-(2,6-dimethylphenyl)-2-[2-methoxy-4-[(1-methyl-4-piperidyl)oxy]anilino]-5,6-dihydropyrimido[4,5-e]indolizine-7-carboxamide This compound was prepared from its corresponding acid chloride, using the same sequence of reactions as described for Intermediate 2, using Intermediate T as starting material. The acid chloride was subsequently reacted with 2,6-dimethylaniline according to procedures described in Example 2. Purification was performed using preparative HPLC to afford the title compound (14.2 mg, 40%). Data: LCMS (B) $R_t$: 10.765 min; m/z 537.3 (M+H)$^+$.

Example 46

N-(2-chloro-6-methyl-phenyl)-2-[2-methyl-4-[(1-methyl-4-piperidyl)oxy]anilino]-5,6-dihydropyrimido[4,5-e]indolizine-7-carboxamide This compound was prepared from its corresponding acid chloride, using the same sequence of reactions as described for Intermediate 2, using Intermediate T as starting material. The acid chloride was subsequently reacted with 2-chloro-6-methylaniline according to procedures described in Example 2. Purification was performed using preparative HPLC to afford the title compound (10.5 mg, 26%). Data: LCMS (B)$R_t$: 10.077 min; m/z 557.2/559.2 (m+H)$^+$ (chloride pattern).

Example 47

N-(3,5-diethyl-1H-pyrazol-4-yl)-2-[2-methyl-4-[(1-methyl-4-piperidyl)oxy]anilino]-5,6-dihydropyrimido[4,5-e]indolizine-7-carboxamide This compound was prepared from its corresponding acid chloride, using the same sequence of reactions as described for Intermediate 2, using Intermediate T as starting material. The acid chloride was subsequently reacted with Intermediate Ac according to procedures described in Example 2. Purification was performed using preparative HPLC to afford the title compound (7.6 mg, 19%). Data: LCMS (B) $R_t$: 8.307 min; m/z 555.3 (M+H)$^+$.

Example 48

2-[4-(2-methoxy-anilino]-N-(2,6-dimethylphenyl)-5,6-dihydropyrimido[4,5-e]indolizine-7-carboxamide This compound was prepared from its corresponding acid chloride, using the same sequence of reactions as described for Intermediate 2, using Intermediate U as starting material. The acid chloride was subsequently reacted with 2,6-dimethylaniline according to procedures described in Example 2. Purification was performed using preparative HPLC to afford the title compound (16.7 mg, 52.9%). Data: LCMS (B) $R_t$: 10.556 min; m/z 527.3 (M+H)$^+$.

Example 49

N-(2-chloro-6-methyl-phenyl)-2-[4-(2-dimethylaminoethyloxy)-2-methoxy-anilino]-5,6-dihydropyrimido[4,5-e]indolizine-7-carboxamide This compound was prepared from its corresponding acid chloride, using the same sequence of reactions as described for Intermediate 2, using Intermediate T as starting material. The acid chloride was subsequently reacted with 2-chloro-6-methylaniline according to procedures described in Example 2. Purification was performed using preparative HPLC to afford the title compound (15.6 mg, 52.9%). Data: LCMS (B) $R_t$: 10.566 min; m/z 547.2/549.2 (M+H)$^+$ (chloride-pattern).

Example 50

2-[4-(2-Dimethylaminoethyloxy)-2-methoxy-anilino]-N-(2-ethyl-6-methyl-phenyl)-5,6-dihydropyrimido[4,5-e]indolizine-7-carboxamide This compound was prepared from its corresponding acid chloride, using the same sequence of reactions as described for Intermediate 2, using Intermediate U as starting material. The acid chloride was subsequently reacted with 6-ethyl-o-toluidine according to procedures described in Example 2. Purification was performed using preparative HPLC to afford the title compound (17.2 mg, 53.1%). Data: LCMS (B) $R_t$: 11.075 min; m/z 541.3 (M+H)$^+$.

Example 51

N-(2-bromo-6-methyl-phenyl)-2-[4-(2-dimethylaminoethyloxy)-2-methoxy-anilino]-5,6-dihydropyrimido[4,5-e]indolizine-7-carboxamide This compound was prepared from its corresponding acid chloride, using the same sequence of reactions as described for Intermediate 2, using Intermediate U as starting material. The acid chloride was subsequently reacted with 2-bromo-6-methylaniline according to procedures described in Example 2. Purification was performed using preparative HPLC to afford the title compound (9.38 mg, 26.4%). Data: LCMS (B) $R_t$: 10.760 min; m/z 590.2/592.2 (M+H)$^+$ (bromide-pattern).

Example 52

N-(2,6-diethylphenyl)-2-[4-(2-dimethylaminoethyl-oxy)-2-methoxy-anilino]-5,6-dihydropyrimido[4,5-e]indolizine-7-carboxamide This compound was prepared from its corresponding acid chloride, using the same sequence of reactions as described for Intermediate 2, using Intermediate U as starting material. The acid chloride was subsequently reacted with 2,6-diethylaniline according to procedures described in Example 2. Purification was performed using preparative HPLC to afford the title compound (5.54 mg, 16.6%). Data: LCMS (B) $R_t$: 11.832 min; m/z 555.3 (M+H)$^+$.

Example 53

N-(3,5-diethyl-1H-pyrazol-4-yl)-2-[4-(2-dimethyl-aminoethyloxy)-2-methoxy-anilino]-5,6-dihydropyrimido[4,5-e]indolizine-7-carboxamide This compound was prepared from its corresponding acid chloride, using the same sequence of reactions as described for Intermediate 2, using Intermediate U as starting material. The acid chloride was subsequently reacted with Intermediate Ac according to procedures described in Example 2. Purification was performed using preparative HPLC to afford the title compound (13.4 mg, 41.0%). Data: LCMS (B) $R_t$: 8.189 min; m/z 545.3 (M+H)$^+$.

Example 54

2-[4-(2-Dimethylaminoethyloxy)-2-methoxy-anilino]-N-[1-(2-methoxyethyl)-3,5-dimethyl-pyrazol-4-yl]-5,6-dihydropyrimido[4,5-e]indolizine-7-carboxamide This compound was prepared from its corresponding acid chloride, using the same sequence of reactions as described for Intermediate 2, using Intermediate U as starting material. The acid chloride was subsequently reacted with Intermediate Aa according to procedures described in Example 2. Purification was performed using preparative HPLC to afford the title compound (18.3 mg, 53.2%). Data: LCMS (B) $R_t$: 8.234 min; m/z 575.3 (M+H)$^+$.

Example 55

N-(2,6-diethylphenyl)-2-[4-[(1-methyl-4-piperidyl)carbamoyl]anilino]-5,6-dihydropyrimido[4,5-e]indolizine-7-carboxamide This compound was prepared from its corresponding acid chloride, using the same sequence of reactions as described for Example 1-a and Intermediate 2, using Intermediate V as starting material. The acid chloride was subsequently reacted with 2,6-diethylaniline according to procedures described in Example 2. Purification was performed using preparative HPLC to afford the title compound (3.7 mg, 17%). Data: LCMS (B) $R_t$: 11.254 min; m/z 578.3 (M+H)$^+$.

Example 56

N-(2,6-dimethylphenyl)-2-(2-methyl-4-morpholino-anilino)-5,6-dihydropyrimido[4,5-e]indolizine-7-carboxamide This compound was prepared from its corresponding acid chloride, using the same sequence of reactions as described for Example 2a, using Intermediate W. The ester was subsequently reacted with 2,6-dimethylaniline according to procedures described in Example 1b. Purification was performed using preparative HPLC to afford the title compound (5.5 mg, 22%). Data: LCMS (B) $R_t$: 13.950 min; m/z 509.3 (M+H)$^+$.

Example 57

N-(2-ethyl-6-methyl-phenyl)-2-[2-isopropoxy-4-(4-methylpiperazin-1-yl)anilino]-5,6-dihydropyrimido[4,5-e]indolizine-7-carboxamide This compound was prepared from its corresponding acid chloride, using the same sequence of reactions as described for Intermediate 2, using Intermediate X as starting material. The acid chloride was subsequently reacted with 6-ethyl-o-toluidine according to procedures described in Example 2. Purification was performed using preparative HPLC to afford the title compound (13 mg, 28%). Data: LCMS (B) $R_t$: 12.031 min; m/z 580.3 (M+H)$^+$.

Example 58

N-(2,6-dimethylphenyl)-2-(2-methyl-4-piperazin-1-yl-anilino)-5,6-dihydropyrimido[4,5-e]indolizine-7-carboxamide This compound was prepared from its corresponding acid chloride, using the same sequence of reactions as described for Intermediate 2, using Intermediate I as starting material. The acid chloride was subsequently reacted with 2,6-dimethylaniline according to procedures described in Example 2. After deprotection of the Cbz-group, purification was performed using preparative HPLC to afford the title compound (20 mg, 64%). Data: LCMS (B) $R_t$: 9.706 min; m/z 508.3 (M+H)$^+$.

Example 59

N-(2,6-diethylphenyl)-2-[2-methoxy-4-(1-methyl-pyrrolidin-3-yl)oxy-anilino]-5,6-dihydropyrimido[4,5-e]indolizine-7-carboxamide This compound was prepared from its corresponding acid chloride, using the same sequence of reactions as described for Intermediate 2, using Intermediate Y as starting material. The acid chloride was subsequently reacted with 2,6-diethylaniline according to procedures described in Example 2. Purification was performed using preparative HPLC to afford the title compound (8.1 mg, 25%). Data: LCMS (B) $R_t$: 12.158 min; m/z 567.3 (M+H)$^+$.

Example 60

N-(2,6-diethylphenyl)-2-[2-methoxy-4-[(1-methyl-3-piperidyl)carbamoyl]anilino]-5,6-dihydropyrimido[4,5-e]indolizine-7-carboxamide (a) 4-[7-Ethoxycarbonyl-5,6-dihydropyrimido[4,5-e]indolizin-2-yl)amino]-3-methoxy-benzoic acid This compound was prepared, in an analogous manner as described for Intermediate 1a, using 4-amino-3-methoxy-benzoic acid as starting material. Yield: 160 mg (43.5%)

(b) Ethyl 2-[2-methoxy-4-[(1-methyl-3-piperidyl)carbamoyl]anilino]-5,6-dihydropyrimido[4,5-e]indolizine-7-carboxylate To a stirred suspension of 4-[(7-ethoxycarbonyl-5,6-dihydropyrimido[4,5-e]indolizin-2-yl)amino]-3-methoxybenzoic acid (80 mg, 0.20 mmol) and 3-amino-2-methylpiperidine dihydrochloride (36.6 mg, 0.20 mmol) in DMF (2 mL) was added DiPEA (139 µL, 0.84 mmol). The resulting solution was cooled to 0° C. and HATU (83.6 mg, 0.22 mmol) was added. The cooling was removed and the reaction mixture was stirred at room temperature o/n. The mixture was added dropwise to a vigorously stirred mixture of EtOAc/water/bring 1/1/1 (30 mL). The water layer was subsequently extracted with EtOAc (2×10 mL). The combined organic layers were washed with water (20 mL), bring (20 mL), dried over $Na_2SO_4$, filtered and concentrated in vacuo to give the title compound (70 mg, 70%).

(c) N-(2,6-dimethylphenyl)-2-[2-methoxy-4-[(1-methyl-3-piperidyl)carbamoyl]anilino]-5,6-dihydropyrimido[4,5-e]indolizine-7-carboxamide Saponification of crude ethyl 2-[2-methoxy-4-[(1-methyl-3-piperidyl)carbamoyl]anilino]-5,6-dihydropyrimido[4,5-3]indolizine-7-carboxylate and subsequent reaction with thionylchloride as described for Intermediate 2b afforded the corresponding acid chloride. The acid chloride was subsequently reacted with 2,6-diethylaniline according to procedure described in Example 2. Purification was performed using preparative HPLC to afford the title compound (8.4 mg, 19%). Data: LCMS (B) $R_t$: 11.406 min; m/z 580.3 $(M+H)^+$.

Example 61

N-(2,6-dichlorophenyl)-2-[2-methoxy-4-(4-methyl-piperazin-1-yl)anilino]-5,6-dihydropyrimido[4,5-e]indolizine-7-carboxamide This compound was prepared from its corresponding acid chloride, using the same sequence of reactions as described for Intermediate 2, using Intermediate F as starting material. The acid chloride was subsequently reacted with 2,6-dichloroaniline according to procedures described in Example 2. Purification was performed using preparative HPLC to afford the title compound (9 mg, 20.7%). Data: LCMS (B) $R_t$: 10.404 min; m/z 578.2 $(M+H)^+$ (chloride-pattern).

Intermediate 3

Ethyl 2-chloropyrimido[4,5-e]indolizine-7-carboxylate (a) Ethyl 2-methoxypyrimido[4,5-e]indolizine-7-carboxylate DDQ (1.53 g, 6.76 mmol) was added to a stirred solution of ethyl 2-methoxy-5,6-dihydropyrimido[4,5-e]indolizine-7-carboxylate (1.54 g, 5.63 mmol) in DCM (50 mL). The reaction mixture stirred for 3 days at room temperature. An additional amount of 200 mg DDQ was added and the reaction mixture was stirred for another 7 days at room temperature. The mixture was filtered and concentrated in vacuo to a small volume. The crude product was purified by column chromatography on silica (heptane/ethyl acetate=1/0 to 1/1 v/v %) to yield the title compound (750 mg, 50%).

(b) Ethyl 2-hydroxypyrimido[4,5-e]indolizine-7-carboxylate

Sodium iodide (1.24 g, 8.29 mmol) was added to a stirred solution of ethyl 2-methoxy-pyrimido[4,5-e]indolizine-7-carboxylate (750 mg, 2.76 mmol) in acetonitril (19 mL). A solution of trimethylsilyl chloride (896 mg, 1.05 mL) in acetonitrile (3 mL) was added dropwise to the reaction mixture. The reaction mixture was stirred at room temperature o/n. Additional sodium iodide (3.33 g) TMS-Cl (2.4 g, 2.8 mL) in acetonitrile (6 mL) were added dropwise and the reaction was stirred for 3 days at room temperature. The mixture was concentrated under reduced pressure. The residue was suspended in 200 mL DCM/MeOH (4/1) and extracted with a mixture of a saturated solution of sodium thiosulfate (50 mL) and water (100 mL). The water layer was extracted with DCM/MeOH (4/1, 2×150 mL). The combined organic layers were dried over sodium sulfate, filtered and the solvent was removed under reduced pressure to give a solid. The solid was triturated in boiling ethyl acetate (50 mL). After cooling the solid was stirred at 1 h at room temperature and filtered. The residue was dried at 40° C. under vacuum to give 1.0 g crude ethyl 2-hydroxy-5,6-dihydropyrimido[4,5-e]indolizine-7-carboxylate (quant. yield).

(c) Ethyl 2-chloropyrimido[4,5-e]indolizine-7-carboxylate (Intermediate 3)

N,N-Dimethylaniline (47 mg, 50 µL, 1.50 mmol) was added to a solution of ethyl 2-hydroxypyrimido[4,5-e]indolizine-7-carboxylate (1.0 g, 3.89 mmol) in acetonitrile (30 mL). A solution of phosphorus(V) oxychloride (2.99 g, 1.81 mL, 19.5 mmol) in acetonitrile (4 mL) was added dropwise to the reaction mixture. The brown/red suspension was heated to 65° C. for 4 hours. After cooling, the mixture was slowly poored in a stirred mixture of 25% aq. ammonia (50 mL) and ice-water (100 mL) keeping the temperature below 10° C. After stirring for another 15 minutes ethyl the mixture was extracted with ethyl acetate. The combined organic layers were, subsequently, washed with water (50 mL), 0.2 N HCl (50 mL), brine (25 mL), dried ($Na_2SO_4$), filtered and concentrated in vacuo. The crude product was purified by column chromatography on silica (heptane/ethyl acetate=1/0 to 1/1 v/v %) to yield 200 mg of the title compound.

Example 62

N-(2,6-dimethylphenyl)-2-[2-methoxy-4-[(1-methyl-4-piperidyl)oxy]anilino]pyrimido[4,5-e]indolizine-7-carboxamide This compound was prepared from its corresponding acid chloride, using the same sequence of reactions as described for Intermediate 2, starting from Intermediate 3 and Intermediate S as starting material. The acid chloride was subsequently reacted with 2,6-dimethylaniline according to procedures described in Example 2. Purification was performed using preparative HPLC to afford the title compound (30 mg, 45%). Data: LCMS (B) $R_t$: 12.491 min; m/z 551.3 $(M+H)^+$.

Example 63

N-(2,6-dimethylphenyl)-2-[2-methyl-4-(4-methyl-piperazin-1-yl)anilino]-5,6-dihydropyrimido[4,5-e]indolizine-7-carboxamide This compound was prepared from its corresponding acid chloride, using the same sequence of reactions as described

Example 64

N-(2-ethyl-6-methyl-phenyl)-2-[2-methyl-4-(4-methylpiperazin-1-yl)anilino]-5,6-dihydropyrimido[4,5-e]indolizine-7-carboxamide This compound was prepared from its corresponding acid chloride, using the same sequence of reactions as described for Intermediate 2, using Intermediate B as starting material. The acid chloride was subsequently reacted with 2-ethyl-6-methylaniline according to procedures described in Example 2. Purification was performed using preparative HPLC to afford the title compound (14 mg, 65%). Data: LCMS (B) $R_t$: 10.303 min; m/z 536.3 (M+H)$^+$.

Example 65

N-(2-bromo-6-methyl-phenyl)-2-[2-methyl-4-(4-methylpiperazin-1-yl)anilino]-5,6-dihydropyrimido[4,5-e]indolizine-7-carboxamide This compound was prepared from its corresponding acid chloride, using the same sequence of reactions as described for Intermediate 2, using Intermediate B as starting material. The acid chloride was subsequently reacted with 2-bromo-6-methylaniline according to procedures described in Example 2. Purification was performed using preparative HPLC to afford the title compound (30 mg, 73%). Data: LCMS (B) $R_t$: 9.914 min; m/z 586.2/588.2 (M+H)$^+$ (bromide pattern).

Example 66

N-(2,6-dichlorophenyl)-2-[2-methyl-4-(4-methylpiperazin-1-yl)anilino]-5,6-dihydropyrimido[4,5-e]indolizine-7-carboxamide This compound was prepared from its corresponding acid chloride, using the same sequence of reactions as described for Intermediate 2, using Intermediate B as starting material. The acid chloride was subsequently reacted with 2,6-dichloroaniline according to procedures described in Example 2. Purification was performed using preparative HPLC to afford the title compound (10 mg, 36%). Data: LCMS (B) $R_t$: 9.770 min; m/z 562.2 (M+H)$^+$ (chloride-pattern).

Example 67

N-(2,6-diethylphenyl)-2-[2-methyl-4-(4-methylpiperazin-1-yl)anilino]-5,6-dihydropyrimido[4,5-e]indolizine-7-carboxamide This compound was prepared from its corresponding acid chloride, using the same sequence of reactions as described for Intermediate 2, using Intermediate B as starting material. The acid chloride was subsequently reacted with 2,6-diethylaniline according to procedures described in Example 2. Purification was performed using preparative HPLC to afford the title compound (13 mg, 34%). Data: LCMS (B) $R_t$: 10.954 min; m/z 550.3 (M+H)$^+$.

Example 68

N-(2,6-dimethylphenyl)-2-[(2-methyl-6-morpholino-3-pyridyl)amino]-5,6-dihydropyrimido[4,5-e]indolizine-7-carboxamide This compound was prepared from its corresponding acid chloride, using the same sequence of reactions as described for Intermediate 2, using Intermediate D as starting material. The acid chloride was subsequently reacted with 2,6-dimethylaniline according to procedures described in Example 2. Purification was performed using preparative HPLC to afford the title compound (9.6 mg, 27%). Data: LCMS (B) $R_t$: 10.844 min; m/z 510.2 (M+H)$^+$.

Example 69

N-(2-ethyl-6-methyl-phenyl)-2-[(2-methyl-6-morpholino-3-pyridyl)amino]-5,6-dihydropyrimido[4,5-e]indolizine-7-carboxamide This compound was prepared from its corresponding acid chloride, using the same sequence of reactions as described for Intermediate 2, using Intermediate D as starting material. The acid chloride was subsequently reacted with 2-ethyl-6-methylaniline according to procedures described in Example 2. Purification was performed using preparative HPLC to afford the title compound (11.2 mg, 30.4%). Data: LCMS (B) $R_t$: 11.599 min; m/z 524.3 (M+H)$^+$.

Example 70

N-(2-bromo-6-methyl-phenyl)-2-[(2-methyl-6-morpholino-3-pyridyl)amino]-5,6-dihydropyrimido[4,5-e]indolizine-7-carboxamide This compound was prepared from its corresponding acid chloride, using the same sequence of reactions as described for Intermediate 2, using Intermediate D as starting material. The acid chloride was subsequently reacted with 2-bromo-6-methylaniline according to procedures described in Example 2. Purification was performed using preparative HPLC to afford the title compound (12 mg, 30%). Data: LCMS (B) $R_t$: 11.151 min; m/z 574.2/576.2 (M+H)$^+$ (bromide pattern).

Example 71

N-(2,6-diethylphenyl)-2-[2-methoxy-4-(4-methylpiperazin-1-yl)anilino]pyrimido[4,5-e]indolizine-7-carboxamide This compound was prepared from its corresponding acid chloride, using the same sequence of reactions as described for Intermediate 2, using Intermediate 3 and Intermediate F as starting material. The acid chloride was subsequently reacted with 2,6-diethylaniline according to procedures described in Example 2. Purification was performed using preparative HPLC to afford the title compound (0.7 mg). Data: LCMS (A) $R_t$: 6.446 min; m/z 564.3 (M+H)$^+$.

Example 72

N-(2-ethyl-6-methyl-phenyl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions as described for Intermediate 2, using Intermediate F as starting material. The acid chloride was subsequently reacted with 2-ethyl-6-methylaniline according to procedures described in Example 2. Purification was performed using preparative HPLC to afford the title compound (17.8 mg, 32.2%). Data: LCMS (B) $R_t$: 10.836 min; m/z 552.3 (M+H)$^+$.

Example 73

N-(2-bromo-6-methyl-phenyl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions as described for Intermediate 2, using Intermediate F as starting material. The acid chloride was subsequently reacted with 2-bromo-6-methylaniline according to procedures described in Example 2. Purification was performed using preparative HPLC to afford the title compound (18.1 mg, 30%). Data: LCMS (B) $R_t$: 10.427 min; m/z 602.2/604.2 (M+H)$^+$ (bromide pattern).

Example 74

N-(2,6-dimethylphenyl)-2-(2-methoxy-4-piperazin-1-yl-anilino)pyrimido[4,5-e]indolizine-7-carboxamide carboxamide This compound was prepared from its corresponding ethyl ester, using the same sequence of reactions as described for Example 1, starting from Intermediate 3 and Intermediate H as starting material. The ethyl ester was subsequently reacted with 2,6-dimethylaniline according to procedures described in Example 1. After deprotection of the Boc-group using 50% TFA/dichloromethane, purification was performed using preparative HPLC to afford the title compound (1.4 mg, 5%). Data: LCMS (B) $R_t$: 10.283 min; m/z 524.3 (M+H)$^+$.

Example 75

N-(2-chloro-6-methyl-phenyl)-2-(2-methoxy-4-piperazin-1-yl-anilino)-5,6-dihydropyrimido[4,5-e]indolizine-7-carboxamide This compound was prepared from its corresponding ethyl ester, using the same sequence of reactions as described for Example 1, starting from Intermediate 1 and Intermediate H as starting material. The ethyl ester was subsequently reacted with 2-chloro-6-methylaniline according to procedures described in Example 1. After deprotection of the Boc-group using 50% TFA/dichloromethane, purification was performed using preparative HPLC to afford the title compound (0.9 mg, 4%). Data: LCMS (A) $R_t$: 5.794 min; m/z 544.2/546.2 (M+H)$^+$ (chloride pattern).

Example 76

N-(2,6-diethylphenyl)-2-(2-methoxy-4-piperazin-1-yl-anilino)-5,6-dihydropyrimido[4,5-e]indolizine-7-carboxamide This compound was prepared from its corresponding ethyl ester, using the same sequence of reactions as described for Example 1, starting from Intermediate 1 and Intermediate H as starting material. The ethyl ester was subsequently reacted with 2,6-diethylaniline according to procedures described in Example 1. After deprotection of the Boc-group using 50% TFA/dichloromethane, purification was performed using preparative HPLC to afford the title compound (20.7 mg, 72%). Data: LCMS (A) $R_t$: 6.213 min; m/z 552.3 (M+H)$^+$.

Example 77

N-(2,6-diethylphenyl)-2-(2-methoxy-4-piperazin-1-yl-anilino)pyrimido[4,5-e]indolizine-7-carboxamide This compound was isolated as a side product during preparative HPLC purification of Example 76 to afford the title compound (2 mg, 7%). Data: LCMS (A) $R_t$: 6.512 min; m/z 550.3 (M+H)$^+$.

Example 78

N-(2-chloro-6-methyl-phenyl)-2-(2-methyl-4-piperazin-1-yl-anilino)-5,6-dihydropyrimido[4,5-e]indolizine-7-carboxamide This compound was prepared from its corresponding acid chloride, using the same sequence of reactions as described for Intermediate 2, using Intermediate I as starting material. The acid chloride was subsequently reacted with 2-chloro-6-methylaniline according to procedures described in Example 2. After deprotection of the Cbz-group, purification was performed using preparative HPLC to afford the title compound (24 mg, 81%). Data: LCMS (B) $R_t$: 9.831 min; m/z 528.2/530.2 (M+H)$^+$ chloride pattern.

Example 79

N-(2,6-dichlorophenyl)-2-(2-methyl-4-piperazin-1-yl-anilino)-5,6-dihydropyrimido[4,5-e]indolizine-7-carboxamide This compound was prepared from its corresponding acid chloride, using the same sequence of reactions as described for Intermediate 2, using Intermediate I as starting material. The acid chloride was subsequently reacted with 2,6-dichloroaniline according to procedures described in Example 2. After deprotection of the Cbz-group, purification was performed using preparative HPLC to afford the title compound (27 mg, 96%). Data: LCMS (B) $R_t$: 9.853 min; m/z 548.2 (M+H)$^+$ (chloride-pattern).

Example 80

N-(2,6-diethylphenyl)-2-(2-methyl-4-piperazin-1-yl-anilino)-5,6-dihydropyrimido[4,5-e]indolizine-7-carboxamide This compound was prepared from its corresponding acid chloride, using the same sequence of reactions as described for Intermediate 2, using Intermediate I as starting material. The acid chloride was subsequently reacted with 2,6-diethylaniline according to procedures described in Example 2. After deprotection of the Cbz-group, purification was performed using preparative HPLC to afford the title compound (18 mg, 40%). Data: LCMS (B) $R_t$: 10.916 min; m/z 536.3 (M+H)$^+$.

Example 81

N-(2-bromo-6-methyl-phenyl)-2-(2-methyl-4-piperazin-1-yl-anilino)-5,6-dihydropyrimido[4,5-e]indolizine-7-carboxamide This compound was prepared from its corresponding acid chloride, using the same sequence of reactions as described for Intermediate 2, using Intermediate I as starting material. The acid chloride was subsequently reacted with 2-bromo-6-methylaniline according to procedures described in Example 2. After deprotection of the Cbz-group, purification was performed using preparative HPLC to afford the title compound (16 mg, 51%). Data: LCMS (B) $R_t$: 9.922 min; m/z 572.2/574.2 (M+H)$^+$ (bromide pattern).

Example 82

N-(2-ethyl-6-methyl-phenyl)-2-(2-methyl-4-piperazin-1-yl-anilino)-5,6-dihydropyrimido[4,5-e]indolizine-7-carboxamide This compound was prepared from its corresponding acid chloride, using the same sequence of reactions as described for Intermediate 2, using Intermediate I as starting material. The acid chloride was subsequently reacted with 2-ethyl-6-methylaniline according to procedures described in Example 2. After deprotection of the Cbz-group, purification was performed using preparative HPLC to afford the title (22 mg, 77%). Data: LCMS (B) $R_t$: 10.361 min; m/z 522.3 (M+H)$^+$.

Example 83

N-(2,6-diethylphenyl)-2-(2-methyl-4-morpholino-anilino)-5,6-dihydropyrimido[4,5-e]indolizine-7-carboxamide This compound was prepared from its corresponding ethyl ester, using the same sequence of reactions as described for Intermediate 2a, using Intermediate W. The ester was subsequently reacted with 2,6-diethylaniline according to procedures described in Example 1b. Purification was performed using preparative HPLC to afford the title compound (4.2 mg, 13%). Data: LCMS (B) $R_t$: 15.695 min; m/z 537.3 (M+H)$^+$.

Example 84

N-(2,6-dimethylphenyl)-2-[2-methoxy-4-(1-methyl-pyrrolidin-3-yl)oxy-anilino]-5,6-dihydropyrimido[4,5-e]indolizine-7-carboxamide This compound was prepared from its corresponding acid chloride, using the same sequence of reactions as described for Intermediate 2, using Intermediate Y as starting material. The acid chloride was subsequently reacted with 2,6-dimethylaniline according to procedures described in Example 2. Purification was performed using preparative HPLC to afford the title compound (4 mg, 12%). Data: LCMS (B) $R_t$: 10.832 min; m/z 539.2 (M+H)$^+$.

Example 85

N-[1-(2-methoxyethyl)-3,5-dimethyl-pyrazol-4-yl]-2-[4-(1-methyl-4-piperidyl)anilino]-5,6-dihydropyrimido[4,5-e]indolizine-7-carboxamide This compound was prepared from its corresponding acid chloride, using the same sequence of reactions, as described for Intermediate 2, using commercially available 4-(1-methyl-piperidin-4-yl)-aniline as starting material. The acid chloride was subsequently reacted with Intermediate Aa according to procedures described in Example 2. Purification was performed using preparative HPLC to afford the title compound (18.3 mg, 44%). Data: LCMS (B) $R_t$: 8.405 min; m/z 555.3 (M+H)$^+$.

Example 86

N-(2-chloro-6-methyl-phenyl)-2-[2-(difluoromethoxy)-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate J as starting material. The acid chloride was subsequently reacted with 2-chloro-6-methylaniline according to procedures described in Example 2. Purification was performed using preparative HPLC to afford the title compound (17.2 mg, 41%). Data: LCMS (B) $R_t$: 11.569 min; m/z 594.2/596.2 (M+H)$^+$ (chloride-pattern).

Example 87

N-(2,6-diethylphenyl)-2-[2-ethyl-4-(4-methylpiperazin-1-yl)anilino]-5,6-dihydropyrimido[4,5-e]indolizine-7-carboxamide This compound was prepared from its corresponding bromide, using the same sequence of reactions, as described for Example 38-a, using 4-bromo-2-ethylaniline as starting material. The bromide was subsequently reacted with N-methylpiperazine according to procedures described in Example 38-b. Purification was performed using preparative HPLC to afford the title compound (6.5 mg, 15%). Data: LCMS (B) $R_t$: 12.136 min; m/z 564.4 (M+H)$^+$.

Example 88

N-[3,5-diethyl-1-(2-methoxyethyl)pyrazol-4-yl]-2-[4-[3-(dimethylamino)propyl-methyl-carbamoyl]-2-methoxy-anilino]-5,6-dihydropyrimido[4,5-e]indolizine-7-carboxamide This compound was prepared from its corresponding acid chloride, using the same sequence of reactions, as described for Example 60, using N,N,N'-trimethyl-1,3-propanediamine as starting material. The acid chloride was subsequently reacted with Intermediate Ae according to procedures described in Example 2. Purification was performed using preparative HPLC to afford the title compound (13.8 mg, 20%). Data: LCMS (B) $R_t$: 10.220 min; m/z 658.4 (M+H)$^+$.

Example 89

2-[4-(azetidin-3-yloxy)-2-methyl-anilino]-N-[1-(2-methoxyethyl)-3,5-dimethyl-pyrazol-4-yl]-5,6-dihydropyrimido[4,5-e]indolizine-7-carboxamide This compound was prepared from its corresponding acid chloride, using the same sequence of reactions, as described for Intermediate 2, using Intermediate Z as starting material. The acid chloride was subsequently reacted with Intermediate Aa according to procedures described in Example 2. After deprotection of the Cbz-group, purification was performed using preparative HPLC to afford the title compound (6.6 mg, 17%). Data: LCMS (B) $R_t$: 7.975 min; m/z 543.3 $(M+H)^+$.

Example 90

2-[4-(3,5-Dimethylsoxazol-4-yl)-2-methoxy-anilino]-N-[1-(2-methoxyethyl)-3,5-dimethyl-pyrazol-4-yl]-5,6-dihydropyrimido[4,5-e]indolizine-7-carboxamide This compound was prepared from its corresponding acid chloride, using the same sequence of reactions, as described for Intermediate 2, using Intermediate ZA as starting material. The acid chloride was subsequently reacted with Intermediate Aa according to procedures described in Example 2. Purification was performed using preparative HPLC to afford the title compound (16.2 mg, 46%). Data: LCMS (B) $R_t$: 14.477 min; m/z 583.3 $(M+H)^+$.

Example 91

2-[4-(Azetidin-3-yloxy)-2-methoxy-anilino]-N-[1-(2-methoxyethyl)-3,5-dimethyl-pyrazol-4-yl]-5,6-dihydropyrimido[4,5-e]indolizine-7-carboxamide This compound was prepared from its corresponding acid chloride, using the same sequence of reactions, as described for Intermediate 2, using Intermediate ZB as starting material. The acid chloride was subsequently reacted with Intermediate Aa according to procedures described in Example 2. After deprotection of the Cbz-group, purification was performed using preparative HPLC to afford the title compound (12.8 mg, 25%). Data: LCMS (B) $R_t$: 8.441 min; m/z 559.3 $(M+H)^+$.

Example 92

2-[4-(Azetidin-3-yloxy)-2-methoxy-anilino]-N-(3,5-diethyl-pyrazol-4-yl)-5,6-dihydropyrimido[4,5-e]indolizine-7-carboxamide This compound was prepared from its corresponding acid chloride, using the same sequence of reactions, as described for Intermediate 2, using Intermediate ZB as starting material. The acid chloride was subsequently reacted with Intermediate Ac according to procedures described in Example 2. After deprotection of the Cbz-group, purification was performed using preparative HPLC to afford the title compound (8.9 mg, 19%). Data: LCMS (B) $R_t$: 8.324 min; m/z 529.3 $(M+H)^+$.

Example 93

2-[4-(Azetidin-3-yloxy)-2-methoxy-anilino]-N-[3,5-diethyl-1-(2-methoxyethyl)pyrazol-4-yl]-5,6-dihydropyrimido[4,5-e]indolizine-7-carboxamide This compound was prepared from its corresponding acid chloride, using the same sequence of reactions, as described for Intermediate 2, using Intermediate ZB as starting material. The acid chloride was subsequently reacted with Intermediate Ae according to procedures described in Example 2. After deprotection of the Cbz-group, purification was performed using preparative HPLC to afford the title compound (14.9 mg, 34%). Data: LCMS (B) $R_t$: 9.618 min; m/z 587.4 $(M+H)^+$.

Example 94

N-[1-(2-methoxyethyl)-3,5-dimethyl-pyrazol-4-yl]-2-[2-methoxy-4-(1,3,5-trimethylpyrazol-4-yl)anilino]-5,6-dihydropyrimido[4,5-e]indolizine-7-carboxamide This compound was prepared from its corresponding acid chloride, using the same sequence of reactions, as described for Intermediate 2, using Intermediate R as starting material. The acid chloride was subsequently reacted with Intermediate Aa according to procedures described in Example 2. Purification was performed using preparative HPLC to afford the title compound (8.7 mg, 21%). Data: LCMS (B) $R_t$: 12.704 min; m/z 596.3 $(M+H)^+$.

Example 95

N-[1-(2-methoxyethyl)-3,5-dimethyl-pyrazol-4-yl]-2-[2-methoxy-4-yl]-2-[2-methoxy-4-[(1-methyl-4-piperidyl)oxy]anilino]pyrimido[4,5-e]indolizine-7-carboxamide This compound was prepared from its corresponding acid chloride, using the same sequence of reactions, as described for Intermediate 2, starting from Intermediate 3 and Intermediate S as starting material. The acid chloride was subsequently reacted with Intermediate Aa according to procedures described in Example 2. Purification was performed using preparative HPLC to afford the title compound (23 mg, 32%). Data: LCMS (B) $R_t$: 9.796 min; m/z 599.3 $(M+H)^+$.

Example 96

N-[1-(2-methoxyethyl)-3,5-dimethyl-pyrazol-4-yl]-2-(2-methoxy-4-piperazin-1-yl-anilino)pyrimido[4,5-e]indolizine-7-carboxamide This compound was prepared from its corresponding acid chloride, using the same sequence of reactions, as described for Intermediate 2, starting from Intermediate 3 and Intermediate ZE as starting material. The acid chloride was subsequently reacted with Intermediate Aa according to procedures described in Example 2. After deprotection of the Cbz-group, purification was performed using preparative

Example 97

N-(3,5-diethyl-1H-pyrazol-4-yl)-2-(2-methoxy-4-piperazin-1-yl-anilino)pyrimido[4,5-e]indolizine-7-carboxamide This compound was prepared from its corresponding acid chloride, using the same sequence of reactions, as described for Intermediate 2, starting from Intermediate 3 and Intermediate ZE as starting material. The acid chloride was subsequently reacted with Intermediate Ac according to procedures described in Example 2. After deprotection of the Cbz-group, purification was performed using preparative HPLC to afford the title compound (10.6 mg, 39%). Data: LCMS (B) $R_t$: 8.908 min; m/z 540.3 (M+H)$^+$.

Example 98

N-[1-(2-hydroxy-2-methyl-propyl)-3,5-dimethyl-pyrazol-4-yl]-2-(2-methoxy-4-piperazin-1-yl-anilino)-5,6-dihydropyrimido[4,5-e]indolizine-7-carboxamide This compound was prepared from its corresponding acid chloride, using the same sequence of reactions, as described for Intermediate 2, using Intermediate ZE as starting material. The acid chloride was subsequently reacted with Intermediate Af according to procedures described in Example 2. After deprotection of the Cbz-group, purification was performed using preparative HPLC to afford the title compound (11.4 mg, 28%). Data: LCMS (B) $R_t$: 7.882 min; m/z 586.3 (M+H)$^+$.

Example 99

N-(2,6-diethylphenyl)-2-[4-(4-methylpiperazin-1-yl)-2-(trideuteriomethoxy)anilino]-5,6-dihydropyrimido[4,5-e]indolizine-7-carboxamide This compound was prepared from its corresponding acid chloride, using the same sequence of reactions, as described for Intermediate 2, using Intermediate ZC as starting material. The acid chloride was subsequently reacted with 2,6-diethylaniline according to procedures described in Example 2. Purification was performed using preparative HPLC to afford the title compound (14.6 mg, 23%). Data: LCMS (B) $R_t$: 12.878 min; m/z 569.4 (M+H)$^+$.

Example 100

N-[3,5-diethyl-1-(2-methoxyethyl)pyrazol-4-yl]-2-[4-(4-methylpiperazin-1-yl)-2-(trideuteriomethoxy)anilino]-5,6-dihydropyrimido[4,5-e]indolizine-7-carboxamide This compound was prepared from its corresponding acid chloride, using the same sequence of reactions, as described for Intermediate 2, using Intermediate ZC as starting material. The acid chloride was subsequently reacted with Intermediate Ae according to procedures described in Example 2. Purification was performed using preparative HPLC to afford the title compound (17.2 mg, 25%). Data: LCMS (B) $R_t$: 9.443 min; m/z 617.4 (M+H)$^+$.

HPLC to afford the title compound (14 mg, 61%). Data: LCMS (B) $R_t$: 9.058 min; m/z 570.3 (M+H)$^+$.

Example 101

N-[1-(2-methoxyethyl)-3,5-dimethyl-pyrazol-4-yl]-2-[[2-methyl-6-(4-methylpiperazin-1-yl)-3-pyridyl]amino]-5,6-dihydropyrimido[4,5-e]indolizine-7-carboxamide This compound was prepared from its corresponding acid chloride, using the same sequence of reactions, as described for Intermediate 2, using Intermediate ZD as starting material. The acid chloride was subsequently reacted with Intermediate Aa according to procedures described in Example 2. Purification was performed using preparative HPLC to afford the title compound (13.8 mg, 27%). Data: LCMS (B) $R_t$: 7.187 min; m/z 571.4 (M+H)$^+$.

Example 102

2-[5-Chloro-2-methoxy-4-(4-methylpiperazin-1-yl)anilino]-N-(2,6-diethylphenyl)-5,6-dihydropyrimido[4,5-e]indolizine-7-carboxamide This compound was isolated as a side product from the compound described in Example 20 using preparative HPLC to afford the title compound (9.1 mg). Data: LCMS (B) $R_t$: 14.555 min; m/z 601.3/603.3 (M+H)$^+$ (chloride-pattern).

Example 103

N-(2,6-dimethylphenyl)-2-[2-methoxy-4-(tetrahydropyran-4-ylcarbamoyl)anilino]-5,6-dihydropyrimido[4,5-e]indolizine-7-carboxamide (a) 2-(4-Bromo-2-methoxy-anilino)-N-(2,6-dimethylphenyl)-5,6-dihydropyrimido[4,5-e]indolizine-7-carboxamide This compound was prepared from its corresponding acid chloride, using the same sequence of reactions, as described for Intermediate 2, using commercially available 4-bromo-2-methoxyaniline as starting material. The acid chloride was subsequently reacted with 2,6-dimethylaniline according to procedures described in Example 2 to afford the title compound (1.35 g, 84%).

(b) 2-(4-Cyano-2-methoxy-anilino)-N-(2,6-dimethylphenyl)-5,6-dihydropyrimido[4,5-e]indolizine-7-carboxamide To a solution of 2-(4-bromo-2-methoxy-anilino)-N-(2,6-dimethylphenyl)-5,6-dihydropyrimido[4,5-e]indolizine-7-carboxamide (1.35 g, 2.6 mmol) and zinc cyanide (321 mg, 2.73 mmol) in DMF (4 mL) was added tetrakis(triphenylphosphine)palladium (0) (300 mg, 0.26 mmol). The reaction mixture was heated for 30 minutes at 170° C. under microwave radiation. After cooling to ambient temperature, the mixture was concentrated and the residue was diluted with ethyl acetate, washed with water and brine, dried over sodium sulfate, filtered and concentrated in vacuo to afford the crude title compound (1.05 g, 87%).

(c) 4-[[7-[(2,6-Dimethylphenyl)carbamoyl-]-5,6-dihydropyrimido[4,5-e]indolizin-2-yl]amino]-3-methoxy-benzoic acid To a stirred suspension of 2-(4-cyano-2-methoxy-anilino)-N-(2,6-dimethylphenyl)-5,6-dihydropyrimido[4,5-e]

indolizine-7-carboxamide (750 mg, 1.61 mmol) in MeOH (25 mL) was added a solution of potassium hydroxide (453 mg, 8.07 mmol) in water (12.5 mL). The reaction mixture was heated for 2 hours at 120° C. under microwave radiation. After evaporation of the methanol fraction, the resulting water layer was acidified by addition of 2N HCl-solution until pH~2. After extraction with dichloromethane, the combined organic layers were filtered over a PE-filter to give 330 mg of the title compound (yield: 42%).

(d) N-(2,6-dimethylphenyl)-2-[2-methoxy-4-(tetrahydropyran-4-ylcarbamoyl)anilino]-5,6-dihydropyrimido[4,5-e]indolizine-7-carboxamide This compound was prepared from its corresponding carboxylic acid (Example 103-c) and 4-aminotetrahydropyran hydrochloride, using standard HATU-coupling procedures as described in Example 9. Purification was performed using preparative HPLC to afford the title compound (5 mg, 18%). Data: LCMS (B) $R_t$: 14.407 min; m/z 567.3 $(M+H)^+$.

Example 104

2-[4-(Azetidin-3-ylcarbamoyl)-2-methoxy-anilino]-N-(2,6-dimethylphenyl)-5,6-dihydropyrimido[4,5-e]indolizine-7-carboxamide This compound was prepared from its corresponding carboxylic acid (Example 103-c) and 3-amino-1-N-Boc-azetidine, using standard HATU-coupling procedures as described in Example 9. After deprotection of the Boc-group, purification was performed using preparative HPLC to afford the title compound (6.8 mg, 20%). Data: LCMS (B) $R_t$: 11.597 min; m/z 538.3 $(M+H)^+$.

Example 105

N-(2,6-dimethylphenyl)-2-[2-methoxy-4-[4-(2-methoxyacetyl)piperazin-1-yl]anilino]-5,6-dihydropyrimido[4,5-e]indolizine-7-carboxamide This compound was prepared from its corresponding amine (Example 17) and methoxyacetic acid, using standard HATU-coupling procedures as described in Example 9. Purification was performed using preparative HPLC to afford the title compound (10 mg, 49%). Data: LCMS (B) $R_t$: 12.973 min; m/z 596.3 $(M+H)^+$.

Example 106

N-[1-(2-methoxyethyl)-3,5-dimethyl-pyrazol-4-yl]-2-[[4-methoxy-2-(4-methylpiperazin-1-yl)pyrimidin-5-yl]amino]-5,6-dihydropyrimido[4,5-e]indolizine-7-carboxamide This compound was prepared from its corresponding acid chloride, using the same sequence of reactions, as described for Intermediate 2, using Intermediate ZF as starting material. The acid chloride was subsequently reacted with Intermediate Aa according to procedures described in Example 2. Purification was performed using preparative HPLC to afford the title compound (5.9 mg, 20%). Data: LCMS (B) $R_t$: 7.658 min; m/z 588.4 $(M+H)^+$.

Example 107

N-(2,6-diethylphenyl)-2-[[4-methoxy-2-(4-methylpiperazin-1-yl)pyrimidin-5-yl]amino]-5,6-dihydropyrimido[4,5-e]indolizine-7-carboxamide This compound was prepared from its corresponding acid chloride, using the same sequence of reactions, as described for Intermediate 2, using Intermediate ZF as starting material. The acid chloride was subsequently reacted with 2,6-diethylaniline according to procedures described in Example 2. Purification was performed using preparative HPLC to afford the title compound (3.1 mg, 11%). Data: LCMS (B) $R_t$: 12.119 min; m/z 568.4 $(M+H)^+$.

Example 108

N-(3-ethyl-5-methyl-isoxazol-4-yl)-2-[2-methoxy-4-(4-methylpiperazin-1-yl)anilino]-5,6-dihydropyrimido[4,5-e]indolizine-7-carboxamide This compound was prepared from its corresponding carboxylic acid, using the same sequence of reactions as described for Intermediate 2, using Intermediate F as starting material. The carboxylic acid was subsequently reacted with Intermediate Ag in an analogous manner as described in Example 9. Purification was performed using preparative HPLC to afford the title compound (11.3 mg, 45%). Data: LCMS (B) $R_t$: 9.102 min; m/z 543.3 $(M+H)^+$.

Example 109

N-[3,5-diethyl-1-(2-methoxyethyl)pyrazol-4-yl]-2-[2-methoxy-4-(4-methylpiperazin-1-yl)anilino]-5,6-dihydropyrimido[4,5-e]indolizine-7-carboxamide This compound was prepared from its corresponding carboxylic acid, using the same sequence of reactions as described for Intermediate 2, using Intermediate F as starting material. The carboxylic acid was subsequently reacted with Intermediate Ae in an analogous manner as described for Example 9. Purification was performed using preparative HPLC to afford the title compound (21.5 mg, 76%). Data: LCMS (B) $R_t$: 9.108 min; m/z 614.4 $(M+H)^+$.

Example 110

(N-(2,6-dimethylphenyl)-2-[4-[4-(3-fluorocyclobutanecarbonyl)piperazin-1-yl]-2-methoxy-anilino]-5,6-dihydropyrimido[4,5-e]indolizine-7-carboxamide This compound was prepared from its corresponding amine (Example 17) and 3-fluorocyclo-butanecarboxylic acid, using standard HATU-coupling procedures as described in Example 9. Purification was performed using preparative HPLC to afford the title compound (26 mg, 99%). Data: LCMS (B) $R_t$: 15.532 min; m/z 624.3 $(M+H)^+$.

Example 111

(N-(2,6-dimethylphenyl)-2-[2-methoxy-4-[4-(3-methyloxetane-3-carbonyl)piperazin-1-yl]anilino]-5,6-dihydropyrimido[4,5-e]indolizine-7-carboxamide This compound was prepared from its corresponding amine (Example 17) and 3-methyl-oxetane-3-carboxylic acid, using standard HATU-coupling procedures as described in Example 9. Purification was performed using preparative HPLC to afford the title compound (4 mg, 17%). Data: LCMS (B) $R_t$: 13.824 min; m/z 622.3 (M+H)$^+$.

Example 112

2-[4-[4-(Cyclopropanecarbonyl)piperazin-1-yl]-2-methoxy-anilino]-N-(2,6-dimethylphenyl)-5,6-dihydropyrimido[4,5-e]indolizine-7-carboxamide This compound was prepared from its corresponding amine (Example 17) and cyclopropane-carboxylic acid, using standard HATU-coupling procedures as described in Example 9. Purification was performed using preparative HPLC to afford the title compound (11 mg, 49%). Data: LCMS (B) $R_t$: 14.744 min; m/z 592.3 (M+H)$^+$.

Example 113

2-[4-(4-Butylsulfonylpiperazin-1-yl)-2-methoxy-anilino]-N-(2,6-dimethylphenyl)-5,6-dihydropyrimido[4,5-e]indolizine-7-carboxamide To a stirred solution of N-(2,6-dimethylphenyl)-2-(2-methoxy-4-piperazin-1-yl-anilino)-5,6-dihydropyrimido[4,5-e]indolizine-7-carboxamide (Example 17, 20 mg, 0.038 mmol) in DCM (2 mL) was added triethylamine (18 μL, 0.13 mmol) and butane-1-sulfonyl chloride (5 μL, 0.042 mmol). The reaction mixture was stirred o/n at room temperature, the mixture was concentrated and the residue was purified using preparative HPLC to afford the title compound (3 mg, 13%). Data: LCMS (B) $R_t$: 17.533 min; m/z 644.3 (M+H)$^+$.

Example 114

N-(2,6-dimethylphenyl)-2-[4-[4-(ethylcarbamoyl) piperazin-1-yl]-2-methoxy-anilino]-5,6-dihydropyrimido[4,5-e]indolizine-7-carboxamide To a stirred solution of N-(2,6-dimethylphenyl)-2-(2-methoxy-4-piperazin-1-yl-anilino)-5,6-dihydropyrimido[4,5-e]indolizine-7-carboxamide (Example 17, 20 mg, 0.038 mmol) in DCM (2 ml) was added isocyanatoethane (4 μL, 0.042 mmol). The reaction mixture was stirred o/n at room temperature. The mixture was concentrated and the residue was purified using preparative HPLC to afford the title compound (24 mg, 99%). Data: LCMS (B) $R_t$: 13.414 min; m/z 595.3 (M+H)$^+$.

Example 115

N-[1-(2-methoxyethyl)-3,5-dimethyl-pyrazol-4-yl]-2-[2-methoxy-5-methyl-4-(4-methylpiperazin-1-yl) anilino]-5,6-dihydropyrimido[4,5-e]indolizine-7-carboxamide This compound was prepared from its corresponding acid chloride, using the same sequence of reactions, as described for Intermediate 2, using Intermediate ZG as starting material. The acid chloride was subsequently reacted with Intermediate Aa according to procedures described in Example 2. Purification was performed using preparative HPLC to afford the title compound (19.2 mg, 29%). Data: LCMS (B) $R_t$: 9.296 min; m/z 600.4 (M+H)$^+$.

Example 116

N-(2,6-diethylphenyl)-2-[2-methoxy-4-(3-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate ZH as starting material. The acid chloride was subsequently reacted with 2,6-diethylaniline according to procedures described in Example 2. After deprotection of the Cbz-group, purification was performed using preparative HPLC to afford the title compound (12.2 mg, 17%). Data: LCMS (B) $R_t$: 12.915 min; m/z 566.4 (M+H)$^+$.

Example 117

N-(2,6-dimethylphenyl)-2-[2-methoxy-4-[[(3S,4R)-3-methoxy-4-piperidyl]carbamoyl]anilino]-5,6-dihydropyrimido[4,5-e]indolizine-7-carboxamide This compound was prepared from its corresponding carboxylic acid (Example 103-c) and (3S,4R)-4-amino-1-Boc-3-methoxy-piperidine, using standard HATU-coupling procedures as described in Example 9. After deprotection of the Boc-group, purification was performed using preparative HPLC to afford the title compound (2.7 mg, 7%). Data: LCMS (B) $R_t$: 11.799 min; m/z 596.4 (M+H)$^+$.

Example 118

N-(2,6-dimethylphenyl)-2-[4-[[(3S,4R)-3-fluoro-4-piperidyl]carbamoyl]-2-methoxy-anilino]-5,6-dihydropyrimido[4,5-e]indolizine-7-carboxamide This compound was prepared from its corresponding carboxylic acid (Example 103-c) and tert-butyl (3S,4R)-4-amino-3-fluoro-piperidine-1-carboxylate, using standard HATU-coupling procedures as described in Example 9. After deprotection of the Boc-group, purification was performed using preparative HPLC to afford the title compound (2.2 mg, 5%). Data: LCMS (B) $R_t$: 11.671 min; m/z 584.3 (M+H)$^+$.

Example 119

2-[4-[(4-cis-Aminocyclohexyl)carbamoyl]-2-methoxy-anilino]-N-(2,6-dimethylphenyl)-5,6-dihydropyrimido[4,5-e]indolizine-7-carboxamide This compound was prepared from its corresponding carboxylic acid (Example 103-c) and 1-N-Boc-cis-1,4-cyclohexyldiamine hydrochloride, using standard HATU-coupling procedures as described in Example 9. After deprotection of the Boc-group, purification was performed using preparative HPLC to afford the title compound (4.6 mg, 15%). Data: LCMS (B) $R_t$: 11.581 min; m/z 580.3 (M+H)$^+$.

Example 120

N-(2,6-dimethylphenyl)-2-[4-(isopropylcarbamoyl)-2-methoxy-anilino]-5,6-dihydropyrimido[4,5-e]indolizine-7-carboxamide This compound was prepared from its corresponding carboxylic acid (Example 103-c) and isopropylamine hydrochloride, using standard HATU-coupling procedures as described in Example 9. Purification was performed using preparative HPLC to afford the title compound (2.9 mg, 8%). Data: LCMS (B) $R_t$: 15.663 min; m/z 525.3 (M+H)$^+$.

Example 121

N-(2,6-dimethylphenyl)-2-[2-methoxy-4-[[(1R,5S)-3-oxabicyclo[3.1.0]hexan-6-yl]carbamoyl]anilino]-5,6-dihydropropyrimido[4,5-e]indolizine-7-carboxamide This compound was prepared from its corresponding carboxylic acid (Example 103-c) and (1R,5S)-3-oxabicyclo[3.1.0]hexan-6-amine hydrochloride, using standard HATU-coupling procedures as described in Example 9. Purification was performed using preparative HPLC to afford the title compound (6.5 mg, 15%). Data: LCMS (B) $R_t$: 14.186 min; m/z 565.2 (M+H)$^+$.

Example 122

N-(2,6-dimethylphenyl)-2-[2-methoxy-4-(morpholine-4-carbonyl)anilino]-5,6-dihydropyrimido[4,5-e]indolizine-7-carboxamide This compound was prepared from its corresponding carboxylic acid (Example 103-c) and morpholine, using standard HATU-coupling procedures as described in Example 9. Purification was performed using preparative HPLC to afford the title compound (8.7 mg, 15%). Data: LCMS (B) $R_t$: 14.262 min; m/z 553.3 (M+H)$^+$.

Example 123

N-(2,6-dimethylphenyl)-2-[4-(1,1-dioxo-1,4-thiazine-4-carbonyl)-2-methoxy-anilino]-5,6-dihydropyrimido[4,5-e]indolizine-7-carboxamide This compound was prepared from its corresponding carboxylic acid (Example 103-c) and thiomorpholine 1,1-dioxide, using standard HATU-coupling procedures as described in Example 9. Purification was performed using preparative HPLC to afford the title compound (10.5 mg, 14%). Data: LCMS (B) $R_t$: 13.936 min; m/z 601.2 (M+H)$^+$.

Example 124

N-(2,6-dimethylphenyl)-2-[4-(4-ethyl-1,4-diazepane-1-carbonyl)-2-methoxy-anilino]-5,6-dihydropyrimido[4,5-e]indolizine-7-carboxamide This compound was prepared from its corresponding carboxylic acid (Example 103-c) and 1-ethyl-1,4-diazepane dihydrochloride, using standard HATU-coupling procedures as described in Example 9. Purification was performed using preparative HPLC to afford the title compound (4.4 mg, 7%). Data: LCMS (B) $R_t$: 11.510 min; m/z 594.4 (M+H)$^+$.

Example 125

2-[4-[(3,3-Difluorocyclobutyl)carbamoyl]-2-methoxy-anilino]-N-(2,6-dimethylphenyl)-5,6-dihydropyrimido[4,5-e]indolizine-7-carboxamide This compound was prepared from its corresponding carboxylic acid (Example 103-c) and 3,3-difluorocyclobutanamine hydrochloride, using standard HATU-coupling procedures as described in Example 9. Purification was performed using preparative HPLC to afford the title compound (4.1 mg, 7%). Data: LCMS (B) $R_t$: 16.415 min; m/z 573.3 (M+H)$^+$.

Example 126

2-[4-(cyclopropylcarbamoyl)-2-methoxy-anilino]-N-(2,6-dimethylphenyl)-5,6-dihydropyrimido[4,5-e]indolizine-7-carboxamide This compound was prepared from its corresponding carboxylic acid (Example 103-c) and cyclopropylamine, using standard HATU-coupling procedures as described in Example 9. Purification was performed using preparative HPLC to afford the title compound (5.7 mg, 10%). Data: LCMS (B) $R_t$: 14.833 min; m/z 523.3 (M+H)$^+$.

Example 127

N-(2,6-dimethylphenyl)-2-[2-methoxy-4-(2-methoxyethylcarbamoyl)anilino]-5,6-dihydropyrimido[4,5-e]indolizine-7-carboxamide This compound was prepared from its corresponding carboxylic acid (Example 103-c) and 2-methoxyethylamine, using standard HATU-coupling procedures as described in Example 9. Purification was performed using preparative HPLC to afford the title compound (4.9 mg, 8%). Data: LCMS (B) $R_t$: 14.283 min; m/z 541.3 (M+H)$^+$.

Example 128

N-(2,6-dimethylphenyl)-2-[2-methoxy-4-[2-(1-piperidyl)ethylcarbamoyl]anilino]-5,6-dihydropyrimido[4,5-e]indolizine-7-carboxamide This compound was prepared from its corresponding carboxylic acid (Example 103-c) and 2-(1-piperidyl)ethanamine, using standard HATU-coupling procedures as described in Example 9. Purification was performed using preparative HPLC to afford the title compound (4.2 mg, 5%). Data: LCMS (B) $R_t$: 12.340 min; m/z 594.3 (M+H)$^+$.

Example 129

2-[4-(4-Cyano-4-methyl-piperidine-1-carbonyl)-2-methoxy-anilino]-N-(2,6-dimethylphenyl)-5,6-dihydropyrimido[4,5-e]indolizine-7-carboxamide This compound was prepared from its corresponding carboxylic acid (Example 103-c) and: 4-methylpiperidine-4-carbonitrile hydrochloride, using standard HATU-coupling procedures as described in Example 9. Purification was performed by flash chromatography on silica gel (dichloromethane/methanol=99/1 to 9/1 v/v %) to afford the title compound (3.9 mg, 5%). Data: LCMS (B) $R_t$: 15.853 min; m/z 590.3 (M+H)$^+$.

Example 130

N-(2,6-dimethylphenyl)-2-[2-methoxy-4-[4-(3-methylazetidine-3-carbonyl)piperazin-1-yl]anilino]-5,6-dihydropyrimido[4,5-e]indolizine-7-carboxamide This compound was prepared from its corresponding carboxylic acid (Example 17) and 1-tert-butoxycarbonyl-3- methyl-azetidine-3-carboxylic acid, using standard HATU-coupling procedures as described in Example 9. After deprotection of the Boc-group, purification was performed using preparative HPLC to afford the title compound (10 mg, 39%). Data: LCMS (B) $R_t$: 11.186 min; m/z 621.4 (M+H)$^+$.

Example 131

2-[4-(4-Acetylpiperazin-1-yl)-2-methoxy-anilino]-N-[1-(2-methoxyethyl)-3,5-dimethyl-pyrazol-4-yl]-5,6-dihydropyrimido[4,5-e]indolizine-7-carboxamide This compound was prepared from its corresponding amine (Example 16) and acetic acid, using standard HATU-coupling procedures as described in Example 9. Purification was performed using preparative HPLC to afford the title compound (17 mg, 45%). Data: LCMS (B) $R_t$: 10.096 min; m/z 614.3 (M+H)$^+$.

Example 132

2-[4-[4-(3-Fluorocyclobutanecarbonyl)piperazin-1-yl]-2-methoxy-anilino]-N-[1-(2-methoxyethyl)-3,5-dimethyl-pyrazol-4-yl]-5,6-dihydropyrimido[4,5-e]indolizine-7-carboxamide This compound was prepared from its corresponding amine (Example 16) and 3-fluorocyclobutanecarboxylic acid, using standard HATU-coupling procedures as described in Example 9. Purification was performed using preparative HPLC to afford the title compound (8 mg, 20%) Data: LCMS (B) $R_t$: 12.238 min; m/z 672.3 (M+H)$^+$.

Example 133

N-(2-cyano-6-methyl-phenyl)-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate F as starting material. The acid chloride was subsequently reached with 2-amino-3-methylbenzonitril according to procedures described in Example 2. Purification was performed by flash chromatography on silica gel (dichloromethane/methanol=99/1 to 9/1 v/v %) to afford the title compound (8.3 mg, 10%). Data: LCMS (B) $R_t$: 10.090 min; m/z 549.3 (M+H)$^+$.

Example 134

N-(2,6-diethylphenyl)-2-[4-[3-(dimethylamino)propyl-methyl-amino]-2-methoxy-anilino]-5,6-dihydropyrimido[4,5-e]indolizine-7-carboxamide This compound was prepared from its corresponding acid chloride, using the same sequence of reactions, as described for Intermediate 2, using Intermediate ZI as starting material. The acid chloride was subsequently reached with 2,6-diethylaniline according to procedures described in Example 2. Purification was performed using preparative HPLC to afford the title compound (6.6 mg, 14%). Data: LCMS (B) $R_t$: 12.601 min; m/z 582.4 (M+H)$^+$.

Example 135

2-[4-[3-(Dimethylamino)propyl-methyl-amino]-2-methoxy-anilino]-N-[1-[2-[2-(2-methoxyethoxy)ethoxy]ethyl]-3,5-dimethyl-pyrazol-4-yl]-5,6-dihydropyrimido[4,5-e]indolizine-7-carboxamide This compound was prepared from its corresponding acid chloride, using the same sequence of reactions, as described for Intermediate 2, using Intermediate ZI as starting material. The acid chloride was subsequently reacted with Intermediate Ah according to procedures described in Example 2. Purification was performed using preparative HPLC to afford the title compound (5.7 mg, 11%). Data: LCMS (B) $R_t$: 8.660 min; m/z 690.4 (M+H)$^+$.

Example 136

N-(2,6-diethylphenyl)-2-[2-methoxy-4-(2-methoxyethoxy)anilino]-5,6-dihydropyrimido[4,5-e]indolizine-7-carboxamide This compound was prepared from its corresponding acid chloride, using the same sequence of reactions, as described for Intermediate 2, using Intermediate ZJ as starting material. The acid chloride was subsequently reacted with 2,6-diethylaniline according to procedures described in Example 2. Purification was performed using preparative HPLC to afford the title compound (13.4 mg, 30%). Data: LCMS (B) $R_t$: 17.314 min; m/z 542.3 (M+H)$^+$.

Example 137

N-[1-[2-[2-(2-methoxyethoxy)ethoxy]ethyl]-3,5-dimethyl-pyrazol-4-yl]-2-[2-methoxy-4-(2-methoxyethoxy)anilino]-5,6-dihydropyrimido[4,5-e]indolizine-7-carboxamide This compound was prepared from its corresponding acid chloride, using the same sequence of reactions, as described for Intermediate 2, using Intermediate ZJ as starting material. The acid chloride was subsequently reacted with Intermediate Ah according to procedures described in Example 2. Purification was performed using preparative HPLC to afford the title compound (6.7 mg, 13%). Data: LCMS (B) $R_t$: 12.186 min; m/z 650.3 (M+H)$^+$.

Example 138

N-[1-[2-[2-(2-methoxyethoxy)ethoxy]ethyl]-3,5-dimethyl-pyrazol-4-yl]-2-[2-methoxy-4-(4-methyl-piperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate F as starting material. The acid chloride was subsequently reacted with Intermediate Ah according to procedures described in Example 2. Purification was performed using preparative HPLC to afford the title compound (11.6 mg, 28.6%). Data: LCMS (B) $R_t$: 6.985 min; m/z 674.3 (M+H)$^+$.

Example 139

N-[1-(azetidin-3-yl)-3,5-dimethyl-pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate F as starting material. The acid chloride was subsequently reacted with Intermediate Al according to procedures described in Example 2. After deprotection of the Boc-group, purification was performed using preparative HPLC to afford the title compound (6.9 mg, 19.7%). Data: LCMS (B) $R_t$: 4.784 min; m/z 583.3 (M+H)$^+$.

Example 140

N-[3,5-dimethyl-1-(oxetan-2-ylmethyl)pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate F as starting material. The acid chloride was subsequently reacted with Intermediate Aj according to procedures described in Example 2. Purification was performed by flash chromatography on silica gel (dichloromethane/methanol=99/1 to 9/1 v/v %) to afford the title compound (22.1 mg, 61.6%). Data: LCMS (B) $R_t$: 6.495 min; m/z 598.3 (M+H)$^+$.

Example 141

N-[3,5-diethyl-1-[2-(2-methoxyethoxy)ethyl]pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate F as starting material. The acid chloride was subsequently reacted with Intermediate Ak according to procedures described in Example 2. Purification was performed using preparative HPLC to afford the title compound (22 mg, 54.4%). Data: LCMS (B) $R_t$: 7.845 min; m/z 658.3 (M+H)$^+$.

Example 142

N-[3,5-diethyl-1-(oxetan-3-yl)pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate F as starting material. The acid chloride was subsequently reacted with Intermediate AI according to procedures described in Example 2. Purification was performed by flash chromatography on silica gel (dichloromethane/methanol=99/1 to 9/1 v/v %) to afford the title compound (23.8 mg, 64.8%). Data: LCMS (B) $R_t$: 7.412 min; m/z 612.3 (M+H)$^+$.

Example 143

N-[1-(2-dimethylaminoethyl)-3,5-dimethyl-pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate F as starting material. The acid chloride was subsequently reacted with Intermediate Am according to procedures described in Example 2. Purification was performed using preparative HPLC to afford the title compound (11.5 mg, 32.0%). Data: LCMS (B) $R_t$: 4.944 min; m/z 599.3 (M+H)$^+$.

Example 144

N-(2,6-dimethyl-phenyl)-2-[2-(difluoromethoxy)-4-(4-methylpiperazin-1-yl)anilino]-5,6-dihydropyrimido[4,5-e]indolizine-7-carboxamide This compound was prepared from its corresponding acid chloride, using the same sequence of reactions, as described for Intermediate 2, using Intermediate J as starting material. The acid chloride was subsequently reacted with 2,6-dimethylaniline according to procedures described in Example 2. Purification was performed using preparative HPLC to afford the title compound (11 mg, 27%). Data: LCMS (B) $R_t$: 11.461 min; m/z 574.3 (M+H)$^+$.

Example 145

N-(2,6-dimethylphenyl)-2-[4-[4-(isopropylcarbamoyl)piperazin-1-yl]-2-methoxy-anilino]-5,6-dihydropyrimido[4,5-e]indolizine-7-carboxamide To a stirred solution of N-(2,6-dimethylphenyl)-2-(2-methoxy-4-piperazin-1-yl-anilino)-5,6-dihydropyrimido[4,5-e]indolizine-7-carboxamide (Example 17, 37 mg, 0.063 mmol) in DCM (2 ml) was added 2-isocyanatopropane (8 μL, 0.07 mmol). The reaction mixture was stirred o/n at room temperature. The mixture was concentrated and the residue was purified using preparative HPLC to afford the title compound (6 mg, 16%). Data: LCMS (B)$R_t$: 14.299 min; m/z 609.4 (M+H)$^+$.

Example 146

Biochemical Kinase Assay

To determine the inhibitory activity of compounds on TTK enzyme activity, the IMAP® assay (Molecular Devices) was used. Compounds were serially diluted in dimethylsulfoxide (DMSO) and subsequently in 4% DMSO in IMAP reaction buffer, which consists of 10 mM Tris-HCl, pH 7.5, 10 mM $MgCl_2$, 0.01% Tween-200, 0.1% $NaN_3$ and 1 mM freshly prepared dithiotreitol (DTT). Compound solution was mixed with an equal volume of full-length TTK enzyme (Life Technologies, Cat. no. PV 3792) in IMAP reaction buffer. After pre-incubation of 1 hour in the dark at room temperature, fluorescein-labeled MBP-derived substrate peptide (Molecular Devices, cat. no. RP 7123) was added, followed by ATP to start the reaction. Final enzyme concentration was 3.9 nM final substrate concentration 50 nM, and final ATP concentration was 5 µM. The reaction was allowed to proceed for 2 hours at room temperature in the dark. The reaction was stopped by quenching with IMAP progressive binding solution according to the protocol of the manufacturer (Molecular Devices). Fluorescein polarization was measured on an Envision multimode reader (Perkin Elmer, Waltham, Mass., U.S.A.). $IC_{50}$ were calculated using XLfit™5 software (ID Business Solutions, Ltd., Surrey, U.K.). The $IC_{50}$ values of all exemplified compounds were found to be smaller than 100 nM.

Example 147

Cell Proliferation Assay

The MOLT-4 cancer cell line was purchased from the American Type Culture Collection (ATCC, Manassas, Va., U.S.A.) and cultured in RPMI 1640 medium (LifeTechnologies, Bleiswijk, The Netherlands), supplemented with 10% bovine calf serum. Compounds were serially diluted in 3.16 fold steps in 100% DMSO, followed by further dilution in aqueous buffer. Cells in medium were seeded at 45 µL per well in the wells of a 384-well plate, and incubated for 24 hours in a humidified atmosphere of 5% $CO_2$ at 37° C. 5 µL of compound solution was added and the plates were incubated for an additional 72 hours after which 25 µL of ATPlite 1Step™ (PerkinElmer, Groningen, The Netherlands) solution was added to each well. Luminescence was recorded on an Envision multimode reader. The cell signal at the start of incubation was recorded separately in order to distinguish between cell population growth and cell death. In addition, maximum growth was determined by incubation of a duplicate without compound in the presence of 0.4% DMSO. Percentage growth was used as the main y-axis signal. $IC_{50}$s were fitted by non-linear regression using IDBS XLfit™5 using a 4-parameter logistic curve, yielding a maximum signal, minimum signal, hill-parameter and $IC_{50}$.

The $IC_{50}$ values of all exemplified compounds were found to be smaller than 300 nM. Compounds of examples 3, 6, 7, 10, 11, 14-16, 20, 23-29, 31, 32, 34, 36, 38, 44, 52, 53, 77, 88, 90-92, 98, 102, 104, 128, 131, 132, 136, 140 and 142 showed an $IC_{50}$ value≥50 nM-<150 nM and compounds of examples 1, 2, 4, 5, 9, 13, 17-19, 21, 22, 33, 35, 37, 39-43, 45-51, 56, 58-61, 62-76, 78-84, 86, 93-97, 99, 100, 103, 105, 107, 109-114, 116-124, 126, 127, 129, 130, 133-135, 137, 138, 141, 144 and 145 showed an $IC_{50}$ of <50 nM.

Intermediate An

1-[2-(2-ethoxyethoxy)ethyl]-3,5-dimethyl-pyrazol-4-amine (a) 2-(2-ethoxyethoxy)ethyl 4-methylbenzenesulfonate To a solution of di(ethylene glycol) ethyl ether (4.92 ml, 36.2 mmol) in 15 mL of THF, cooled at 0° C., was added sodium hydroxide (2.46 g, 61.5 mmol) dissolved in 15 mL of water with vigorous stirring. To this mixture was added dropwise a solution of tosyl chloride (8.28 g, 43.4 mmol) in 15 mL of THF over a period of 10 min at 0° C. Cooling was subsequently removed and the reaction mixture was stirred for 1 h under nitrogen. After TLC analysis indicated a complete conversion of the starting material, the mixture was extracted twice with dimethyl ether (2×50 mL), and the organic layer was washed with 1N NaOH-solution (25 mL) and water (25 mL). The organic layer was dried ($Na_2SO_4$), filtered and solvent was removed under reduced pressure to yield crude 2-(2-ethoxyethoxy)ethyl 4-methylbenzenesulfonate as a colorless liquid, yield 10 g (95.8%).

(b) 1-[2-(2-ethoxyethoxy)ethyl]-3,5-dimethyl-4-nitro-pyrazole

To a solution of 3,5-dimethyl-4-nitro-1H-pyrazol (1 g, 7.08 mmol) and cesium carbonate (2.31 g, 7.08 mmol) in DMF (10 mL) was added 2-(2-ethoxyethoxy)ethyl 4-methylbenzenesulfonate (2.04 g, 7.08 mmol). The mixture was heated at 100° C. for 1 h. The mixture was cooled to room temperature and poured into water/brine and extracted with ethyl acetate (100 mL). The combined organic layers were washed with bring (50 mL), dried over sodium sulfate, filtered and concentrated in vacuo to yield 1.69 g of the title compound (92.8%)

(c) 1-[2-(2-ethoxyethoxy)ethyl]-3,5-dimethyl-pyrazol-4-amine

To a stirred solution of 1-[2-(2-ethoxyethoxy)ethyl]-3,5-dimethyl-4-nitro-pyrazole (1.69 g, 6.57 mmol) in methanol (25 mL) was added a suspension of 10% Pd on charcoal (200 mg) in ethanol (1 mL). The reaction mixture was stirred at room temperature for 15 min under a nitrogen atmosphere. Then, ammonium formate (4.14 g, 65.7 mmol) was added and the reaction mixture was heated to reflux temperature for 15 min. The reaction mixture was cooled, filtered over Decalite® and concentrated in vacuo. The residue was dissolved in methanol and then filtered over an SCX-2 column. After rinsing the column with methanol, the desired product was eluted with an 0.7N ammonia/methanol solution. The resulting eluate was concentrated in vacuo to give the title compound (520 mg, 34.8%).

Intermediate Ao

1-[2-(2-Methoxyethoxy)ethyl]-3,5-dimethyl-pyrazol-4-amine

The title compound was prepared in an analogous manner as described for Intermediate An, starting from diethylene glycol methyl ether and 3,5-dimethyl-4-nitro-1H-pyrazole to give 500 mg of 1-[2-(2-methoxyethoxy)ethyl]-3,5-dimethyl-pyrazol-4-amine (34.8%).

Intermediate Ap

1-[2-(2-Ethoxyethoxy)ethyl]-3,5-diethyl-pyrazol-4-amine

The title compound was prepared in an analogous manner as described for Intermediate An, starting form 3,5-diethyl-4-nitro-1H-pyrazole (Intermediate Ac-b) and di(ethylene glycol)ethyl ether to give 550 mg of 1-[2-(2-ethoxyethoxy) ethyl]-3,5-diethyl-pyrazol-4-amine (79.8%).

Intermediate Aq 3,5-Diethyl-1-[2-[2-(2-methoxyethoxy)ethoxy]ethyl] pyrazol-4-amine The title compound was prepared in an analogous manner as described for Intermediate An, starting form 3,5-diethyl-4-nitro-1H-pyrazole (Intermediate Ac-b) and triethylene glycol monomethyl ether to give 660 mg of 3,5-diethyl-1-[2-[2-(2-methoxyethoxy)ethoxy]ethyl]pyrazol-4-amine (41.7%).

Example 148

N-[1-[2-(2-ethoxyethoxy)ethyl]-3,5-dimethyl-pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid, using the same sequence of reactions as described for Intermediate 2 using Intermediate F as starting material. The carboxylic acid was subsequently reacted with Intermediate An in an analogous manner as described for Example 9. Purification was performed using preparative HPLC to afford the title compound (32.3 mg, 53.9%). Data; LCMS (B) $R_t$: 7.432 min; m/z 644.6 (M+H)$^+$.

Example 149

N-[1-[2-(2-methoxyethoxy)ethyl]-3,5-dimethyl-pyrazol-4-yl]-2-[2-methoxy-4-(4-methylpiperazin-1-yl)anilino]-b,6-dihydropyrimido[4,5-e]indolizine-7-carboxamide This compound was prepared from its corresponding acid, using the same sequence of reactions as described for Intermediate 2 using Intermediate F as starting material. The carboxylic acid was subsequently reacted with Intermediate Ao in an analogous manner as described for Example 9. Purification was performed using preparative HPLC to afford the title compound (31.5 mg, 53.7%). Data: LCMS (B) $R_t$: 6.806 min; m/z 630.7 (M+H)$^+$.

Example 150

N-[1-[2-(2-ethoxyethoxy)ethyl]-3,5-diethyl-pyrazol-4-yl]-2-[2-methoxy-4-(4-methylpiperazin-1-yl)anilino]-5,6-dihydropyrimido[4,5-e]indolizine-7-carboxamide This compound was prepared from its corresponding acid, using the same sequence of reactions as described for Intermediate 2 using Intermediate F as starting material. The carboxylic acid was subsequently reacted with Intermediate Ap in an analogous manner as described for Example 9. Purification was performed using preparative HPLC to afford the title compound (34.2 mg, 54.8%). Data: LCMS (B) $R_t$: 8.430 min; m/z 672.7 (M+H)$^+$.

Example 151

N-[1-[2-(2-ethoxyethoxy)ethyl]-3,5-diethyl-pyrazol-4-yl]-2-(2-methoxy-4-piperazin-1-yl-anilino)-5,6-dihydropyrimido[4,5-e]indolizine-7-carboxamide This compound was prepared from its corresponding acid, using the same sequence of reactions as described for Intermediate 2 using Intermediate F as starting material. The carboxylic acid was subsequently reacted with Intermediate Ap in an analogous manner as described for Example 9. After deprotection of the Cbz-group purification was performed using preparative HPLC to afford the title compound (147.4 mg, 93.4%). Data: LCMS (A) $R_t$: 4.376 min; m/z 658.7 (M+H)$^+$.

Example 152

N-[1-[2-(2-ethoxyethoxy)ethyl]-3,5-diethyl-pyrazol-4-yl]-2-[2-methoxy-4-[4-(2-methoxyacetylpiperazin-1-yl]anilino]-5,6-dihydropyrimido[4,5-e]indolizine-7-carboxamide This compound was prepared from its corresponding amine (Examine 151) and methoxyacetic acid, using standard HATU-coupling procedures as described in Example 9. Purification was performed using preparative HPLC to afford the title (17.0 mg, 61.4%). Data: LCMS (B) $R_t$: 10.554 min; m/z 730.7 (M+H)$^+$.

Example 153

N-[1-[2-(2-ethoxyethoxy)ethyl]-3,5-diethyl-pyrazol-4-yl]-2-[4-[4-[2-(ethylamino)acetyl]piperazin-1-yl]-2-methoxy-anilino]-5,6-dihydropyrimido[4,5-e]indolizine-7-carboxamide This compound was prepared from its corresponding amine (Examine 151) and Boc-N-ethyl-glycine, using standard HATU-coupling procedures as described in Example 9. After deprotection of the Boc-group, purification was performed using preparative HPLC to afford the title compound (15.0 mg, 53.1%). Data: LCMS (B) $R_t$: 8.619 min; m/z 743.8 (M+H)$^+$.

Example 154

N-[3,5-diethyl-1-[2-[2-(2-methoxyethoxy)ethoxy]ethyl]pyrazol-4-yl]-2-[2-methoxy-4-[4-(2-methoxyacetyl)piperazin-1-yl]anilino]-5,6-dihydropyrimido[4,5-e]indolizine-7-carboxamide This compound was prepared from its corresponding amine, prepared in an analogous manner as described for Examine 151 using Intermediate 2, Intermediate ZE and Intermediate Aq, and methoxyacetic acid, using standard HATU-coupling procedures as described in Example 9. Purification was performed using preparative HPLC to afford the title compound (17.8 mg, 57.1%). Data: LCMS (B) $R_t$: 9.908 min; m/z 760.8 (M+H)$^+$.

Example 155

N-[1-(2-methoxyethyl)-3,5-dimethyl-pyrazol-4-yl]-2-[2-methoxy-4-[4-(1-methylazetidine-3-carbonyl)piperazin-1-yl]anilino]-5,6-dihydropyrimido[4,5-e]indolizine-7-carboxamide This compound was prepared from its corresponding amine (Example 16) and 1-methyl-3-azetidinecarboxylic acid, using standard HATU-coupling procedures as described in Example 9. Purification was performed using preparative HPLC to afford the title compound (0.5 mg, 1%). Data: LCMS (A) $R_t$: 3.892 min; m/z 669.7 (M+H)$^+$.

Example 156

N-[1-[2-[2-(2-methoxyethoxy)ethoxy]ethyl]-3,5-dimethyl-pyrazol-4-yl]-2-(2-methoxy-4-piperazin-1-yl-anilino)-5,6-dihydropyrimido[4,5-e]indolizine-7-carboxamide This compound was prepared from its corresponding acid, using the same sequence of reactions as described for Intermediate 2 using Intermediate ZE as starting material. The carboxylic acid was subsequently reacted with Intermediate Ah in an analogous manner as described for Example 9. After deprotection of the Cbz-group, purification was performed using preparative HPLC to afford the title compound (189.4 mg, 95.7%). Data: LCMS (A) $R_t$: 3.811 min; m/z 660.7 (M+H)$^+$.

Example 157

2-[4-[4-[2-(Ethylamino)acetyl]piperazin-1-yl]-2-methoxy-anilino]-N-[1-[2-[2-(2-methoxyethoxy)ethoxy]ethyl]-3,5-dimethyl-pyrazol-4-yl]-5,6-dihydropyrimido[4,5-e]indolizine-7-carboxamide This compound was prepared from its corresponding amine (Example 156) and Boc-N-ethyl-glycine, using standard HATU-coupling procedures as described in Example 9. After deprotection of the Boc-group, purification was performed using preparative HPLC to afford the title compound (18.9 mg, 61.8%). Data: LCMS (B) $R_t$: 7.255 min; m/z 745.8 (M+H)$^+$.

Example 158

N-[3,5-diethyl-1-[2-(2-methoxyethoxy)ethyl]pyrazol-4-yl]-2-[4-[4-[2-(ethylamino)acetyl]piperazin-1-yl]-2-methoxy-anilino]-5,6-dihydropyrimido[4,5-e]indolizine-7-carboxamide This compound was prepared from its corresponding acid, using the same sequence of reactions as described for Intermediate 2 using Intermediate ZE as starting material. The carboxylic acid was subsequently reacted with Intermediate Ak in an analogous manner as described for Example 9. After deprotection of the Cbz-group, Boc-N-ethyl-glycine was introduced using standard HATU-coupling procedures as described in Example 9. After deprotection of the Boc-group, purification was performed using preparative HPLC to afford the title compound (15.8 mg, 54.2%). Data: LCMS (B) $R_t$: 8.002 min; m/z 729.8 (M+H)$^+$.

Example 159

N-[3,5-diethyl-1-[2-(2-methoxyethoxy)ethyl]pyrazol-4-yl]-2-[2-methoxy-4-[4-(2-methoxyacetyl)piperazin-1-yl]anilino]-5,6-dihydropyrimido[4,5-e]indolizine-7-carboxamide This compound was prepared from its corresponding acid, using the same sequence of reactions as described for Intermediate 2 using Intermediate ZE as starting material. The carboxylic acid was subsequently reacted with Intermediate Ak in an analogous manner as described for Example 9. After deprotection of the Cbz-group, methoxyacetic acid was introduced using standard HATU-coupling procedures as described in Example 9. Purification was performed using preparative HPLC to afford the title compound (17.3 mg, 60.4%). Data: LCMS (B) $R_t$: 9.848 min; m/z 716.7 (M+H)$^+$.

Example 160

N-[1-[2-[2-(2-methoxyethoxy)ethoxy]ethyl]-3,5-dimethyl-pyrazol-4-yl]-2-[2-methoxy-4-(1,3,5-trimethylpyrazol-4-yl)anilino]-5,6-dihydropyrimido[4,5-e]indolizine-7-carboxamide This compound was prepared from its corresponding acid, using the same sequence of reactions as described for Intermediate 2 using Intermediate R as starting material. The carboxylic acid was subsequently reacted with Intermediate Ah in an analogous manner as described in Example 9. Purification was performed using preparative HPLC to afford the title compound (19.5 mg, 42.6%). Data: LCMS (B) $R_t$: 10.946 min; m/z 68.47 (M'H)$^+$.

Compounds of examples 148, 149, 150, 151, 152, 153, 154, 155, 156, 157, 158, 159 and 160 showed an IC$_{50}$ value of <50 nM in the TTK biochemical assay.

Compounds of examples 148, 149, 150, 151, 152, 153, 154, 155, 156, 157, 158, 159 and 160 showed an IC$_{50}$ value of <50 nM in the TTK cellular assay.

Example 161

Biochemical Aurora A Kinase Assay

To determine the inhibitory activity of the compounds on Aurora A, the LANCE® Ultra TR-FRET assay (Perkin Elmer) was used. Compounds were serially diluted in dimethylsulfoxide (DMSO) and subsequently in 4% DMSO in LANCE® kinase buffer, which consists of 50 mM Hepes, pH 7.5, 10 mM MgCl$_2$, 1 mM EGTA, 0.01% Tween-20, and 2 mM dithioreitol (DTT). 2.5 µl of compound solution was mixed with an equal volume of full-length Aurora A enzyme (Carna Biosciences, cat. no. 05-101) in LANCE® kinase buffer. After pre-incubation of 1 hour in the dark at room temperature, ULight™-labeled PLK(Ser137) substrate enzyme concentration was 2.5 nM; final substrate concentration was 25 nM; final ATP concentration was 2 µM; final DMSO concentration in each well was 1%. After 2 hours, the reaction was stopped by the addition of 5 µl 100 mM EDTA. After 5 min incubation at room temperature, 5 µl of Europium-labeled anti-phospho-PLK (Ser137) substrate antibody (Perkin Elmer, cat. no. TRF-0203) was added and the incubation was continued for 1 hour in the dark at room temperature. Time-resolved fluorescence was measured on an Envision multilabel reader (Perkin Elmer, Waltham, Mass., USA). IC$_{50}$ were calculated using XLfit™5 software (ID Business Solutions, Ltd., Surrey, U.K.). Compounds of examples 33, 138, 141, 148, 149, 150, 151, 152, 153, 154, 155, 156, 157, 158, 159 and 160 showed an IC$_{50}$ value≥100 nM.

Example 162

Biochemical Aurora C Kinase Assay

To determine the inhibitory activity of the compounds on Aurora C, the LANCE® Ultra TR-FRET assay (Perkin Elmer) was used. Compounds were serially diluted in dimethylsulfoxide (DMSO) and subsequently in 4% DMSO in LANCE® kinase buffer, which consists of 50 mM Hepes, pH 7.5, 10 mM MgCl$_2$, 1 mM EGTA, 0.01% Tween-20, and 2 mM dithioreitol (DTT). 2.5 µl of compound solution was mixed with an equal volume of full-length Aurora C enzyme (Carna Biosciences, cat. no. 05-103) in LANCE® kinase buffer. After pre-incubation of 1 hour in the dark at room temperature, ULight™-labeled PLK(Ser137) substrate peptide (Perkin Elmer, cat. no. TRF-0110) and ATP were added, to start the reaction. Final enzyme concentration was 10 nM; final substrate concentration was 25 nM; final ATP concentration was 5 µM; final DMSO concentration in each well was 1%. After 3 hours, the reaction was stopped by the addition of 5 µl 100 mM EDTA. After 5 min incubation at room temperature, 5 µl of Europium-labeled anti-phospho-PKL (Ser137) substrate antibody (Perkin Elmer, cat. no. TRF-0203) was added and the incubation was continued for 1 hour in the dark at room temperature. Time-resolved fluorescence was measured on an Envision multilabel reader (Perkin Elmer, Waltham, Mass., USA). $IC_{50}$ were calculated using XLfit™5 software (ID Business Solutions, Ltd., Surrey, U.K.).

Compounds of examples 33, 138, 141, 148, 149, 150, 151, 152, 153, 154, 155, 156, 157, 158, 159 and 160 showed an $IC_{50}$ value≥100 nM.

Example 163

Biochemical Polo-Like Kinase 1 Kinase Assay

To determine the inhibitory activity of the compounds on Polo-like kinase 1 (PLK1), the LANCE® Ultra TR-FRET assay (Perkin Elmer) was used. Compounds were serially diluted in dimethylsulfoxide (DMSO) and subsequently in 4% DMSO in LANCE® kinase buffer, which consists of 50 mM Hepes, pH 7.5, 10 mM $MgCl_2$, 1 mM EGTA, 0.01% Tween-20, and 2 mM dithiotreitol (DTT). 2.5 µl of compound solution was mixed with an equal volume of of full-length PLK1 enzyme (Carna, cat. no. 05-157) in LANCE® kinase buffer. After pre-incubation of 1 hour in the dark at room temperature, ULight™-labeled p70S6K (Thr389) substrate peptide (Perkin Elmer, cat. no. TRF-0126) and ATP were added, to start the reaction. Final enzyme concentration was 7.5 nM; final substrate concentration was 50 nM; final ATP concentration was 5 µM; final DMSO concentration in each well was 1%. After 4 hours, the reaction was stopped by the addition of 5 µl 100 mM EDTA. After 5 min incubation at room temperature, 5 µl of Europium-labeled anti-phospho-p70S6 (Thr389) substrate antibody (Perkin Elmer, cat. no. TRF-0214) was added and the incubation was continued for 1 hour in the dark at room temperature. Time-resolved fluorescence was measured on an Envision multilabel reader (Perkin Elmer, Waltham, Mass. USA). $IC_{50}$ were calculated using XLfit™5 software (ID Business Solutions, Ltd., Surrey, U.K.).

Compounds of examples 33, 138, 141, 148, 149, 150, 151, 152, 153, 154, 155, 156, 157, 158, 159 and 160 showed an $IC_{50}$ value≥250 nM.

TABLE A

Selectivity for TTK enzyme activity

| Example | AurA Selectivity[a] | AurC Selectivity[b] | PLK1 Selectivity[c] |
|---|---|---|---|
| 33 | >500 | >500 | >500 |
| 138 | >500 | >500 | >500 |
| 141 | >200 | >500 | >500 |
| 148 | >500 | >500 | >500 |
| 149 | >200 | >500 | >500 |
| 150 | >200 | >500 | >500 |
| 151 | >100 | >500 | >500 |
| 152 | >200 | >500 | >500 |
| 153 | >200 | >500 | >500 |
| 154 | >100 | >200 | >500 |
| 155 | >200 | >500 | >500 |
| 156 | >200 | >500 | >500 |
| 157 | >200 | >500 | >500 |
| 158 | >200 | >500 | >500 |
| 159 | >200 | >200 | >500 |
| 160 | >200 | >500 | >500 |

[a]AurA Selectivity means $IC_{50}$ AurA/$IC_{50}$ TTK (biochemical assays)
[b]AurC Selectivity means $IC_{50}$ AurC/$IC_{50}$ TTK (biochemical assays)
[c]PLK1 Selectivity means $IC_{50}$ PLK1/$IC_{50}$ TTK (biochemical assays)

The invention claimed is:
1. A compound of Formula I:

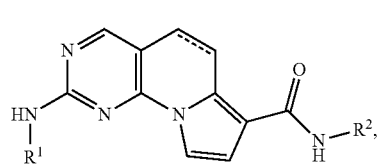

Formula I or a pharmaceutically acceptable salt thereof wherein, $R^1$ is selected from the group consisting of:

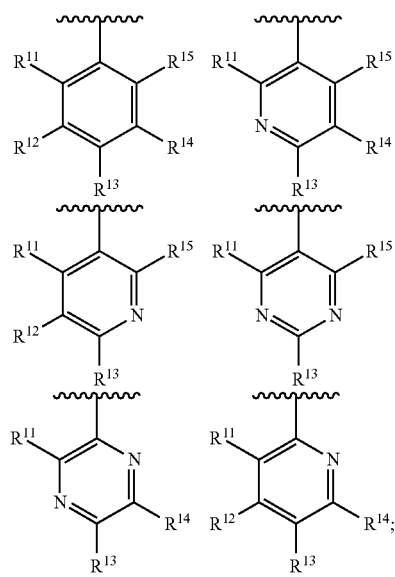

$R^{11}$ is H, halogen, (1-2C)alkyl, (2-3C)alkenyl, (2-3C)alkynyl, (1-2C)alkoxy or $OC^2H_3$, all alkyl and alkoxy groups optionally being substituted with one or more halogen;

$R^{12}$ is H, halogen, (1-2C)alkyl or (1-2C)alkoxy;

$R^{13}$ is $R^{131}CH_2$, $R^{132}O$, $R^{133}R^{134}N$, $R^{135}C(O)$, $R^{136}S$, $R^{136}S(O)$, $R^{136}S(O)(NH)$, $R^{137}SO_2$, (2-7C)heterocycloalkyl or (1-5C)heteroaryl, each heterocycloalkyl or heteroaryl optionally being substituted with (1-2C)alkyl, fluoro, hydroxyl, oxo, (1-2C)alkoxy, (1-6C)alkylcarbonyl, (1-6C)alkylsulfonyl, (1-5C)alkoxycarbonyl, (1-6C)alkylaminocarbonyl, (3-6C)cycloalkylcarbonyl, (2-7C)heterocycloalkylcarbonyl or di[(1-6C)alkyl]amino, each alkylcarbonyl, alkyl sulfonyl, alkoxycarbonyl, alkylaminocarbonyl, cycloalkylcarbonyl or heterocycloalkylcarbonyl optionally being substituted with (1-2C)alkyl, fluoro, hydroxyl, cyano, oxo or (1-2C)alkoxy;

$R^{131}$ is (1-6C)alkylcarbonylamino, (3-6C)cycloalkylcarbonylamino or (2-7C)heterocycloalkylcarbonylamino, each optionally substituted with one or more groups selected from (1-2C)alkyl, fluoro, hydroxyl or (1-2C)alkoxy;

$R^{132}$ is (1-6C)alkyl, (3-6C)cycloalkyl, (2-7C)heterocycloalkyl, (6-10C)aryl or (1-5C)heteroraryl, each optionally substituted with one or more groups selected from (1-2C)alkyl, halogen, hydroxyl, (1-2C)alkoxy, di[(1-2C)alkyl]amino or (2-7C)heterocycloalkyl;

R¹³³ is (1-6C)alkyl, (3-6C)cycloalkyl, (2-7C)heterocycloalkyl, (1-6C)alkylcarbonyl, (1-5C)alkoxycarbonyl, (3-6C)cycloalkylcarbonyl or (2-7C)heterocycloalkylcarbonyl, each optionally substituted with one or more groups selected from (1-2C)alkyl, halogen, hydroxyl, (1-2C)alkoxy, di[(1-2C)alkyl]amino or (2-7C)heterocycloalkyl;

R¹³⁴ is hydrogen or (1-2C)alkyl;

R¹³⁵ is (2-7C)heterocycloalkyl, (1-6C)alkylamino, di[(1-6C)alkyl]amino, (2-7C)heterocycloalkylamino or (3-6C)cycloalkylamino, each optionally substituted with one or more groups selected from (1-2C)alkyl, fluoro, hydroxyl, (1-2C)alkoxy, di[(1-2C)alkyl]amino, (2-7C)heterocycloalkyl, oxo, cyano or amino;

R¹³⁶ is (1-6C)alkyl, (3-6C) cycloalkyl or (2-7C)heterocycloalkyl, each optionally substituted with one or more groups selected from (1-2C)alkyl, fluoro, hydroxyl or (1-2C)alkoxy;

R¹³⁷ is (1-6C)alkyl, (3-6C)cycloalkyl, (2-7C)heterocycloalkyl, (1-6C)alkylamino, di[(1-6C)alkyl]amino, (2-7C)heterocycloalkylamino or (3-6C)cycloalkylamino, each optionally substituted with one or more groups selected from (1-2C)alkyl, fluoro, hydroxyl or (1-2C)alkoxy;

R¹⁴ is H, halogen, (1-2C)alkyl or (1-2C)alkoxy;

R¹⁵ is H or halogen;

R² is selected from the group consisting of:

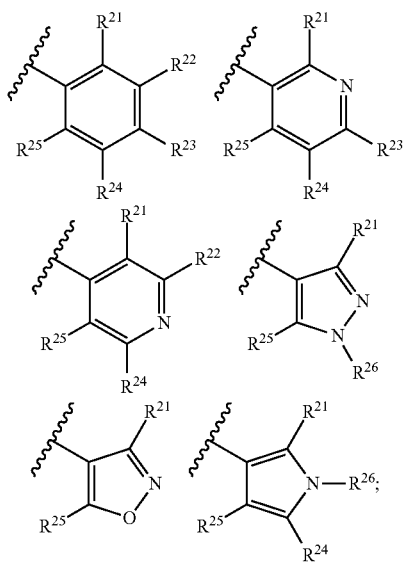

R²¹ is H, halogen, (1-3C)alkyl, (1-2C)alkoxy, hydroxy(1-2C)alkyl, (3-4C)cycloalkyl, (2-3C)alkenyl or cyano;
R²² is H, halogen, (1-2C)alkyl or (1-2C)alkoxy;
R²³ is H, halogen, (1-2C)alkyl, (1-2C)alkoxy, cyano or hydroxy;
R²⁴ is H, halogen, (1-2C)alkyl or (1-2C)alkoxy;
R²⁵ is H, halogen, (1-3C)alkyl, (1-2C)alkoxy, hydroxy(1-2C)alkyl, (3-4C)cycloalkyl, (2-3C)alkenyl or cyano; and
R²⁶ is H, (1-6C)alkyl, (3-6C)cycloalkyl, (2-5C)heterocycloalkyl or (1-2C)alkoxy[(2-4C)alkoxy]ₙ(1-6C)alkyl, wherein n represents an integer of 1, 2, 3 or 4, all alkyl, heterocycloalkyl and (1-2C)alkoxy[(2-4C)alkoxy]ₙ(1-6C)alkyl groups optionally being substituted with one or more groups selected from halogen, (1-2C)alkyl, (1-2C)alkoxy, hydroxyl, oxo, amino, (3-6C)cycloalkyl, di[(1-2C)alkyl]amino or (2-5C)heterocycloalkyl;

with the proviso that only one of R²¹ or R²⁵ in R² is H.

2. The compound according to claim 1, wherein

R¹³ is R¹³²O, R¹³⁵C(O), (2-7C)heterocycloalkyl or (1-5C)heteroaryl, each heterocycloalkyl or heteroaryl optionally being substituted with (1-2C)alkyl, (1-6C)alkylcarbonyl, (1-6C)alkylsulfonyl, (1-5C)alkoxycarbonyl, (1-6C)alkylaminocarbonyl, (3-6C)cycloalkylcarbonyl or (2-7C)heterocycloalkylcarbonyl, each alkylcarbonyl, alkyl sulfonyl, alkoxycarbonyl, alkylaminocarbonyl, cycloalkylcarbonyl or heterocycloalkylcarbonyl optionally being substituted with (1-2C)alkyl, fluoro or (1-2C)alkoxy;

R¹³² is (1-6C)alkyl, (3-6C)cycloalkyl, (2-7C)heterocycloalkyl, (6-10C)aryl or (1-5C)heteroaryl, each optionally substituted with one or more groups selected from (1-2C)alkyl, halogen, hydroxyl, (1-2C)alkoxy, di[(1-2C)alkyl]amino or (2-7C)heterocycloalkyl; and R¹³⁵ is (2-7C)heterocycloalkyl, (1-6C)alkylamino, di[(1-6C)alkyl]amino, (2-7C)heterocycloalkylamino or (3-6C)cycloalkylamino, each optionally substituted with one or more groups selected from (1-2C)alkyl, fluoro, hydroxyl, (1-2C)alkoxy, di[(1-2C)alkyl]amino, (2-7C)heterocycloalkyl, oxo, cyano or amino.

3. The compound according to claim 1, wherein

R¹³ is R¹³²O or R¹³⁵C(O); or R¹³ is piperidinyl, piperazinyl, morpholinyl, pyrazolyl or isoxazolyl, each optionally being substituted with (1-2C)alkyl, (1-6C)alkylcarbonyl, (1-6C)alkylsulfonyl, (1-5C)alkoxycarbonyl, (1-6C)alkylaminocarbonyl, (3-6C)cycloalkylcarbonyl or (2-7C)heterocycloalkylcarbonyl, each alkylcarbonyl, alkylsulfonyl, alkoxycarbonyl, alkylaminocarbonyl, cycloalkylcarbonyl or heterocycloalkylcarbonyl optionally being substituted with (1-2C)alkyl, fluoro or (1-2C)alkoxy;

R¹³² is (1-6C)alkyl, piperidinyl, pyrrolidinyl or azetidinyl, each optionally being substituted with one or more groups selected from (1-2C)alkyl, (1-2C)alkoxy or di[(1-2C)alkyl]amino; and R¹³⁵ is piperidinyl, thiomorpholinyl, morpholinyl, homopiperazinyl, (1-6C)alkylamino, (3-6C)cycloalkylamino or piperidinylamino, azetidinylamino, tetrahydropyranylamino or 3-oxabicyclo[3.1.0]hexan-6-amino, each optionally being substituted with one or more groups selected from (1-2C)alkyl, fluoro, hydroxyl or (1-2C)alkoxy, di[(1-2C)alkyl]amino, (2-7C)heterocycloalkyl, oxo, cyano or amino.

4. The compound according to claim 1, wherein R¹ is selected from the group consisting of:

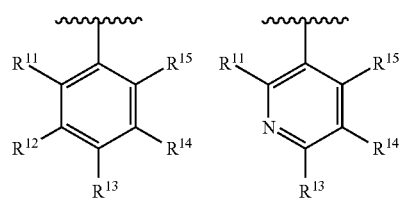

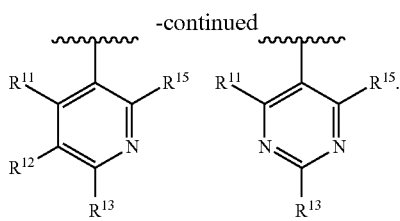

5. The compound according to claim 1, wherein $R^{12}$ and $R^{15}$ each are H and $R^{14}$ is H, fluoro, chloro, or (1-2C)alkyl.

6. The compound according to claim 1, wherein $R^{11}$ is H, (1-2C)alkyl or (1-2C)alkoxy, all alkyl and alkoxy groups optionally being substituted with one or more fluoro.

7. The compound according to claim 1, wherein $R^2$ is selected from the group consisting of:

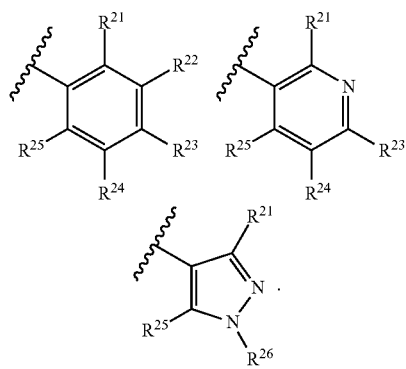

8. The compound according to claim 1, wherein $R^2$ is:

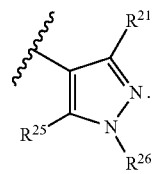

9. The compound according to claim 1, wherein $R^{23}$ is H or (1-2C)alkyl and $R^{22}$ and $R^{24}$ each are H and $R^{21}$ and $R^{25}$ are independently halogen, (1-3C)alkyl, methoxy, hydroxymethyl or cyano.

10. The compound according to claim 1, wherein $R^{26}$ is H, (1-6C)alkyl, oxetanyl, azetidinyl or (1-2C)alkoxy[(2-4C)alkoxy]$_n$(1-6C)alkyl, wherein n represents an integer of 1 or 2, all alkyl, oxetanyl and azetidinyl groups optionally being substituted with one or more groups selected from (1-2C)alkyl, (1-2C)alkoxy, hydroxyl, di[(1-2C)alkyl]amino or oxetanyl.

11. A pharmaceutical composition comprising the compound according to claim 1 or a pharmaceutically acceptable salt thereof and one or more pharmaceutically acceptable excipients.

12. The pharmaceutical composition according to claim 11, which further comprises at least one additional therapeutically active agent.

13. A method of treating breast cancer, comprising administering an effective amount of the compound according to claim 1 or a pharmaceutically acceptable salt thereof to a subject having breast cancer.

* * * * *